United States Patent
Yoshida et al.

(10) Patent No.: US 6,476,393 B1
(45) Date of Patent: Nov. 5, 2002

(54) SURFACE STATE MONITORING METHOD AND APPARATUS

(75) Inventors: Haruo Yoshida, Tokyo (JP); Michiaki Endo, Tokyo (JP); Michio Niwano, 18-12, Sumiyoshidai Higashi 3-chome, Izumi-ku, Sendai-shi, Miyagi-ken, 981-3222 (JP); Nobuo Miyamoto, 26-15, Sakuragaoka 7-chome, Aoba-ku, Sendai-shi, Miyagi-ken, 981-0961 (JP); Yasuhiro Maeda, Tokyo (JP)

(73) Assignees: Advantest. Corp, Tokyo (JP); Michio Niwano, Miyagi (JP); Nobuo Miyamoto, Miyagi (JP)

( * ) Notice: Subject to any disclaimer, the term of this patent is extended or adjusted under 35 U.S.C. 154(b) by 0 days.

(21) Appl. No.: 09/321,505

(22) Filed: May 27, 1999

(30) Foreign Application Priority Data

May 28, 1998 (JP) .......................... 10-147802
Jun. 4, 1998 (JP) .......................... 10-155829
Apr. 2, 1999 (JP) .......................... 11-095853

(51) Int. Cl.[7] .................. G01N 21/00; G01N 21/88
(52) U.S. Cl. .................. 250/341.8; 250/339.11
(58) Field of Search ............ 250/341.8, 339.01, 250/339.06, 339.07, 339.08, 339.11, 341.4, 324; 356/239

(56) References Cited

U.S. PATENT DOCUMENTS

| 5,321,264 A | * | 6/1994 | Kuwabara et al. ..... 250/339.01 |
| 5,381,234 A | * | 1/1995 | Barbee et al. ............... 356/369 |
| 5,386,121 A | * | 1/1995 | Barbee et al. ........... 250/341.8 |
| 5,534,698 A | * | 7/1996 | Oshima et al. ......... 250/339.11 |
| 5,550,374 A | * | 8/1996 | Holzer et al. ........... 250/339.07 |
| 5,895,918 A | * | 4/1999 | Powell et al. ........... 250/339.08 |
| 5,910,842 A | * | 6/1999 | Piwonka-Corle et al. ... 356/369 |
| 6,310,348 B1 | * | 10/2001 | Melling et al. ............. 250/341 |

FOREIGN PATENT DOCUMENTS

| DE | 32 00 008 A1 | 7/1983 |
| DE | 43 43 076 A1 | 6/1995 |
| DE | 196 05 255 A1 | 8/1996 |
| EP | 0 619 484 A1 | 10/1994 |
| EP | 0 919 802 A2 | 11/1998 |
| JP | Hei 07-239305 A | 12/1995 |
| JP | Hei 08-220008 A | 8/1996 |

* cited by examiner

Primary Examiner—Constantine Hannaher
Assistant Examiner—Albert Gagliardi
(74) Attorney, Agent, or Firm—Muramatsu & Associates

(57) ABSTRACT

A surface state monitoring method and apparatus for performing in-situ monitoring of surface states of semiconductor substrates. The apparatus comprises condensing means 30 for condensing infrared radiation to an outer peripheral part of the substrate-to-be-monitored; control means 80 for controlling an incident angle of the infrared radiation condensed by the condensing means 30; condensing means 40 for condensing the infrared radiation which has undergone multiple reflection in the substrate-to-be-monitored; detecting means 50 for detecting the infrared radiation condensed by the infrared radiation condensing means 40, and analyzing means 60 for analyzing the detected infrared radiation detected and measuring contaminants staying on the surfaces of the substrate-to-be-monitored.

57 Claims, 37 Drawing Sheets

| POINT | x | y |
|---|---|---|
| A | 75 μm | 0 μm |
| B | 500 μm | 0 μm |
| C | 50 μm | 258 μm |
| D | 0 μm | 75 μm |

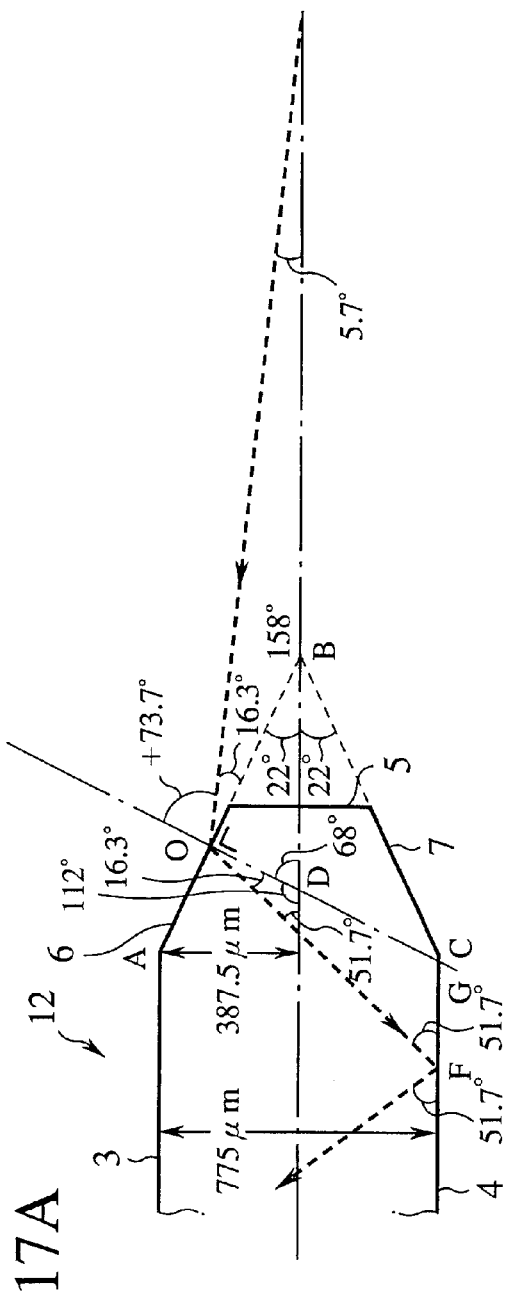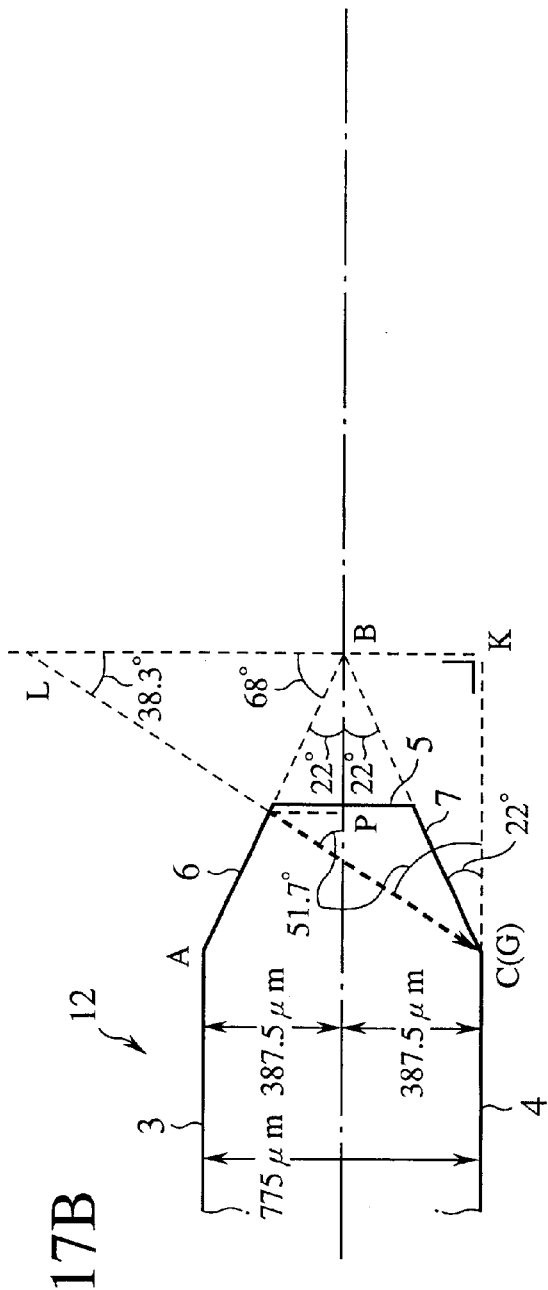
FIG. 17A
FIG. 17B

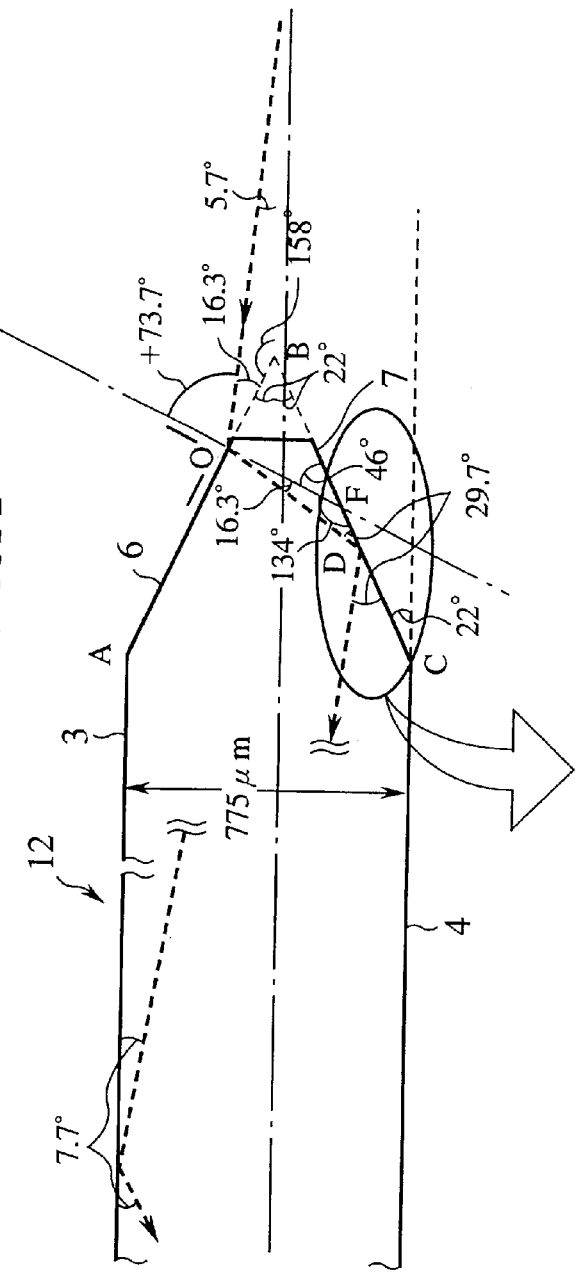
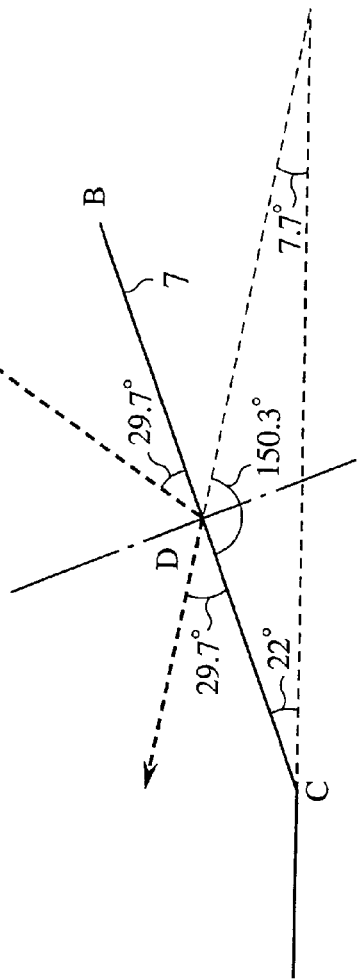
FIG. 20A
FIG. 20B

SURFACE STATE MONITORING METHOD AND APPARATUS

BACKGROUND OF THE INVENTION

The present invention relates to a surface state monitoring method and apparatus for performing in-situ monitoring of surface states of semiconductor substrates by infrared spectroscopy at fabrication sites of semiconductor devices.

Various requirements at fabrication sites of semiconductor devices require surface states of the semiconductor substrates being accurately grasped.

To give an example, in the field of semiconductor integrated circuits of memory devices, such as DRAM (Dynamic Random Access Memory), etc., and of logic devices, to form a gate insulation film having dielectric breakdown voltage of a required value, it is very important that surface states of a semiconductor substrate are administered. As a device has higher integration, the gate insulation film at the time of the fabrication of the device is made thinner, and the device has a design that the function for insulating an electric field (about $4 \times 10^6$ V/cm) of a MOS (Metal Oxide Semiconductor) FET (Field Effect Transistor) in operation has a small margin. Generally, a gate insulation film is formed by thermal oxidation. In forming a gate insulation film by thermal oxidation, in a case of surface contamination, as of metal contamination, chemical contamination, organic contamination or others is present, there is a risk that dielectric breakdown of the formed gate insulation film may be induced. It is known that organic contaminants stayed on the substrate surfaces after the gate insulation film has been formed results in insulation deterioration.

Plasma etching is widely used in steps of patterning device structures. In the plasma etching process, to set optimum plasma etching conditions and to detect the end point of the plasma etching, it is very effective to know adsorption states, chemical bonding states, structures and thicknesses of reaction layers, etc. of surface states of semiconductor wafers. The plasma etching process is determined by dynamic balance in adsorption, reaction and elimination processes between influxes of radical ions, etc. fed in gas phase and outfluxes from semiconductor substrate surfaces.

Recently, semiconductor devices have elements increasingly micronized, and are made increasingly three dimensional. This makes it difficult for cleaning solutions to intrude into micronized regions or steep steps or to be replaced there. In consideration of future further micronization, dry cleaning is noted. For example, to remove organic contaminants staying on silicon substrates reaction with ozone or oxygen excited by UV radiation is effective. Oxygen molecules are dissolved to oxygen atoms by light of a below 242 nm wavelength. The organic contaminants are oxidized by the oxygen atoms and solved into $H_2O$, $O_2$, CO, $CO_2$, etc. of high vapor pressures. Organic bonds, such as C—C, C—H, C—O, etc. can be dissolved by UV radiation. Thus, knowing surface states of semiconductor substrates is very important also to control parameters for the dry cleaning, such as an optimum amount of radiation, wavelength, oxygen amount, etc.

Native oxide films formed on the surfaces of silicon substrates are not usable in devices because their thickness cannot be controlled. Accordingly, it is preferable that when a device is fabricated on a silicon substrate, native oxide film on the silicon substrate is removed, and silicon bonds on the surfaces are terminated with hydrogen to stabilize the surfaces of the silicon substrate. This is because hydrogen can be eliminated at a relatively low temperature of about 500° C., and the termination with hydrogen relatively little affects the following processes. Most of silicon atoms on the surfaces of a silicon substrate subjected to UV ozone cleaning and hydrogen fluoride etching are terminated with hydrogen, and Si=$H_2$ and Si—H are formed. Accordingly, if a state of the termination with hydrogen on silicon substrate surfaces, temperature dependency of the elimination of terminating hydrogen can be monitored, the silicon substrate surfaces at the start of semiconductor processing can be kept in a suitable state. Higher quality and higher yields can be expected.

Thus, it is very important to know a surface state of a semiconductor substrate in a fabrication process of a semiconductor device, and various monitoring methods and apparatuses have been proposed and locally practiced.

Means for monitoring a surface state of a semiconductor substrate by internal multiple reflection of infrared radiation is provided by, e.g., FT-IR (Fourier-transform spectroscopy) apparatus or the special use marketed by Perkin-Elmer Co., U.S.A. For wider applications of the means Graseby Specac Limited, for example, markets various accessories.

In the conventional surface state monitoring method using this means, as exemplified in FIG. 41A, a substrate-to-be-monitored 102 is cut into, e.g., a 40 mm×10 mm strip, and infrared radiation emitted from an infrared radiation source 104 is passed through the substrate-to-be-monitored 102 to monitor states of the substrate surfaces. Otherwise, as exemplified in FIG. 41B, a substrate-to-be-monitored 102 has the end tapered, and infrared radiation is incident on the end surface of the substrate-to-be-monitored 102 to undergo multiple reflection inside the substrate, whereby a surface state of the substrate is monitored. Otherwise, as exemplified in FIG. 41C, infrared radiation is incident on a substrate-to-be-monitored via a prism 106 positioned above the substrate to undergo multiple reflection inside the substrate, whereby a surface state of the substrate is monitored.

The basic principle of monitoring a surface state of a substrate by applying infrared radiation to a substrate to cause the infrared radiation to undergo multiple reflection inside the substrate is that spectra of frequency components of evanescent waves oozing when light reflects on the substrate surfaces are resonance-absorbed when they agree with molecular vibrational frequencies of organic contaminants on the substrate surfaces are measured, whereby kinds and amounts of the organic contaminants can be determined. The basic principle also has a function that information of organic contaminants on substrate surfaces is gradually made more exact. A signal vs. noise ratio (S/N ratio) is also improved.

However, these monitoring methods needs cutting a substrate-to-be-monitored into strips, additionally machining a substrate-to-be-monitored, or disposing a prism above a substrate-to-be-monitored. These monitoring methods have not been usable in the in-situ monitoring at site of fabricating semiconductor devices.

Methods of monitoring organic contaminants on semiconductor substrates are known thermal desorption GC/MS (Gas Chromatography/Mass Spectroscopy), APIMS (Atmospheric Pressure Ionization Mass Spectroscopy), TDS (Thermal Desorption Spectroscopy), etc. However, these methods are not suitable to be used in in-situ monitoring at site of fabricating semiconductors for reasons that these methods cannot directly observe large wafers of, e.g., above 300 mm-diameters which are expected to be developed, and need vacuum ambient atmosphere, and have low throughputs, and other reasons.

As described above, the above-described conventional surface state monitoring methods are not usable in the in-situ monitoring at site of fabricating semiconductor devices because the monitoring by these method is destructive, or these methods are not suitable for monitoring large semiconductor wafers. Surface state monitoring methods and apparatuses which permit the in-situ monitoring of substrate surfaces at site of fabricating semiconductor devices, and permit large wafers to be monitored have been expected.

SUMMARY OF THE INVENTION

An object of the present invention is to provide a surface state monitoring method and apparatus which enable, at the site of fabricating a semiconductor device, in-situ monitoring of surface states of a substrate-to-be-monitored by infrared radiation spectroscopy of internal multiple reflection.

The above-described object is achieved by a surface state monitoring apparatus comprising: a first infrared radiation condensing means for condensing infrared radiation emitted by an infrared radiation source on an outer peripheral part of a substrate-to-be-monitored and introducing the infrared radiation into the substrate-to-be-monitored; an incident angle control means for controlling an incident angle of the infrared radiation condensed by the first infrared radiation condensing means, which enters the substrate-to-be-monitored to be fixed to a prescribed value or to be variable; a second infrared radiation condensing means for condensing the infrared radiation which has undergone multiple reflection in the substrate-to-be-monitored and exits the substrate-to-be-monitored; an infrared radiation detecting means for detecting the infrared radiation condensed by the second infrared radiation condensing means; and an infrared radiation analyzing means for analyzing the infrared radiation detected by the infrared radiation detecting means to measure contaminants staying on the surfaces of the substrate-to-be-monitored. The surface state monitoring apparatus having this constitution enables a substrate-to-be-monitored to be monitored without being additionally processed for the monitoring and makes it unnecessary to cause infrared radiation to enter the substrate-to-be-monitored via a prism, etc. disposed above the substrate-to-be-monitored. The surface state monitoring apparatus is used as an apparatus for in-situ monitoring surface states of a substrate-to-be-monitored at the site of its fabrication by infrared spectroscopy.

In the above-described surface state monitoring apparatus it is possible that the incident angle control means controls an incident angle of the infrared radiation entering the substrate-to-be-monitored so that a reflection angle of the infrared radiation inside the substrate-to-be-monitored is below a total reflection critical angle.

In the above-described surface state monitoring apparatus it is possible that the incident angle control means controls an incident angle of the infrared radiation entering the substrate-to-be-monitored so that an energy reflectivity of the infrared radiation at the time of entering the substrate-to-be-monitored is below a prescribed value In the above-described surface state monitoring apparatus it is possible that the infrared radiation analyzing means identifies the contaminants, based on a spectroscopic result given by Fourier transform spectroscopy.

In the above-described surface state monitoring apparatus it is possible that the infrared radiation analyzing means identifies the contaminants, based on a spectroscopic result given by infrared spectroscopy using a diffraction grating.

In the above-described surface state monitoring apparatus it is possible that the substrate-to-be-monitored has a pair of declined parts on outer peripheral parts, which are formed by chamfering the edges defined by a pair of surfaces of the substrate-to-be-monitored and the outer peripheral surface thereof, and the first infrared radiation condensing means condenses the infrared radiation on one or both of the pair of the declined parts of the substrate-to-be-monitored. Infrared radiation is introduced into a substrate-to-be-monitored through the declined parts formed in advance, so that infrared radiation can be introduced with high efficiency into the substrate-to-be-monitored without additionally processing the substrate-to-be-monitored. Infrared radiation is incident on both of the declined parts of a pair, whereby higher detection sensitivity can be obtained.

In the above-described surface state monitoring apparatus it is possible that the apparatus further comprises: a substrate mount including a position control mechanism for supporting the substrate-to-be-monitored and adjusting a position of the infrared radiation incident on the substrate-to-be-monitored, and a rotation mechanism for rotating the substrate-to-be-monitored. The substrate mount having this constitution makes the alignment of a substrate-to-be-monitored possible. The monitoring is repeated with the substrate-to-be-monitored being rotated. Surface states can be easily monitored all over the substrate surfaces.

In the above-described surface state monitoring apparatus it is possible that the first infrared radiation condensing means condenses the infrared radiation emitted by the infrared radiation source to an elliptical focus or a circular focus along an outer periphery of the substrate-to-be-monitored. Infrared radiation is condensed in an elliptical shape along an outer periphery of a substrate-to-be-monitored, whereby the infrared radiation can be used with higher use efficiency. Infrared radiation can be condensed into a circular shape to introduce the infrared radiation into a substrate-to-be-monitored but with a little lower use efficiency in comparison with that of the case that infrared radiation is condensed into the elliptical shape.

In the above-described surface state monitoring apparatus it is possible that the first infrared condensing means includes a spherical mirror, and an elliptical mirror positioned so as to position one focus of the elliptical mirror at a focus of the spherical mirror; the infrared radiation source is positioned at said one focus of the elliptical mirror; and the first infrared radiation condensing means condenses the infrared radiation emitted by the infrared radiation source to the other focus of the elliptical mirror.

In the above-described surface state monitoring apparatus it is possible that the second infrared radiation condensing means includes a spherical mirror, and an elliptical mirror positioned so as to position one focus of the elliptical mirror at a focus of the spherical mirror; the substrate-to-be-monitored is positioned so that an exit end surface of the substrate-to-be-monitored through which the infrared radiation exits is positioned at said one focus of the elliptical mirror; and the second infrared radiation condensing means condenses the infrared radiation exiting the substrate-to-be-monitored to the other focus of the elliptical mirror.

In the above-described surface state monitoring apparatus it is possible that the second infrared radiation condensing means includes a pair of reflecting mirrors which are opposed to each other with a gap therebetween on a side of the substrate-to-be-monitored being smaller than a gap therebetween on a side of the infrared radiation detecting means.

In the above-described surface state monitoring apparatus it is possible that the apparatus further comprises: a reflecting mirror disposed on an end surface of the substrate-to-be-monitored opposed to the end surface thereof on which the infrared radiation is incident, the reflecting mirror reflecting the infrared radiation exiting the substrate-to-be-monitored and introducing the infrared radiation again into the substrate-to-be-monitored. An optical path of infrared radiation propagating in a substrate-to-be-monitored can be long, so that higher detection sensitivity can be obtained.

In the above-described surface state monitoring apparatus it is possible that the substrate-to-be-monitored is a substrate having a pair of substantially parallel surfaces polished.

In the above-described surface state monitoring apparatus it is possible that the infrared radiation source includes a light source for emitting infrared radiation or near-infrared radiation, and an optical system for transforming light emitted by the light source into substantially parallel rays.

In the above-described surface state monitoring apparatus it is preferable that the substrate-to-be-monitored is a substrate which allows the infrared radiation to reflect more than 300 times in the substrate-to-be-monitored.

In the above-described surface state monitoring apparatus it is preferable that the substrate-to-be-monitored is monitored before being subjected to certain processing, after being subjected to certain processing or in certain processing.

The above-described object is also achieved by a surface state monitoring apparatus comprising: a first infrared radiation condenser for condensing infrared radiation emitted by an infrared radiation source on an outer peripheral part of a substrate-to-be-monitored and introducing the infrared radiation into the substrate-to-be-monitored; an incident angle controller for controlling an incident angle of the infrared radiation condensed by the first infrared radiation condensing means, which enters the substrate-to-be-monitored to be fixed to a prescribed value or to be variable; a second infrared radiation condenser for condensing the infrared radiation which has undergone multiple reflection in the substrate-to-be-monitored and exits the substrate-to-be-monitored; an infrared radiation detector for detecting the infrared radiation condensed by the second infrared radiation condensing means; and an infrared radiation analyzer for analyzing the infrared radiation detected by the infrared radiation detecting means to measure contaminants staying on the surfaces of the substrate-to-be-monitored.

The above-described object is also achieved by a surface state monitoring method comprising: condensing infrared radiation to an outer peripheral part of the substrate-to-be-monitored with an incident angle of the infrared radiation fixed to a required value or changed to introduce the infrared radiation into the substrate-to-be-monitored through the outer peripheral part; detecting the infrared radiation which has undergone internal multiple reflection in the substrate-to-be-monitored and exited the substrate-to-be-monitored; and analyzing the detected infrared radiation to measure contaminants staying on the surfaces of the substrate-to-be-monitored. The surface state monitoring method enables a substrate-to-be-monitored to be monitored without being additionally processed for the monitoring and makes it unnecessary to cause infrared radiation to enter the substrate-to-be-monitored via a prism, etc., disposed above the substrate-to-be-monitored. The surface state monitoring method makes it possible to in-situ monitor surface states of a semiconductor substrate at the site of its fabrication by infrared spectroscopy.

The above-described object is also achieved by a surface state monitoring method comprising: condensing infrared radiation to an outer peripheral part of a substrate-to-be-monitored, scanning incident angles in a prescribed range to introduce the infrared radiation into the substrate-to-be-monitored through the outer peripheral part; detecting the infrared radiation which has undergone internal multiple reflection in the substrate-to-be-monitored and exited the substrate-to-be-monitored; and analyzing the detected infrared radiation to measure contaminants staying on the surfaces of the substrate-to-be-monitored. The surface state monitoring method enables a substrate-to-be-monitored to be monitored without being additionally processed for the monitoring and makes it unnecessary to cause infrared. radiation to enter the substrate-to-be-monitored via a prism, etc. disposed above the substrate-to-be-monitored. The surface state monitoring apparatus is used as an apparatus for in-situ monitoring surface states of a substrate-to-be-monitored at the site of its fabrication by infrared spectroscopy. Incident angles of infrared radiation are scanned, whereby a region of a substrate-to-be-monitored along an infrared radiation optical path can be continuously detected. Higher detection sensitivity can be obtained.

In the above-described surface state monitoring method it is possible that the infrared radiation which has exited the substrate-to-be-monitored is subjected to Fourier transform spectroscopy, and the contaminants are identified based on a result of the spectroscopy.

In the above-described surface state monitoring method it is possible that the infrared radiation which has exited the substrate-to-be-monitored is subjected to the spectroscopy by using a diffraction grating, and the contaminants are identified based on a result of the spectroscopy.

The above-described object is also achieved by a surface state monitoring method comprising: condensing infrared radiation to an outer peripheral part of a substrate-to-be-monitored with an incident angle fixed to a prescribed value or changed to introduce the infrared radiation into the substrate-to-be-monitored through the outer peripheral part; detecting the infrared radiation which has undergone internal multiple reflection in the substrate-to-be-monitored and exited the substrate-to-be-monitored; and comparing an intensity of the detected infrared radiation with a reference intensity, and it is judged whether the substrate-to-be-monitored is good or not, based on a result of the comparison. Surface states of a substrate-to-be-monitored are thus monitored, whereby the surface states can be in-situ monitored at the site of its fabrication without additionally processing the substrate for the monitoring, causing infrared radiation into the substrate-to-be-monitored without the use of a prism, etc., disposed above the substrate-to-be-monitored. By the simple constitution of the apparatus, it can be judged whether or not a substrate-to-be-monitored is good.

The above-described object is also achieved by a surface state monitoring method comprising: condensing infrared radiation to an outer peripheral part of a substrate-to-be-monitored with an incident angle fixed to a prescribed value or changed to introduce the infrared radiation into the substrate-to-be-monitored through the outer peripheral part; detecting selectively that of the infrared radiation having undergone internal multiple reflection in the substrate-to-be-monitored and exited the substrate-to-be-monitored, which is in a wavelength range corresponding to a molecular vibration of a specific contaminant; and computing an amount of the specific contaminant staying on the surfaces of the substrate-to-be-monitored, based on an intensity of the detected infrared radiation. Surface states of a substrate-to-be-monitored are thus monitored, whereby it is not necessary to additionally process the substrate-to-be-monitored for the monitoring and cause infrared radiation to enter the substrate-to-be-monitored via a prism, etc., disposed above the substrate-to-be-monitored. This enables surface states of a semiconductor substrate to be in-situ monitored at the site of its fabrication. Amounts of contaminants staying on the surfaces of a substrate-to-be-monitored can be measured without the use of an infrared spectroscope, which makes the apparatus constitution simple and inexpensive.

In the above-described surface state monitoring method it is possible that the incident angle of the infrared radiation incident on the substrate-to-be-monitored is controlled in a range in which a reflecting angle of the infrared radiation in the substrate-to-be-monitored is larger than 0° and not more than a total reflection critical angle. Loss of infrared radiation by the internal multiple reflection can be decreased.

In the above-described surface state monitoring method it is possible that an incident angle of the infrared radiation incident on the substrate-to-be-monitored is controlled in a range in which an energy reflectivity of the infrared radiation at the time of the infrared radiation entering the substrate-to-be-monitored is below a prescribed value. Use efficiency of the infrared radiation can be high.

In the above-described surface state monitoring method it is possible that the infrared radiation is caused to enter the substrate-to-be-monitored through one or both of a pair of declined parts on the outer peripheral part, which are formed by chamfering the edges defined by a pair of surfaces of the substrate-to-be-monitored and the outer peripheral surface thereof. Infrared radiation is introduced into a substrate-to-be-monitored through the declined parts formed in advance, so that infrared radiation can be introduced with high efficiency into the substrate-to-be-monitored without additionally processing the substrate-to-be-monitored. Infrared radiation is incident on both of the declined parts of a pair, whereby higher detection sensitivity can be obtained.

In the above-described surface state monitoring method it is possible that the infrared radiation which has entered the substrate-to-be-monitored is reciprocated in the substrate-to-be-monitored, exits the substrate-to-be-monitored through an end surface through which the infrared radiation has entered, and is detected. An optical path of the infrared radiation propagating in a substrate-to-be-monitored can be long. Higher detection sensitivity can be obtained.

In the above-described surface state monitoring method it is preferable that the substrate-to-be-monitored is a substrate having a pair of substantially parallel polished surfaces.

In the above-described surface state monitoring method it is possible that a position of a substrate mount for supporting the substrate-to-be-monitored is controlled so that an amount of the infrared radiation which is detected after the infrared radiation has undergone internal multiple reflection in the substrate-to-be-monitored is maximum.

In the above-described surface state monitoring method it is possible that the substrate-to-be-monitored is monitored several times, being rotated to monitor the surfaces of the substrate-to-be-monitored substantially all over the surfaces of the substrate-to-be-monitored.

In the above-described surface state monitoring method it is possible that the infrared radiation is condensed to an elliptical focus or a circular focus to be incident on the substrate-to-be-monitored. Infrared radiation is condensed to an elliptical shape along the outer periphery of a substrate-to-be-monitored, whereby the infrared radiation can be used with higher use efficiency. Infrared radiation can be introduced into a substrate-to-be-monitored by being condensed into a circular shape but with a little lower use efficiency in comparison with that of the case that infrared radiation is condensed into the elliptical shape.

BRIEF DESCRIPTION OF THE DRAWINGS

FIGS. 17A and 17B are schematic sectional views of a substrate-to-be-monitored, which show relationships between the substrate-to-be-monitored and infrared radiation in the surface state monitoring method and apparatus according to a third embodiment of the present invention.

FIGS. 20A and 20B are schematic sectional views of a state in which an incident angle of infrared radiation is not proper.

DETAILED DESCRIPTION OF THE INVENTION

[A First Embodiment]

The surface state monitoring method and apparatus according to a first embodiment of the present invention will be explained with reference to FIGS. 1 to 15.

(1) General Structure of the Apparatus

The surface state monitoring apparatus according to the present embodiment will be explained with reference to FIGS. 1 to 10.

Figure 1:
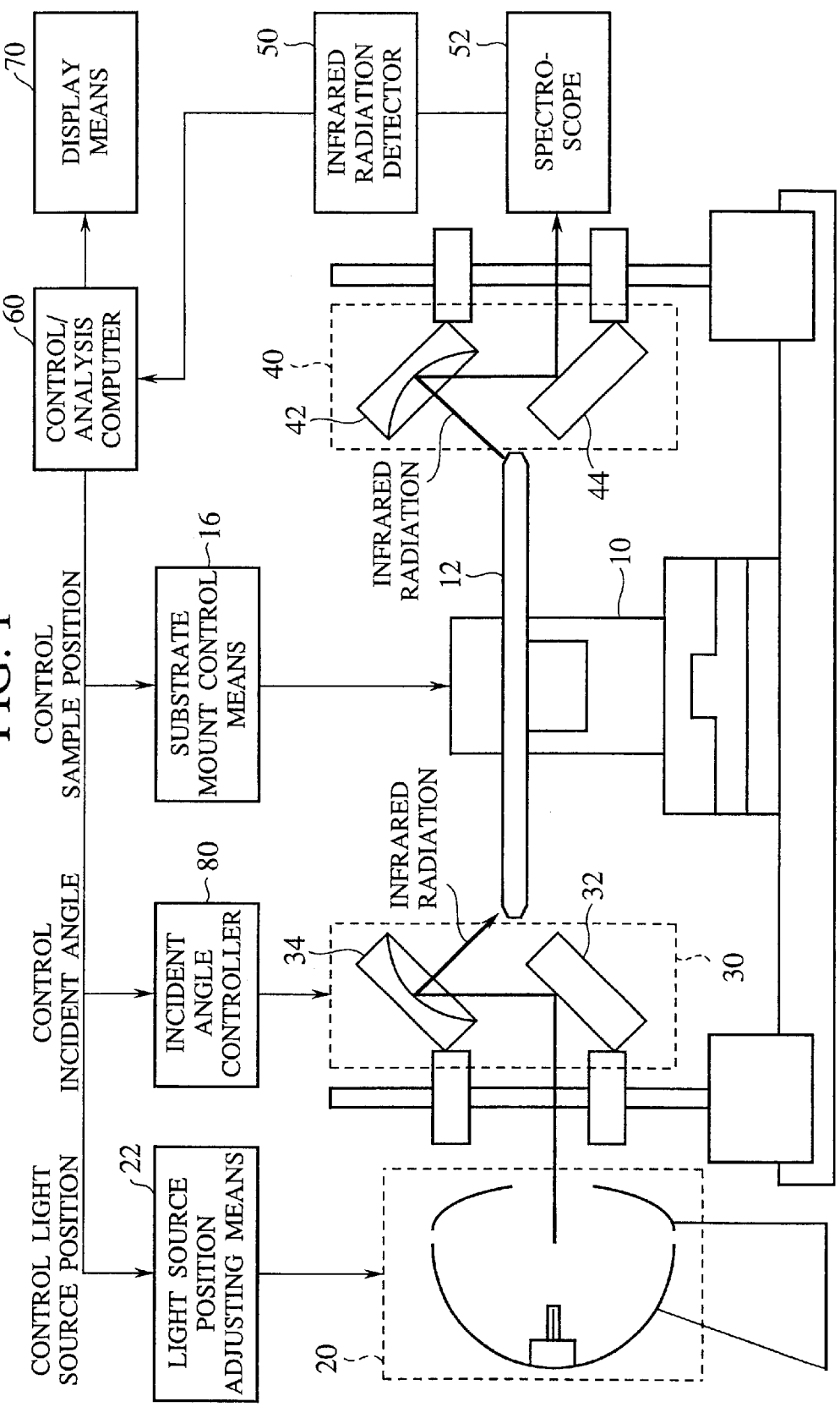
FIG. 1 is a diagrammatic sectional view of the surface state monitoring apparatus according to a first embodiment of the present invention.
Figure 2:
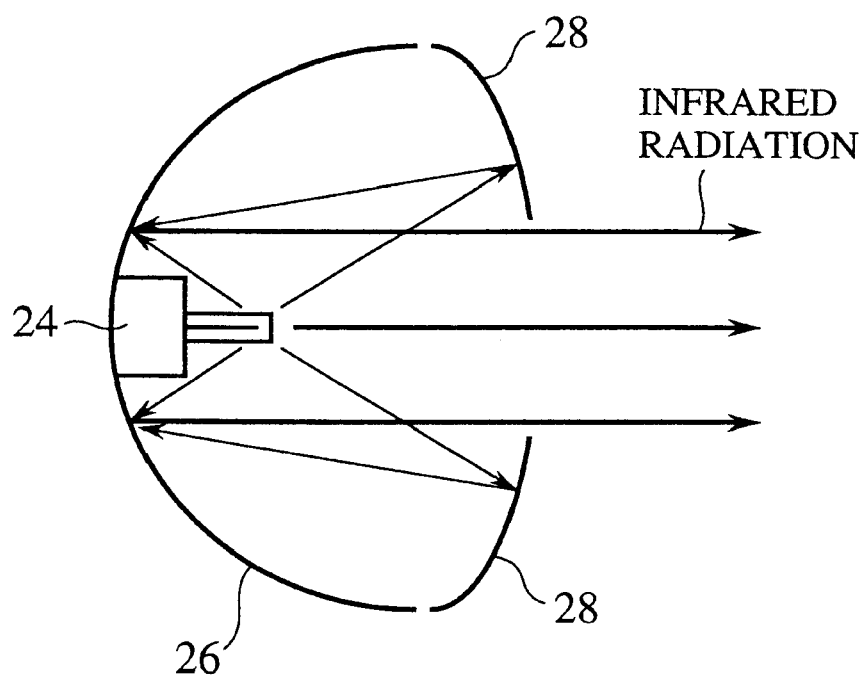
FIG. 2 is a diagrammatic sectional view of the infrared radiation source of the surface state monitoring apparatus according to the first and a second embodiments of the present invention.
Figure 3A:
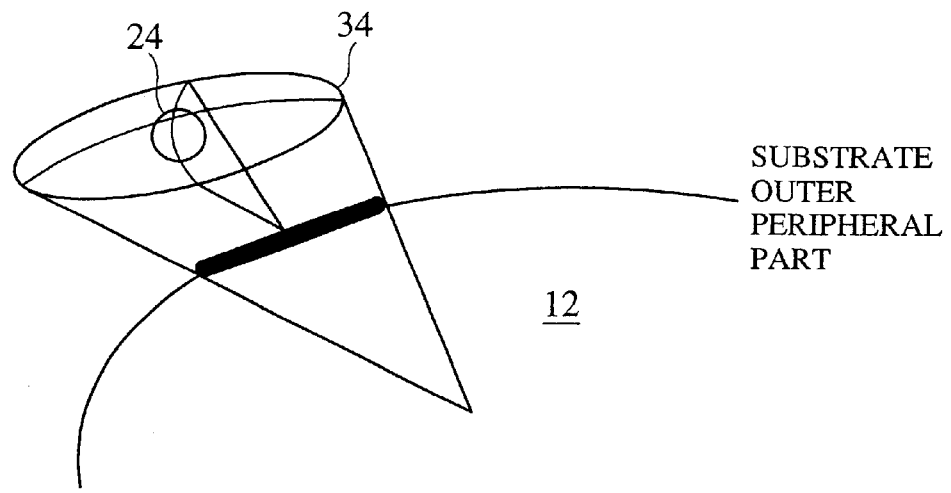
FIGS. 3A and 3B are views explaining a method of condensing infrared radiation along the outer periphery of a substrate-to-be-monitored by the use of a concave mirror.
Figure 3B:
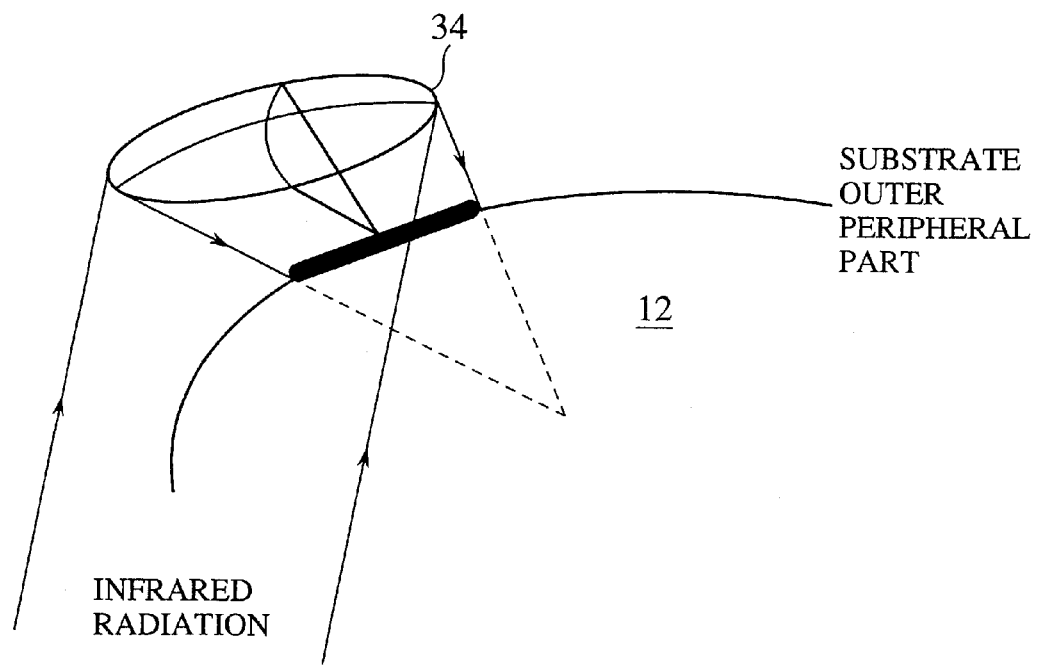
Figure 4A:
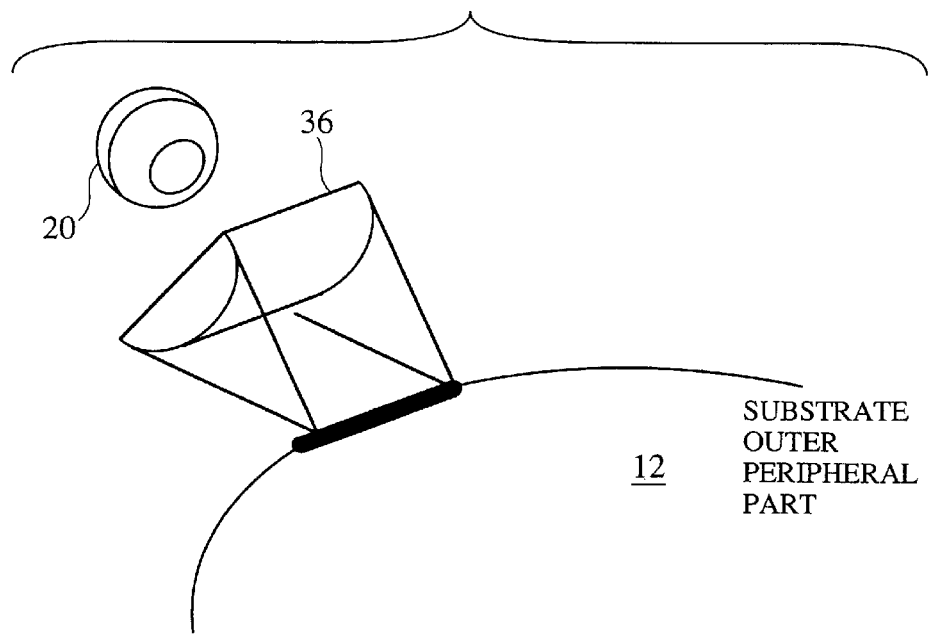
FIGS. 4A and 4B are views explaining a method of condensing infrared radiation along the outer periphery of a substrate-to-be-monitored by the use of a cylindrical lens or a slit.
Figure 4B:
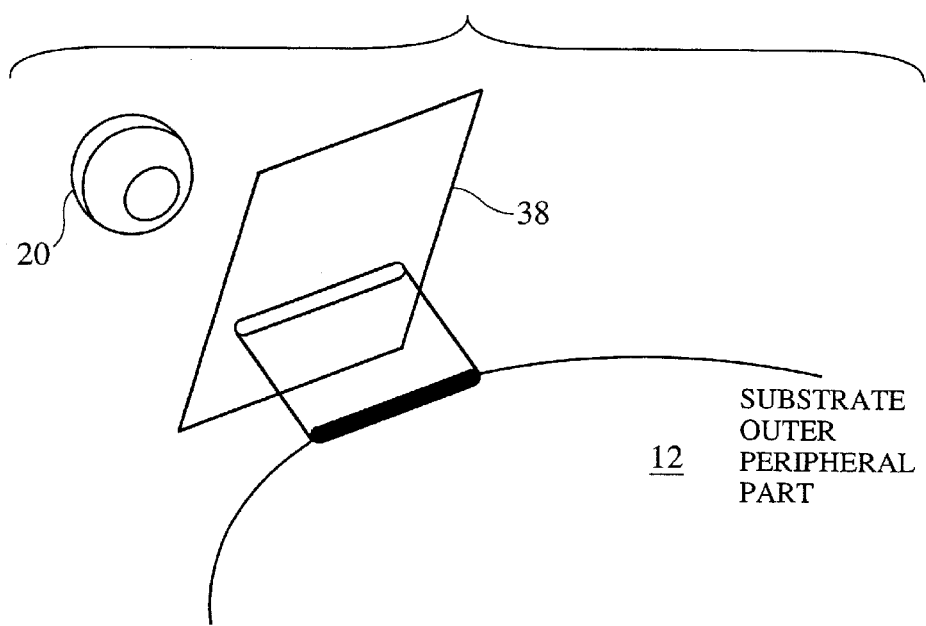
Figure 5:
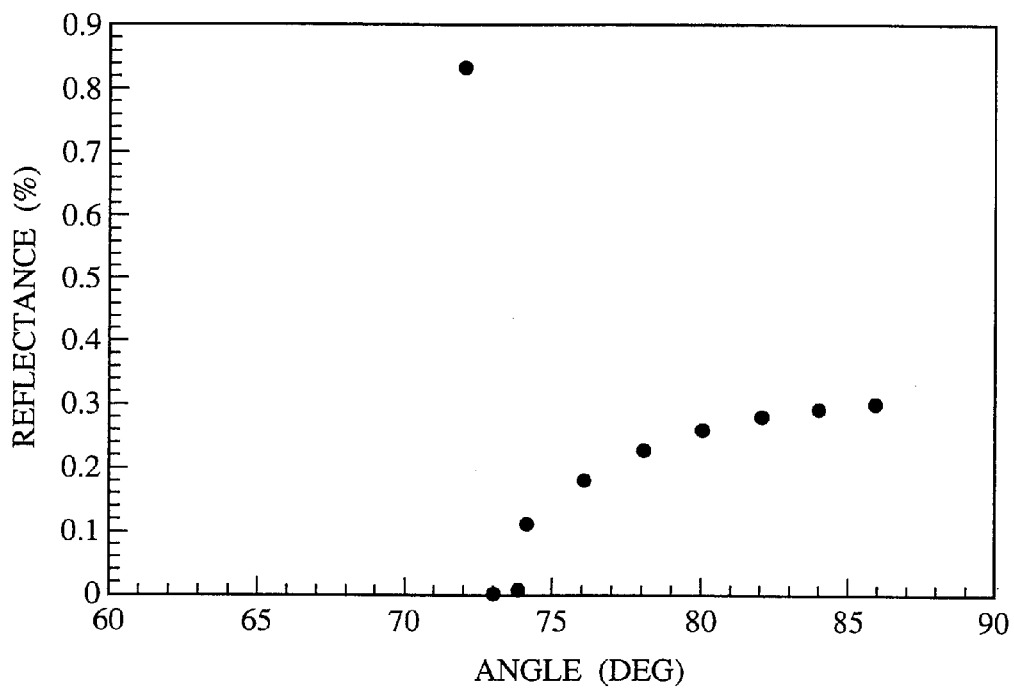
FIG. 5 is a graph of incident angle dependency of energy reflectivity at the time of infrared radiation exiting a silicon substrate into air.
Figure 6:
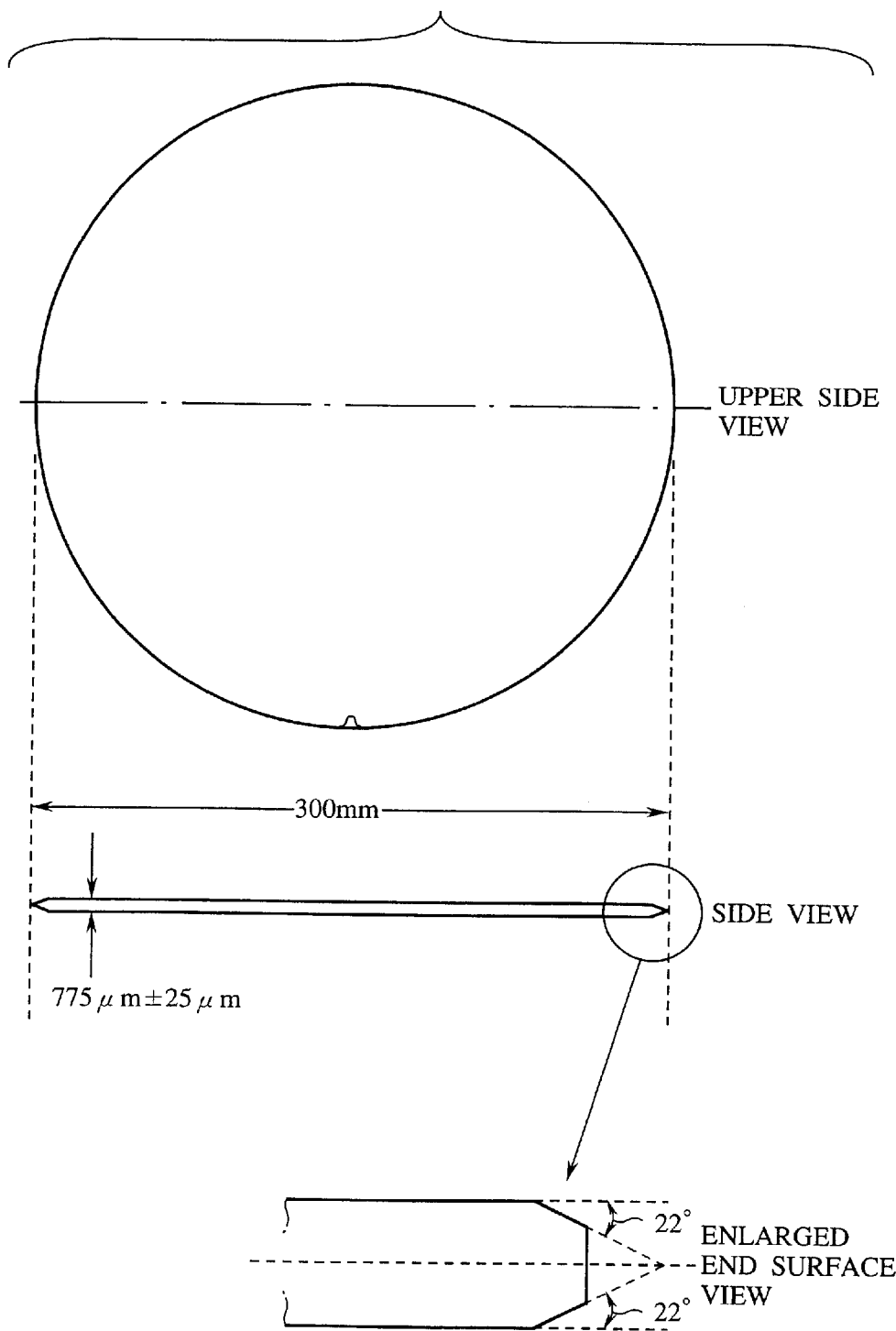
FIG. 6 is a view showing the configuration of a 300 mm wafer in accordance with SEMI standard specifications.
Figure 7:
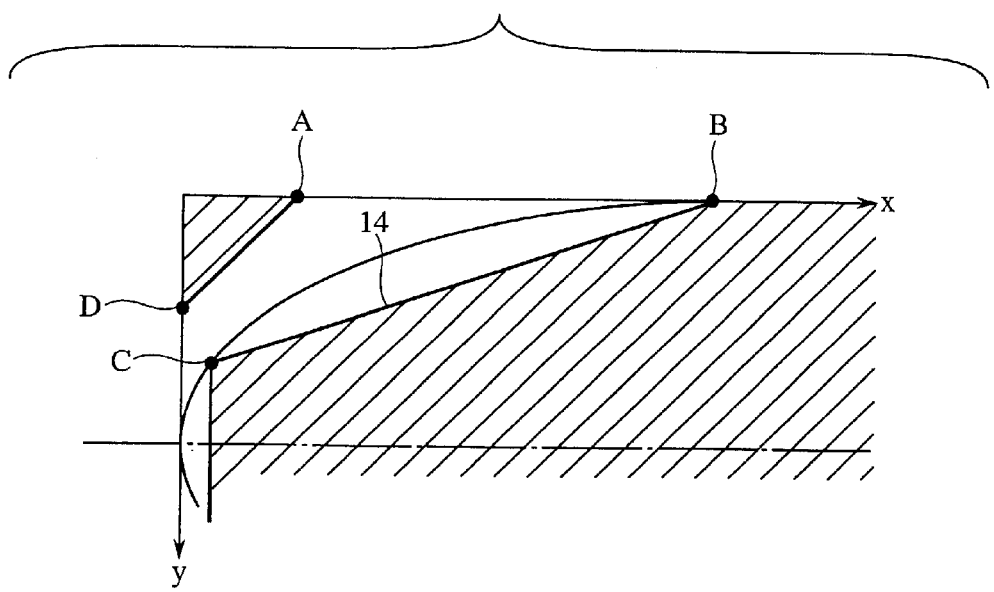
FIG. 7 is a view of a shape of a peripheral edge of a 300 mm wafer in accordance with SEMI standard specifications.
Figure 8:
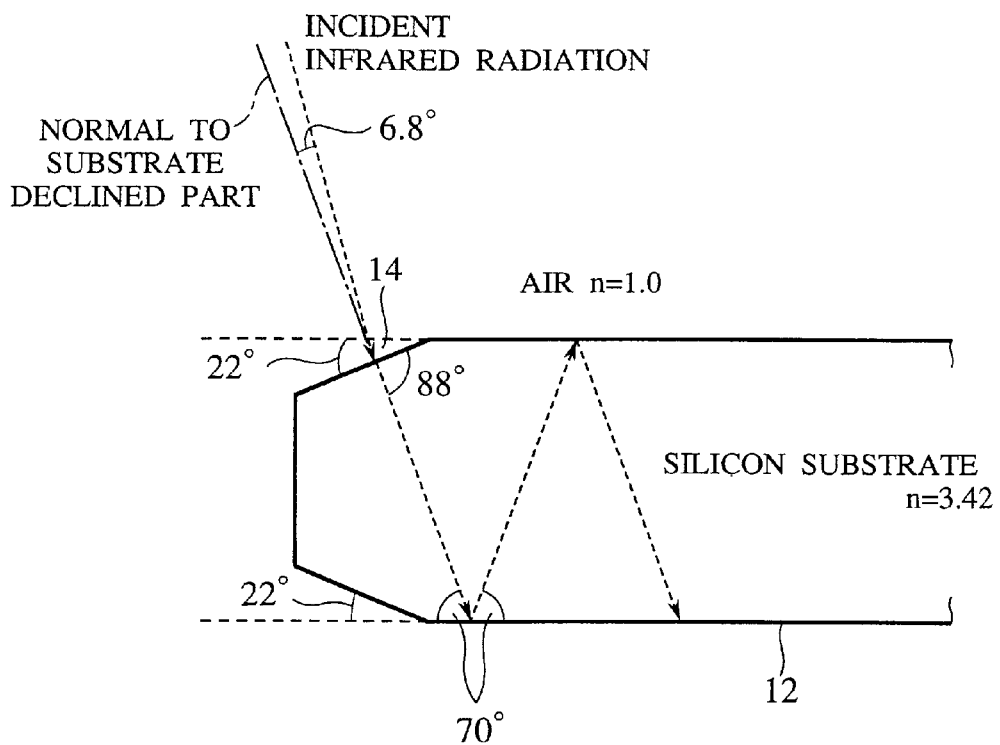
FIG. 8 is a view explaining a method of setting an incident angle of infrared radiation at which the infrared radiation is incident on a substrate-to-be-monitored used in the surface state monitoring method and apparatus according to a first and a second embodiments of the present invention.
Figure 9:
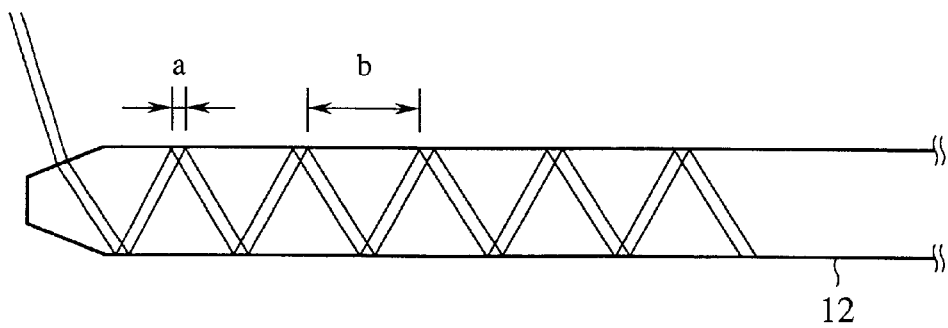
FIG. 9 is a conceptional view explaining a case with an incident angle of infrared radiation fixed.
Figure 10:
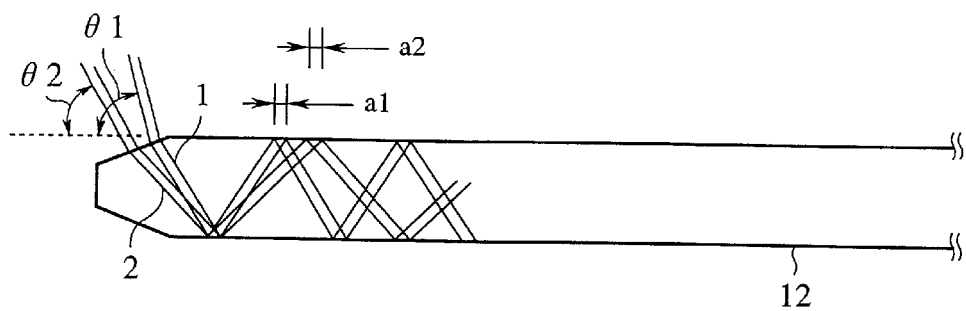
FIG. 10 is a conceptional view explaining advantages produced by scanning incident angles of infrared radiation.

FIG. 1 is a diagrammatic view of the surface state monitoring apparatus according to the present embodiment. FIG. 2 is a diagrammatic sectional view of an infrared radiation source of the surface state monitoring apparatus according to the present embodiment. FIGS. 3A and 3B are views explaining a method for condensing infrared radiation by a concave mirror along the outer periphery of a substrate-to-be-monitored. FIGS. 4A and 4B are views explaining a method for condensing infrared radiation by a cylindrical lens or a slit along the outer periphery of a substrate-to-be-monitored. FIG. 5 is a graph of incident angle dependency of energy reflectivities at the time that the infrared radiation is emitted from the interior of a silicon substrate into air. FIGS. 6 and 7 are views of a configuration of a 300 mm wafer in accordance with SEMI standard specifications. FIG. 8 is a view explaining a method for setting an incident angle of infrared radiation on a substrate-to-be-monitored, which is used in the surface state monitoring method an apparatus according to the present embodiment. FIG. 9 is a conceptual view explaining disadvantages of a case that a fixed incident angle of infrared radiation is used. FIG. 10 is a conceptual view explaining advantages of a case that scanning incident angles of infrared radiation are used.

As shown in FIG. 1, the surface state monitoring apparatus according to the present embodiment comprises a substrate mount 10 on which a substrate-to-be-monitored 12 is to be mounted; an infrared radiation source 20 which emits infrared radiation; infrared radiation condensing means 30 which converges infrared radiation emitted by the infrared radiation source 20 into a prescribed shape to apply the infrared radiation to the substrate-to-be-monitored 12; infrared radiation condensing means 40 for condensing infrared radiation which has undergone multiple reflection inside the substrate-to-be-monitored 12 and passed through the substrate-to-be-monitored 12, to apply the infrared radiation to an infrared radiation detector 50; and the infrared radiation detector 50 which detects the infrared radiation from the infrared radiation condensing means 40.

The infrared radiation source 20 is connected to a control/analysis computer 60 through infrared radiation source position adjusting means 22. The substrate mount 10 is connected to the control/analysis computer 60 through a substrate mount control means 16. Thus, infrared radiation is applied to a prescribed part of the substrate-to-be-monitored 12 placed on the substrate mount 10.

The infrared radiation condensing means 30 is connected to the control/analysis computer 60 through an incident angle controller 80. Thus, an incident angle of the infrared radiation applied to the substrate-to-be-monitored 12 by the infrared radiation condensing means 30 is set at a prescribed value, changed or scanned.

Infrared radiation converged by the infrared radiation condensing means 40 is led to the infrared radiation detector 50 through a spectroscope 52. The infrared radiation detector 50 is connected to the control/analysis computer 60, so that a surface state of the substrate-to-be-monitored 12 can be analyzed based on detected signals given by the infrared radiation detector 50. Display means 70 is connected to the control/analysis computer 60, so that the display means 70 displays results of analysis of the detected signals made by the control/analysis computer 60, and database access results.

Means for removing carbon dioxide ($CO_2$) in air, whose spectrum overlaps a spectrum of an organic molecule (not shown) is inserted in an optical path of the infrared radiation detector 50 and an optical path of the monitored infrared radiation.

The surface state monitoring apparatus according to the present embodiment is the same as the conventional apparatuses in the infrared radiation detector, the means for leading the infrared radiation to the infrared radiation detector, a database for identifying substance species, based on detected results given by the infrared radiation detector, and the means for removing carbon dioxide in air whose spectrum overlap a spectrum of an organic molecule, which is inserted as assistant means in the optical path of the infrared radiation detector and an optical path of the monitored infrared radiation.

The surface state monitoring apparatus according to the present embodiment is different from the conventional apparatuses in that the former includes the infrared radiation source 20 for emitting infrared radiation; the optical system (the infrared radiation condensing means 30) for effectively condensing the infrared radiation into a shape conforming to an outer periphery of a substrate-to-be-monitored 12 or into one point on the outer periphery of the substrate-to-be-monitored 12 and applying the infrared radiation to the substrate-to-be-monitored 12; and the optical system (the infrared radiation condensing means 40) for again condensing the infrared radiation which has undergone multiple reflection inside the substrate and exited the substrate at a point symmetrical with the incidence point, and leading the infrared radiation to the infrared radiation detector.

The optical system is thus constituted, whereby organic contamination and chemical contamination on a substrate-to-be-monitored 12 can be monitored without performing additional processing, such as chemical etching, on the substrate or without passing infrared radiation into the substrate through the prism disposed above the substrate-to-be-monitored 12.

The control system (the incident angle controller 80) for controlling an incident angle of infrared radiation applied to a substrate-to-be-monitored 12 is disposed as a subordinate function, whereby drastically improved sensitivity of detecting organic contamination and chemical contamination on the substrate-to-be-monitored 12 can be obtained.

The respective constituent members of the surface state monitoring apparatus according to the present embodiment will be separately detailed. It is possible that various constituent members of a third to an eighth embodiments which will be described later are applied with the surface state monitoring apparatus according to the present embodiment.

(a) Infrared Radiation Source 20

As exemplified in FIG. 2, the infrared radiation source 20 comprises a light source 24 for generating infrared radiation, a rear reflecting plate 26 and a front reflecting plate 28.

The light source 24 is provided by infrared radiation of a 2–25 μm band corresponding to molecular vibrations of organic molecules. For example, heat rays emitted by applying current to silicon carbide (SiC) as a filament may be used as the light source 24. The light source of SiC, such as an SiC Globar lamp or others, has characteristics of emitting infrared radiation of a 1.1–25 μm band and being usable naked in air without burning.

Infrared radiation is used as a light source for the monitoring because infrared radiation intrinsically has the energy level lower in comparison with x-rays, γ-rays, accelerated electron beams, accelerated ion beams, etc., so that when infrared radiation is applied to an object-to-be-monitored, the possibility of the infrared radiation damaging the object-to-be-monitored is very low. This is one reason why infrared radiation is selected as a probe beam source which does not damage delicate objects-to-be-monitored, such as very highly integrated semiconductor devices in their fabrication processes.

The most important reason for the use of infrared radiation is that frequency ranges of organic contaminants or chemical contaminants to be detected are substantially in the frequency range of infrared radiation.

The rear reflection plate 26 and the front reflection plate 28 function, as the members of the infrared radiation source, to improve efficiency of an effective infrared radiation amount with a constant current applied to. The rear reflection plate 26 and the front reflection plate 28 have the surfaces coated with a material which effectively reflects infrared radiation, e.g., aluminum or others.

The rear reflection plate 26 is constituted by a parabolic reflection plate and is disposed so that the infrared radiation source 24 is positioned at a focus of the paraboloid. Thus, infrared radiation emitted by the infrared radiation source 24 is transformed into substantially parallel rays.

The front reflection plate 28 is for prohibiting the generation of stray light unnecessary for the monitoring. The front reflection plate 28 as well as the rear reflection plate 26 is constituted by a parabolic reflection plate. The front reflection plate 28 has an exit window through which exits only infrared radiation necessary for the monitoring.

The front reflection plate 28 reflect infrared radiation unnecessary for the monitoring, whereby generation of stray light can be prevented. Infrared radiation reflected on the front reflection plate 28 is again reflected on the rear reflection plate 26, and some of the reflected infrared radiation is transformed into effective parallel rays, with a result of increase of effective infrared radiation.

Other examples of the rear reflection plate 26 and the front reflection plate 28 will be explained in a fourth embodiment which will be described later.

The infrared radiation source may be an explosion proof-infrared radiation source having the exit window for infrared radiation formed of an infrared radiation transmitting material. The infrared radiation source of this type is effective especially in a case that a combustible gas must be introduced into the monitoring system.

The front reflection plate 28 is not essential.

(b) Infrared Radiation Condensing Means 30

In the surface state monitoring apparatus according to the present embodiment infrared radiation is caused to enter a substrate-to-be-monitored 12 through a part of the outer periphery of the substrate-to-be-monitored 12. For this end, it is important for higher incidence efficiency of infrared radiation entering the substrate-to-be-monitored how to converge infrared radiation emitted by the infrared radiation source 20 to apply the infrared radiation to the substrate-to-be-monitored.

It is preferable that infrared radiation is converged to an elliptical shape along the outer periphery of a substrate-to-be-monitored. To converge infrared radiation into a elliptical focal shape an aberration of a lens system is intentionally used. An elongated focal shape can be formed by utilizing a coma aberration or distortion of a lens system. Here a concave mirror 34 having a larger focal distance in the X direction than that in the Y direction is assumed. An elliptical focal shape can be formed on the outer periphery of a substrate-to-be-monitored 12 by disposing the infrared radiation source 20 at the center of the concave mirror 34 (see FIG. 3A). When parallel rays are incident on the concave mirror 34 shown in FIG. 3A, reflected infrared radiation forms a focus in the longer axis (X direction)

below the substrate-to-be-monitored, and a focus in the shorter axis (Y direction) can be formed on the outer periphery of the substrate-to-be-monitored (see FIG. 3B).

The infrared radiation condensing means 30 of the present embodiment uses the latter principle. As shown in FIG. 1, the infrared radiation condensing means 30 comprises a reflection plate 32 and the concave mirror 34, whereby infrared radiation reflected on the reflection plate 32 is reflected on the concave mirror 34 tilted to the infrared radiation. The same effect can be attained. The means for forming an elliptical focal shape may be any.

A focal shape of infrared radiation is preferably elliptical but many be circular. The circular focal shape is a little inferior to an elliptical focal shape in incidence efficiency. To form a circular focal shape a convex lens, for example, may be used.

It is possible that infrared radiation is transformed to an elongated focal shape to be applied to a substrate-to-be-monitored 12. As exemplified in FIG. 4A, infrared radiation emitted by the infrared radiation source 20 may be converged by a cylindrical lens 36 or, as shown in FIG. 4B, may be passed through a slit to be applied to.

Other examples of the infrared condensing means 30 will be explained in a fifth embodiment which will be described later.

(c) Arrangement of the Optical System

In the surface state monitoring method according to the present embodiment, it is important to converge infrared radiation at one point on the outer periphery of a substrate-to-be-monitored 12, cause the infrared radiation which has entered the substrate-to-be-monitored to undergo internal multiple reflection, and again converge the infrared radiation which has exit at a point symmetrical to the incident point, so as to be guided to the infrared radiation detector 50. To this end, it is important how to cause the infrared radiation to efficiently enter the substrate-to-be-monitored.

Then, conditions for the multiple reflection of infrared radiation inside a substrate-to-be-monitored and conditions for causing infrared radiation to enter the substrate-to-be-monitored from the outside will be explained.

In the surface state monitoring apparatus according to the present embodiment infrared radiation is caused to undergo multiple reflection inside a substrate-to-be-monitored, detect molecular vibrations of organic contaminants or chemical contaminants, based on light exuded on the surfaces of the substrate-to-be-monitored to monitor surface states of the substrate-to-be-monitored. Accordingly, it is necessary that an incident angle of infrared radiation which enters a substrate-to-be-monitored is set that the infrared radiation undergoes multiple reflection inside the substrate-to-be-monitored 12.

Conditions for infrared radiation undergoes perfect reflection in a substrate-to-be-monitored are given by computing Snell's law and energy reflectivities. In a case that the substrate-to-be-monitored 12 is a silicon substrate, infrared radiation undergoes perfect reflection when infrared radiation forms angles of 0 to 72° (see FIG. 5). A trace of infrared radiation having an angle in this range is traced back, and an intersection between the end surface of the silicon substrate-to-be-monitored and the infrared radiation is an incidence point of the infrared radiation on the silicon substrate.

The surface state monitoring apparatus according to the present embodiment can in-situ monitor a substrate-to-be-monitored 12 without processing the substrate 12, and uses a processed configuration of an end surface of the substrate for the incidence of infrared radiation.

The configurations of the end surfaces of the semiconductor substrates are determined by SEMI (Semiconductor Equipment and Material International), and specifications of 300 mm silicon wafers which are to be used around 2001 have been provisionally decided.

A 300 mm silicon wafer decided by the SEMI standard specifications is as shown in FIG. 6. That is, a 300 mm silicon wafer is formed in a disc having a 300 mm-diameter and a 775 $\mu$m-thick and has the borders between a pair of surfaces and the outer peripheral surface chamfered. As shown in FIG. 7, the finished processed configuration of the wafer has an angle of about 22° formed by the line A–B and the line C–B. The region which is not hatched is an allowable range for configuration processing.

Both surfaces of the 300 mm silicon wafer in the finished processed configuration in accordance with the SEMI standard specifications are polished specular, and the wafer is usable as it is, for analysis methods using infrared radiation internal multiple reflection, to which specular finish of both surfaces is necessary.

Then, incident angle of infrared radiation will be explained by means of a 300 mm silicon wafer.

When it is assumed that an incident angle of infrared radiation propagating in the substrate is 70°, and a trace of the infrared radiation is traced back to set an incident point of the infrared radiation at an intersection of the infrared radiation and an end surface (the inclined portion 14 between B and C herein after called "a declined part" or "an end part") of the silicon substrate, as shown in FIG. 8, an angle formed by the declined part 14 and the infrared radiation is about 88°. Accordingly, when the angle is calculated back based on Snell's law with a refractive index of the silicon substrate of 3.42; a refractive index of air of 1.00; and an angle formed by a normal of the declined part 14 and infrared radiation of 2°, it is found that infrared radiation is incident at an angle of about 6.8° (about 74.8° to the flat surfaces of the substrate) to the normal of the declined part 14 so that the infrared radiation entering the silicon substrate undergo multiple reflection. At this time, an energy reflectivity at the incident point is as high as about 29.42%, but infrared radiation is applied in a radiation amount which compensate the high reflectivity. A method for setting an incident angle which can yield low energy reflectivity will be explained in a third embodiment which will be explained later.

An incident angle of infrared radiation incident on the declined part 14 can be decided by thus calculating back the incident angle, based on angles of multiple reflection in the substrate.

In cases of semiconductor substrates other than the silicon substrate and of end surface configurations different from the described above, incident angles of infrared radiation can be set by the same procedure. Infrared radiation may be incident on the declined part 14 of the front surface of the substrate or the declined part 14 of the back surface of the substrate.

An arrangement of the infrared radiation optical system will be explained in the third embodiment which will be explained later.

(d) Incident Angle Control System

The incident angle control system is for controlling an incident angle of infrared radiation incident on a substrate-to-be-monitored 12 is controlled to be a required value.

The incident angle control system mainly comprises an incident angle controller 80. The incident angle control system controls the infrared radiation condensing means 30 by a control/analysis computer 60 connected thereto through the incident angle controller 80 to thereby an incident angle of infrared radiation incident on a substrate-to-be-monitored 12. The infrared radiation condensing means 30 has, e.g., the concave mirror 34 in the form of a variable reflecting mirror, and a position angle of the variable reflecting mirror is changed by the incident angle controller 80, whereby the infrared radiation condensing means 30 is controlled.

The incident angle control system can be used roughly in two modes.

In a first mode, an incident angle of infrared radiation incident on a substrate-to-be-monitored 12 is set at a prescribed value.

In this mode, an incident angle of infrared radiation incident on the declined part 14 of the substrate-to-be-monitored is set so that a total reflection angle of the infrared radiation in the substrate-to-b-e-monitored 12 has a prescribed value. When a reflection angle of the infrared radiation in the substrate-to-be-monitored 12 changes, a reflection frequency in the substrate-to-be-monitored changes, and accordingly, there is risk that monitoring sensitivity, etc. may not be uniform. Setting an incident angle of infrared radiation at a prescribed value has an advantage that disuniformity of a monitoring sensitivity among substrates-to-be-monitored can be depressed.

In a second mode, an incident angle of infrared radiation incident on a substrate-to-be-monitored 12 is scanned in a prescribed range. This mode and advantages of this mode will be detailed.

In the above-described mode of positioning the infrared radiation optical system, an incident angle of infrared radiation incident on a substrate-to-be-monitored 12 is set at a prescribed value so that the infrared radiation incident on the declined part 14 of the substrate-to-be-monitored 12 undergoes multiple reflection in the substrate-to-be-monitored to probe surface states and exit at the end opposed to the incident part.

However, if an incident angle of infrared radiation is set constant, as shown in FIG. 9, the infrared radiation is incident on the region "a" but is not incident on the region "b". The infrared radiation detected after multi-reflection in the substrate-to-be-monitored 12 contains information of the region "a" but does not contain information of the region "b". For higher monitoring sensitivity, it is preferable that information including that of regions, such as the region "b", is also monitored.

In the second mode, the infrared radiation emitted by the infrared radiation source 20 is incident on a substrate-to-be-monitored 12 while incident angles of the infrared radiation are scanned by the incident angle controller 80, whereby high monitoring sensitivity can be obtained. This arrangement of the incident angle control system makes it possible that, as exemplified in FIG. 10, infrared radiation 1 incident at an incident angle θ1 undergoes total reflection on the back surface of the substrate-to-be-monitored 12 to enter into the region "a1" on the front surface. Infrared radiation 2 incident at an incident angle θ2 different from the incident angle θ1 undergoes total reflection on the back side of the substrate-to-be-monitored 12 to enter in the region "a2" on the front surface. Thus, an incident angle of the infrared radiation is continuously changed, whereby total reflection region in an optical path of the infrared radiation are made continuous. Thus, surface states of the substrate-to-be-monitored in the optical path can be analyzed with high sensitivity.

A scanning range of incident angles of the infrared radiation is set as exemplified below. However, it is preferable that an incident angle of the infrared radiation is suitably selected in accordance with a sensitivity and characteristics required for the monitoring.

For example, in a case that an incident angles is set in consideration that the monitoring is performed under conditions that the infrared radiation undergoes total reflection in a substrate-to-be-monitored 12, an incident angle of the infrared radiation is continuously changed so that an angle α formed by a flat surface of the substrate-to-be-monitored 12 and the infrared radiation in the substrate-to-be-monitored is set as follows.

Critical Angle≧α>0.

The total reflection critical angle of the silicon is about 72°.

In a case that, as in the third embodiment, which will be described later, an incident angle is set in consideration that an energy reflectivity of the infrared radiation at the incidence on a substrate-to-be-monitored 12 is, e.g., below about 2%, an incident angle of the infrared radiation is controlled so that an angle formed by a flat surface of the substrate-to-be-monitored 12 and the infrared radiation in the substrate-to-be-monitored is 46° to 56°, i.e., an incident angle of the infrared radiation to the declined part 14 of the substrate-to-be-monitored 12 is 68° to 78° (see Table 2).

The advantage of the second mode can be obtained, in addition to the case that incident angles are scanned in a prescribed range, in the case that an incident angle is continuously changed only in one direction and in the case that an incident angle is intermittently changed.

In a case that an incident angle can be controlled by the light source position adjusting means 22, the substrate mount control means 16 or other members, the incident angle control system for controlling the infrared radiation condensing means 30 is not essential. That is, such control system has the same function as the incident angle controller 80, whereby the same advantage produced by providing the incident angle controller 80 can be produced.

(e) Substrate Mount 10

When a substrate-to-be-monitored 12 is carried and placed on the substrate mount 10, it is not always that the substrate-to-be-monitored 12 is correctly positioned. Then, a substrate mount control means 16 for finely adjusting the substrate mount 10 in X-, Y- and Z-directions is connected to the substrate mount 10. The fine adjustment in the X-, Y-, and Z-directions is for optical axis alignment so that the infrared radiation is supplied in a maximum light amount to the infrared radiation detector 50.

An optimum point of a fine adjustment of the substrate mount 10 with a substrate-to-be-monitored 12 mounted on, in the X-, Y- and Z-directions is judged based on a point where a maximum light amount of the infrared radiation which has undergone multiple reflection in the substrate-to-be-monitored is detected, and can be automatically positioned. The positioning is performed by the control/analysis computer 60 connected to the substrate mount 10 through the substrate mount control means 16.

The substrate mount 10 has a rotation mechanism and can rotate a substrate-to-be-monitored 12 by the control/analysis computer 60 through the substrate mount control means 16. The substrate-to-be-monitored 12 is rotated, so that organic contaminates and chemical contaminates can be detected substantially all over the substrate.

(f) Infrared Radiation Condensing Means 40

The infrared radiation incident on a substrate-to-be-monitored exit at a position symmetrical to the incident point. Then, the infrared radiation condensing means 40 condenses the infrared radiation exiting the substrate-to-be-monitored 12 and guides the infrared radiation to the infrared radiation detector 50.

As exemplified in FIG. 1, the infrared radiation condensing means 40 comprises, e.g., a concave mirror 42 and a reflecting mirror 44. The infrared radiation condensing means 40 of this structure can condense the infrared radiation exiting the substrate-to-be-monitored 12 by the concave mirror 42 and guide the same to the infrared radiation detector 50 via the reflecting mirror 44.

A convex lens may be used in place of the concave mirror 42.

Other examples of the structure of the infrared radiation condensing means 40 will be described in a sixth and an eighth embodiments which will be described later.

(g) Infrared Radiation Detector 50 and Spectroscope 52.

The infrared radiation which has exited a substrate-to-be-monitored 12 is condensed by the infrared radiation condensing means 40 and guided to the infrared radiation detector 50 via the spectroscope 52.

The spectroscope 52 is of, e.g., an FT-IR apparatus which subjects infrared radiation to spectral diffraction by the mechanism of Fourier-transform spectroscopy by a double beam interferometer (Michelson interferometer). The infrared radiation detector 50 is a detector of, e.g., an FT-IR apparatus, and can be provided by a nitrogen-cooling infrared radiation detector of, e.g., InSb.

As described in the basic principle that infrared radiation is incident on a substrate-to-be-monitored 12 and undergoes multiple reflection inside the substrate to thereby monitor the substrate surfaces, frequency components of evanescent waves oozing when light reflects on the substrate surfaces is resonance-absorbed when they agree with molecular vibrational frequencies of organic contaminants on the substrate surfaces, and their infrared radiation absorption spectra are measured, whereby kinds and amounts of the organic contaminants can be determined.

As the spectroscope 52, an infrared radiation spectroscope using a diffraction grating may be used in place of the FT-IR apparatus.

(h) Control/Analysis Computer 60 and Display Means 70

Measured data of spectra given by the spectroscope 52 are supplied to the control/analysis computer 60, and the control/analysis computer 60 identifies organic contaminants and computes their amounts.

Kinds of organic contaminants and calibration curves are saved as separate data bases in memories of the control/analysis computer 60. Monitored data are quantitized with reference to the data.

The thus analyzed results can be displayed on display means 70.

(2) Surface State Monitoring Method

The surface state monitoring method according to the present embodiment will be explained with reference to FIG. 1 and FIGS. 11 to 15.

Figure 11:
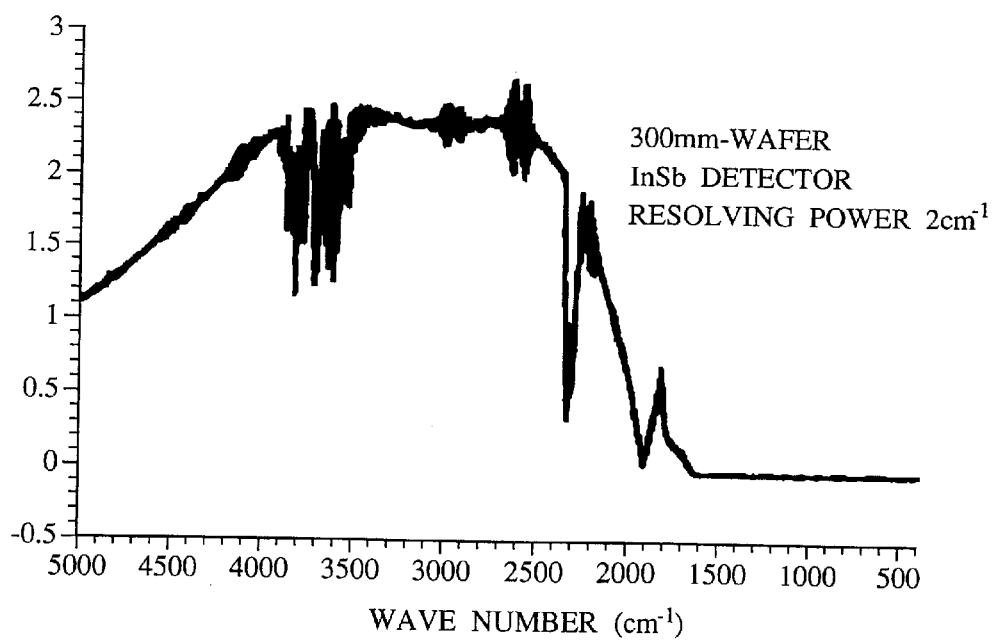
FIG. 11 is a graph of spectra of the internal multiple reflection in the 300 mm wafer.
Figure 12:
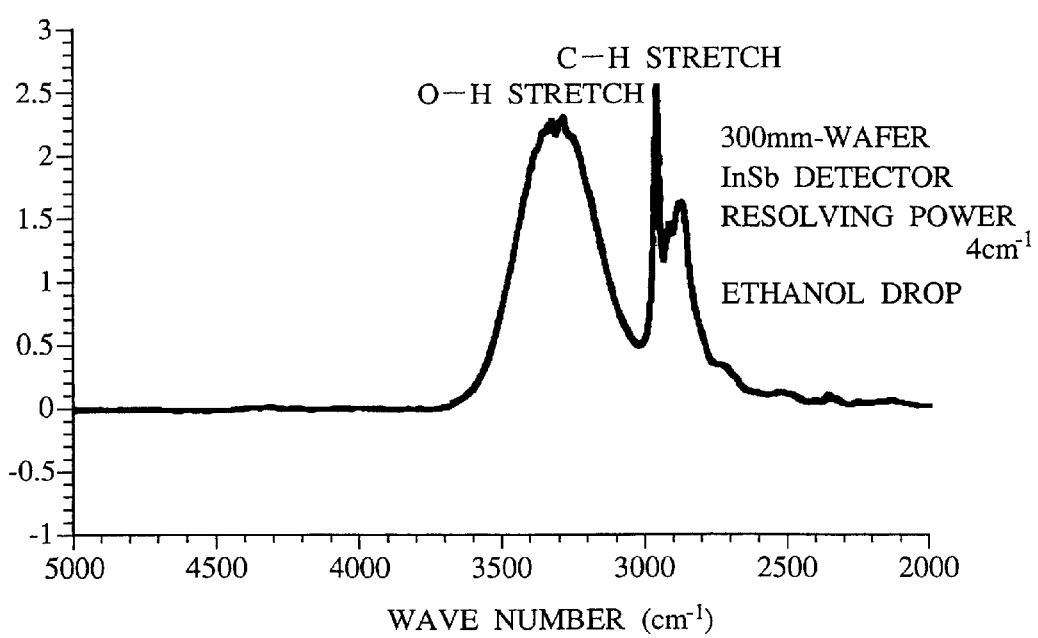
FIG. 12 is a graph of absorbance spectra given by internal multiple reflection in a substrate-to-be-monitored.
Figure 13:
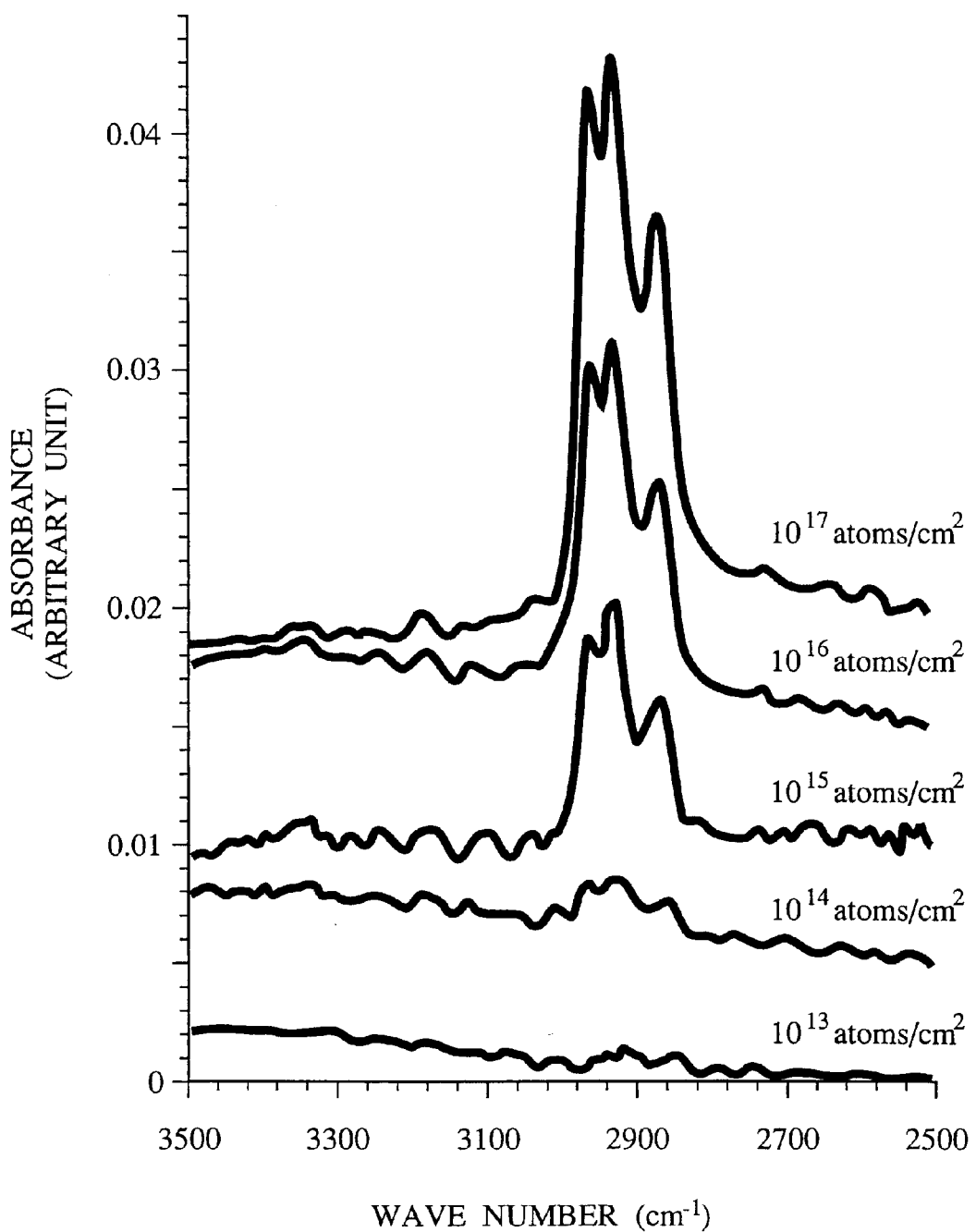
FIG. 13 is a graph of relationships between absorbance spectra and amounts of staying contaminants.
Figure 15:
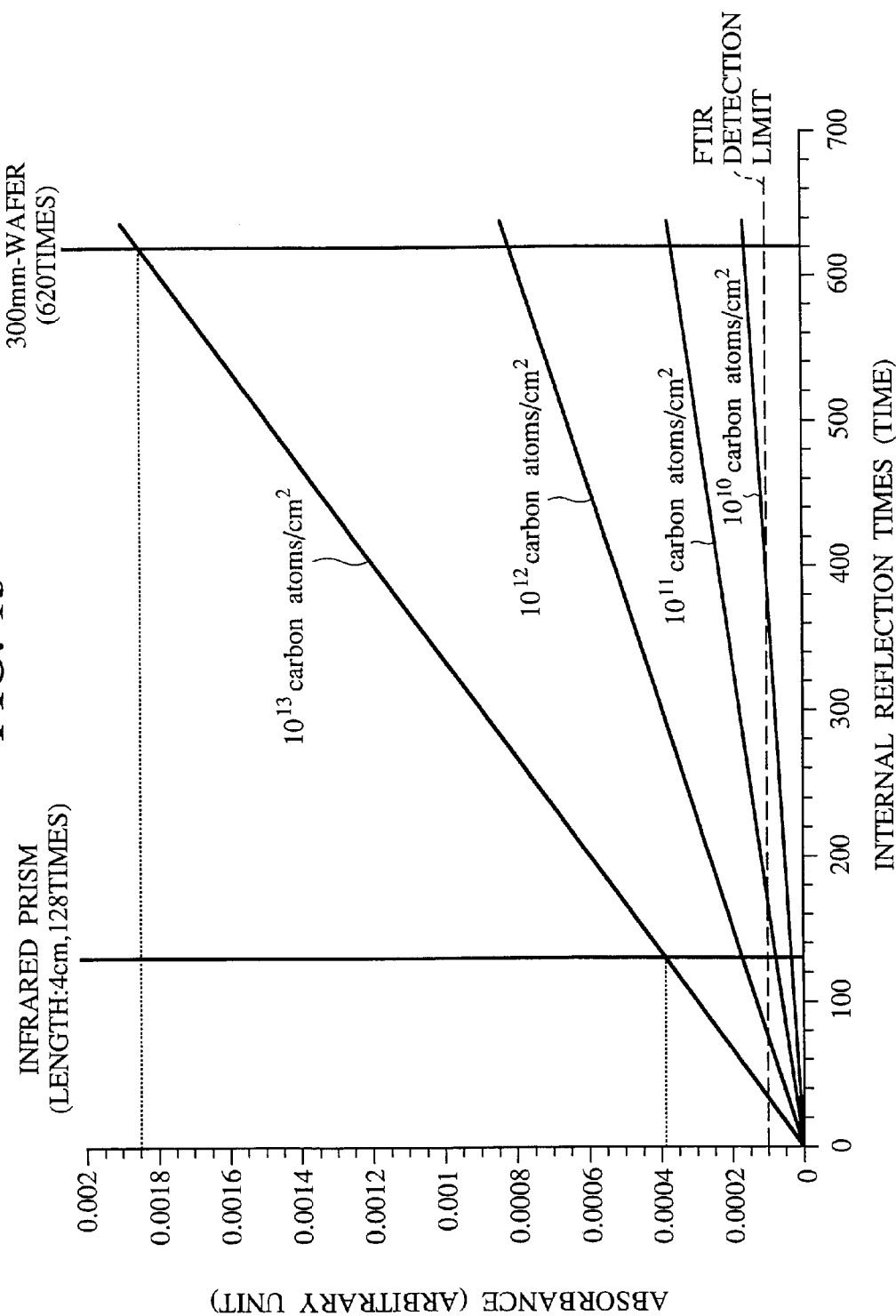
FIG. 15 is a graph of relationships between absorbances and times of internal multiple reflection.

FIG. 1 is a diagrammatic view of the surface state monitoring apparatus according to the present embodiment. FIG. 11 is a graph of spectra of multi reflection inside a 300 mm wafer. FIG. 12 is a graph of absorbance spectra given by the internal multiple reflection. FIG. 13 is a graph of relationships between absorbances and contaminant staying amounts. FIG. 15 is a graph of relationships between absorbances and times of the internal multiple reflection.

(a) Monitoring Method with an Incident Angle of Infrared Radiation Set

First, the infrared radiation source 20 is located at a required position by the control/analysis computer 60 through the light source position adjusting means 22, and infrared radiation is emitted. Emitted infrared radiation is formed into substantially parallel rays by the rear reflection plate 26 and the front reflection plate 28 to be incident on the infrared radiation condensing means 30.

The infrared radiation incident on the infrared radiation condensing means 30 is reflected on the reflection plate 32 and further on the concave mirror 34 tilted with respect to the optical axis to be applied to the outer periphery of a substrate-to-be-monitored 12 in an elliptical focus. At this time, a position of the substrate-to-be-monitored 12 and the infrared radiation condensing means have been adjusted respectively by the substrate mount control means 16 and the incident angle controller 80 so that the condensed infrared radiation is incident on the declined part 14 of the substrate-to-be-monitored at a required angle, a light amount detected by the infrared radiation detector 50 after the multiple reflection in the substrate-to-be-monitored is maximum.

Infrared radiation introduced into the substrate-to-be-monitored 12 through the declined part 14 of the substrate-to-be-monitored 12 repeats the internal multiple reflection while probing the surfaces of the substrate-to-be-monitored, accumulating contamination information thereon, and exits at a position symmetric to the incident position of the infrared radiation.

Then, the infrared radiation which has exited the substrate-to-be-monitored 12 is condensed by the infrared radiation condensing means 40 and is let to the infrared radiation detector 50 through the spectroscope 52. FIG. 11 show one example of spectra of the internal multiple reflection measured by the infrared radiation detector 50.

The infrared radiation which has exited the substrate-to-be-monitored 12 is diffracted by the spectroscope 52 and is detected by the infrared radiation detector 50. The infrared radiation is represented in absorption spectra corresponding to respective frequencies by the mechanism of Fourier-transform spectroscopy.

Memories of the control/analysis computer 60 store kinds of organic contaminants and calibration curves as separate data bases. The spectra are analyzed with reference to the data to identify kinds and amounts of organic contaminants.

FIG. 12 shows absorbance spectra measured on a 300 mm silicon wafer with ethanol dropped on the surfaces. The absorbance spectra represent differences of the internal multiple reflection between spectra for the case that the surfaces of the substrate is free from contaminants and spectra for the case that the surfaces of the substrate has contaminants.

As shown, peaks are detected at certain frequency bands. Based on the positions of the peaks, the peaks can be identified to correspond to O—H stretching and C—H stretching. Calibration curves indicating absorbances and contaminant amounts are measured in advance, so that amounts of organic contaminants can be identified based on peak intensities of the absorbances.

Output signals of the infrared radiation detector 50 are analyzed by the control/analyze computer, and a result of the analysis is presented on the display means 70.

Thus, a surface state of a substrate is monitored.

When required, the same measurement as described above is repeated after the substrate-to-be-monitored 12 is rotated by the substrate mount 10 so as to monitor surface states substantially all over the surfaces. The general silicon wafers have the circular outer periphery partially cut off straight, but a 300 mm diameter silicon wafer in accordance with SEMI standard specifications has only a fine recess in the shape of a notch formed in the surface of the outer periphery, which causes no trouble in rotating the 300 mm-diameter silicon wafer for the infrared radiation to enter the declined part 14 and exit.

(b) Monitoring Method Incident Angles of Infrared Radiation Scanned

The basic monitoring steps are the same as described in the case that incident angles of infrared radiation are set.

In scanning incident angles of infrared radiation, for example, when rotation of the concave mirror 34 is controlled by the incident angle controller 80, concurrently therewith a signal corresponding to the incident angle is outputted by the incident angle controller 80, and in response to the signal the infrared radiation detector 50 is driven through the control/analysis computer 60.

First, infrared radiation emitted by the infrared radiation source 20 is incident on a substrate-to-be-monitored 12 at a first angle formed by rotation of the concave mirror 34 controlled by the incident angle controller 80. Concurrently therewith, the infrared radiation detector 50 is driven to detect the infrared radiation which has been incident at the first incident angle and performed probing, and surface analysis of the substrate-to-be-monitored 12 is performed.

Then, infrared radiation is incident on the substrate-to-be-monitored 12 at a second angle formed by rotation of the concave mirror 34 controlled by the incident angle controller 80, and concurrently therewith the infrared radiation detector 50 is driven to perform surface analysis of the substrate-to-be-monitored, based on infrared radiation incident at the second incident angle.

Incident angles of infrared radiation is thus controlled continuously so as to be in the above-described range, whereby surface states of the substrate-to-be-monitored 12 along optical paths of the infrared radiation. Thus, subtle surface states can be analyzed or observed with high sensitivity.

(c) Relationship between Reflection Time and Detection Sensitivity

As described above, in the surface state monitoring method according to the present embodiment, large-diameter substrates, such as 300 mm silicon wafers in accordance with SEMI standard specifications, etc., can be monitored in-situ. The use of such monitoring method can yield drastically improved detection sensitivity. Then, relationship between the surface state monitoring method according to the present embodiment and detection sensitivity will be explained.

The monitoring method for monitoring organic contaminants by the internal multiple reflection FT-IR method uses the fact that organic contaminants absorb infrared radiation of specific wavelengths. It has been confirmed that degrees of infrared radiation absorption and staying amounts of organic contaminants have substantially proportional relationship between the two.

FIG. 13 shows infrared radiation absorption spectra which show relationships between infrared radiation absorption amounts (absorbances) and staying amounts (residual carbon amounts) on a sample which is a 300 mm silicon wafer with DOP diluted with ethanol applied to the entire surfaces. The staying amounts are staying amounts per a unit area given based on a dilution ratio and a wafer area. Conditions for measuring internal multiple reflection FT-IR were a 30° infrared radiation incident angle, a 22° declination of the declined part of the wafer, and a 32° internal reflection angle with respect to the direction of the normal of the substrate surfaces.

Figure 14:
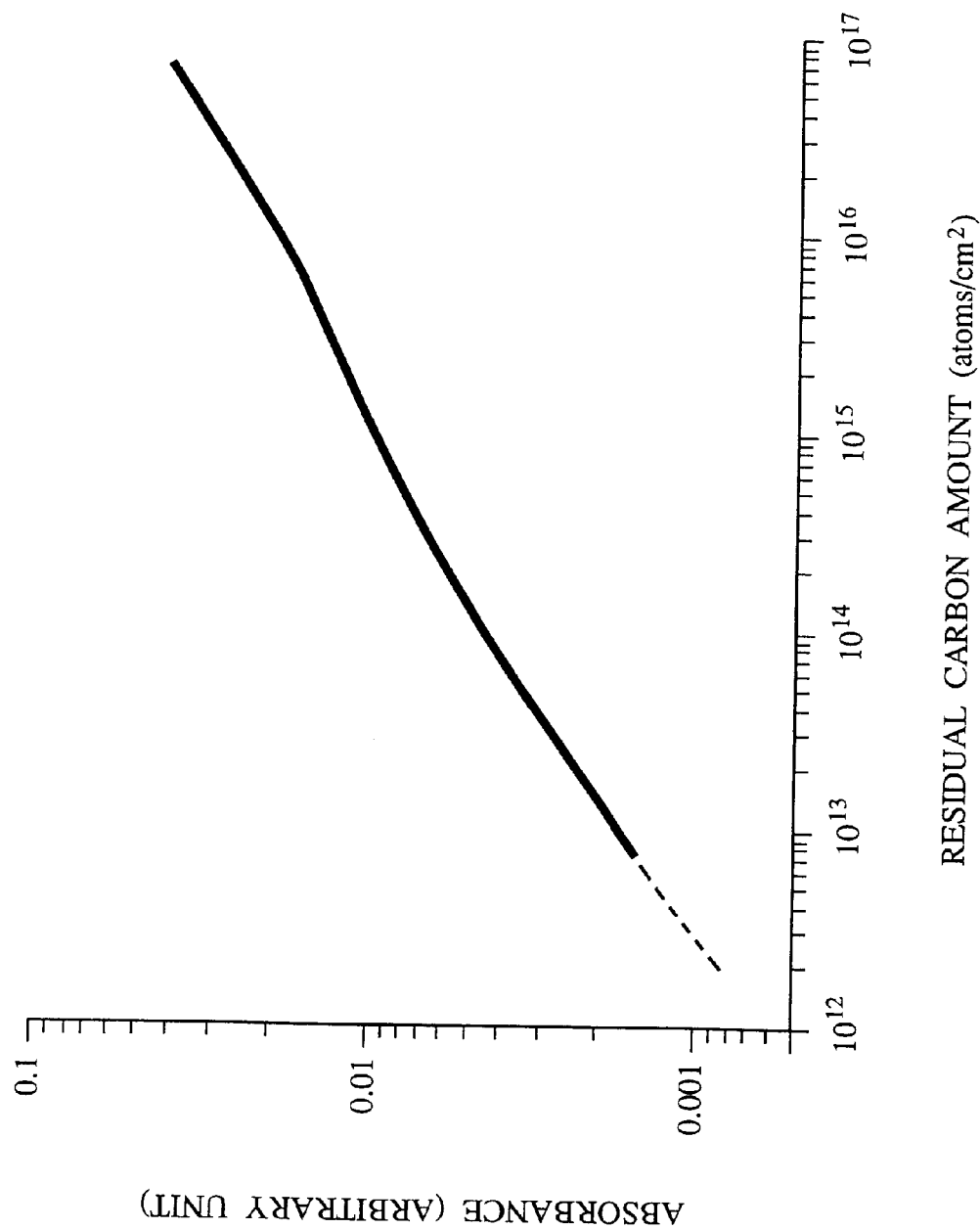
FIG. 14 is a graph of relationships between absorbance spectra and amounts of staying carbon atoms.

As shown in FIG. 13, it is found that as the residual carbon amount increases, the absorbance increases. The relationship between the absorbances and the residual carbon amounts in FIG. 13 is graphed in as shown in FIG. 14. That is, the absorbances are substantially proportional to the logarithmic axis of the residual carbon amount.

Here, a time of multi reflection of infrared radiation in a wafer is expressed by $$n = d/(t \times \tan\theta)$$

where a diameter of the wafer is represented by d, a thickness of the wafer is represented by t, and a reflection angle of the infrared radiation to a direction of a normal of the substrate surfaces is represented by $\theta$. Under the above-described conditions, infrared radiation propagating in a 775 $\mu$m-thick and 300 mm-diameter wafer in the diameter direction reflects about 620 times in the wafer. If it is simply considered that an absorbance is proportional to a reflection time, a relationship between a reflection time and an absorbance is represented by a linear line passing the origin, and an inclination of the linear line increases as a staying amount of residual carbon amount increases.

The absorbances and the reflection times of infrared radiation shown in FIG. 14 are graphed as shown in FIG. 15. In FIG. 15 residual carbon amounts are a parameter, and values of the parameter were given by the graph of FIG. 14. Absorbances for below $10^{13}$ cm$^{-2}$ concentrations were given by extrapolation based on the graph of FIG. 14.

Figure 41A:
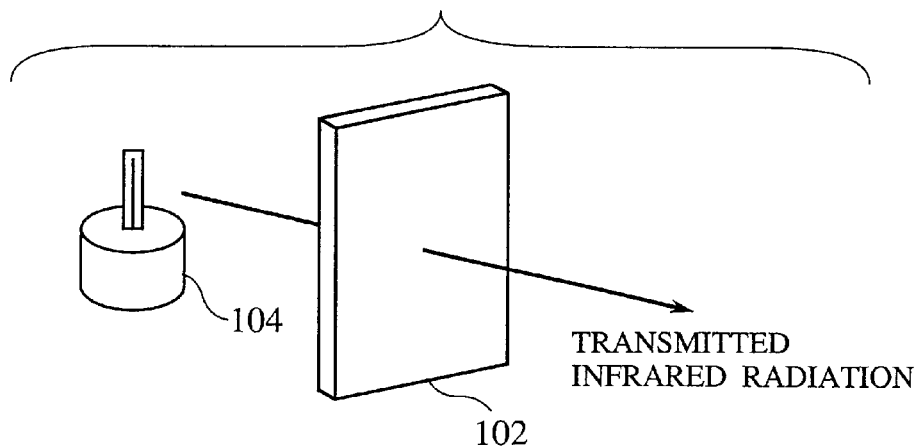
FIGS. 41A–41C are views explaining the conventional surface state monitoring methods and apparatuses.
Figure 41B:
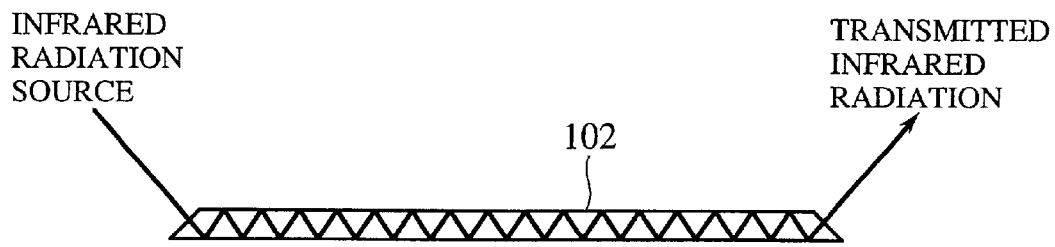
Figure 41C:
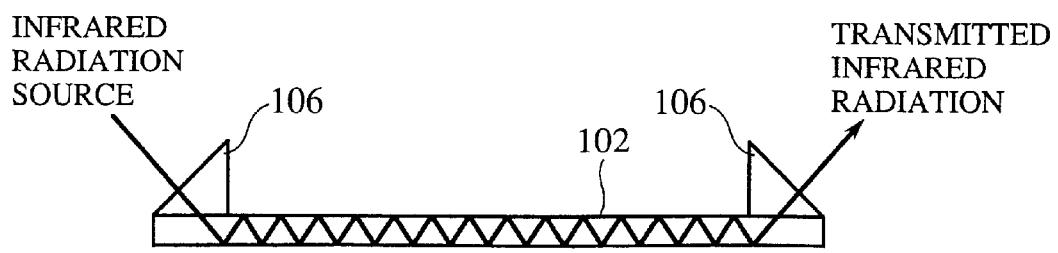

Here, in consideration of the conventional monitoring method using an infrared prism as shown in FIG. 41B, the infrared prism has a 4 cm-length, a 0.5 mm-thick and a 32° internal reflection angle with respect to the direction of a normal of the substrate surfaces, a time of the internal reflection is about 128 times, based on the above expression. Accordingly, an absorbance for a $10^{13}$ atoms/cm is about 0.0004 by the monitoring method using the infrared prism and is about 0.00185 by the monitoring method using the 300 mm wafer. Accordingly, even with the same staying amount, the monitoring method according to the present embodiment for monitoring a 300 mm wafer can provide a signal intensity which is about 4 to 5 times.

A lower limit value of a contamination amount which is detectable is determined by a minimum absorbance which can be identified by the FT-IR apparatus used in monitoring. It was confirmed that the FT-IR apparatus the inventors used can identify absorbances down to about 0.0001. When this value is considered as a detectable lower limit value, a staying amount of about $10^{12}$ atoms/cm$^2$ is a detectable lower limit value for the monitoring method using the infrared prism. For the monitoring method according to the present embodiment, a staying amount of $10^{10}$ atoms/cm$^2$ is a detectable lower limit value. Accordingly, the surface state monitoring method according to the present embodiment can improve the detection sensitivity by 1 to 2 places in comparison with the conventional monitoring method using an infrared prism.

In the present environments, it is considered that a staying carbon number which may be noted in terms of characteristics in fabricating a semiconductor device is about $10^{12}$ atoms/cm$^2$. Accordingly, it is preferable that a surface state monitoring technique for monitoring surface states of a substrate has a detection sensitivity of lower than $10^{11}$ atoms/cm$^2$ which allows for a sufficient margin. When the result of FIG. 15 is considered from this view point, it is preferable that a substrate in which infrared radiation undergoes internal multiple reflection more than about 300 times is used as a substrate for the monitoring.

Accordingly, the surface state monitoring method according to the present embodiment, which can realize 620 reflection times at a 32° internal reflection angle is considered very effective as monitoring means for in-situ monitoring surface states at site of fabrication of a semiconductor device.

As described above, according to the present embodiment, infrared radiation is incident on the declined part 14 of the end surface of a substrate-to-be-monitored 12, and surface states of the substrate are monitored based on internal multiple reflection of the infrared radiation which has entered through the declined part 14. To introduce infrared radiation into a substrate-to-be-monitored 12, it is not necessary to subject the substrate to additional processing, such as chemical etching or processing the end surface, or to introduce the infrared radiation into the substrate via a prism. Thus, the apparatus and method according to the present embodiment are applicable to the in-situ monitoring at the site of fabrication of semiconductor devices.

An incident angle of infrared radiation incident on a substrate-to-be-monitored 12 is continuously changed to monitor surface states of the substrate-to-be-monitored, whereby the surfaces of the substrate-to-be-monitored can be continuously analyzed along an optical path of the infrared radiation. Subtle surface states can be analyzed or observed with high sensitivity.

In the present embodiment, the substrate-to-be-monitored 12 is a silicon substrate but is not essentially a silicon substrate. The present embodiment is applicable to, e.g., germanium substrates, and compound substrates, as of GaAs, etc. The present embodiment is applicable unlimitedly to semiconductor substrates and is applicable on the same principle to glass substrates forming liquid crystal display devices.

In the present embodiment, a substrate-to-be-monitored 12 is held horizontal, for example, but may be held vertical or inclined.

In the present embodiment, infrared radiation is incident on the upper declined part 14 of a substrate-to-be-monitored 12 held horizontal so as to facilitate arrangement of the infrared radiation applying optical system. However, infrared radiation may be incident on the lower declined part 14, and the infrared radiation may be caused to exit also at the lower declined part 14.

In the present embodiment, the infrared radiation optical system is fixed and the substrate-to-be-monitored 12 is rotated by the rotation mechanism of the substrate mount 10 so as to facilitate arrangement of the apparatus. However, infrared radiation optical system may be rotated by the rotation mechanism around the fixed substrate-to-be-monitored 12.

In the present embodiment, infrared radiation is incident on the declined part 14 in plane vertical to the surfaces of a substrate-to-be-monitored 12, but infrared radiation may be incident on the declined part 14 in plane slanted with respect to the substrate surfaces. In the present embodiment infrared radiation is incident on the declined part 14 in plane passing the center of a substrate-to-be-monitored 12, but infrared radiation may be incident on the declined part 14 in plane which does not pass the center of a substrate-to-be-monitored 12.

However, in order to make a structure of the apparatus simple and detect the entire substrate surfaces with a maximum resolving power, it is preferable to apply infrared radiation to the declined part 14 in plane passing the center of the substrate-to-be-monitored vertically thereto as in the surface state monitoring method according to the present embodiment.

[A Second Embodiment]

The surface state monitoring method and apparatus according to a second embodiment of the present invention will be explained with reference to FIG. 16. The same reference numbers of the present embodiment as those of the surface state monitoring method and apparatus according to the first embodiment of the present invention will be represented by the same reference numbers not to repeat or to simplify their explanation.

(1) General Structure of the Apparatus

The surface state monitoring method and apparatus according to the first embodiment is very superior in that when species of molecular contaminants on the surfaces of a substrate-to-be-monitored is unknown, fully real-time detection of absence/presence of contamination and identification of contaminant molecular species can be performed incontiguously and non-destructively without cutting off the substrate-to-be-monitored. However, in a case that a contamination species has been known in advance, and absence/presence alone of the specific molecular species is detected to judge at low cost whether or not the substrate-to-be-monitored is good, in consideration that a Fourier-transform spectroscope is generally expensive, it is hard to say that the surface state monitoring method and apparatus according to the first embodiment is not always suitable.

Then, the surface state monitoring method and apparatus according to the present embodiment detects, in a case that a contaminant species is known in advance, absence/presence alone of the contaminant at low cost whether or not the substrate-to-be-monitored is good.

Figure 16:
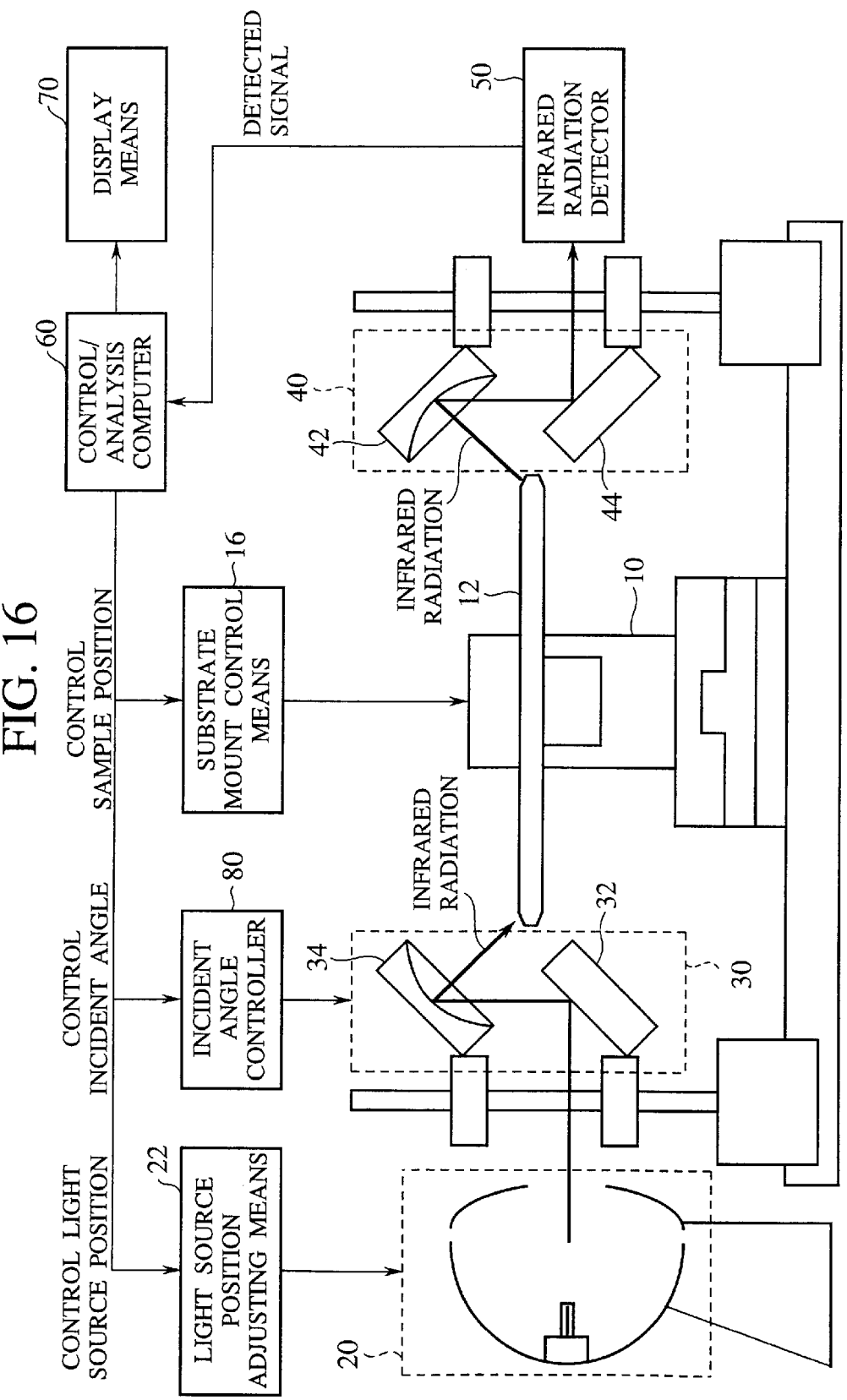
FIG. 16 is a diagrammatic view of the surface state monitoring apparatus according to a second embodiment of the present invention.

As shown in FIG. 16, the surface state monitoring apparatus according to the present embodiment has the same basic structure as that of the first embodiment. Substantial differences of the surface state monitoring apparatus according to the present embodiment from that according to the first embodiment is that the infrared radiation optical system is so arranged that the infrared radiation detector 50 can selectively detect infrared radiation of wavelengths corresponding to resonance absorption spectra of molecular species (organic contaminant, e.g., DOP (dioctyl phthalate), DMP (dibutyl phthalate), etc.), and the control/analysis computer 60 for analysis based on output signals from the infrared radiation detector 50 judges whether or not a substrate-to-be-monitored is good, based on power levels of output signals from the infrared radiation detector 50.

Atoms forming a molecule are bonded to one another by covalent bonds. Generally, a polyatomic molecule containing three or more atoms has complicated vibrations. The vibrations can be sorted in several basic vibration groups. A group vibration is that of a specific atomic group (functional group), e.g., transverse vibration, symmetric stretching vibration and antisymmetric stretching vibration of $CH_2$ group; C=O stretching vibration of carbonyl group; and stretching vibration of OH group. General organic molecules have frequencies in the infrared region. Tables 1-1 to 1-4 show infrared absorption characteristics of typical functional groups (Reference: Mitsuaki Mukohyama; "Kiso Yukikagaku", Maruzen).

TABLE 1-1

X—H Stretching Vibration

| Molecular Species | Infrared Radiation Absorption Characteristic [$cm^{-1}$] |
|---|---|
| —O—H | 3650~3100 |
| ≡C—H | 3330 |
| Ar—H | 3030 |

TABLE 1-1-continued

X—H Stretching Vibration

| Molecular Species | Infrared Radiation Absorption Characteristic [cm$^{-1}$] |
|---|---|
| —C—O— | 1200~1000 |
| —N—H | 3500~3100 |
| =C—H | 3080~3025 |
| —C—H | 2960~2870 |

TABLE 1-2

X=Y Stretching Vibration

| Molecular Species | Infrared Radiation Absorption Characteristic [cm$^{-1}$] |
|---|---|
| \C=O / | 1850~1650 |
| \C=O\ / / | 1680~1600 |
| —N=O | 1650~1500 |
| \C=NR / | 1690~1640 |
| —N=N— | 1630~1575 |
| Ar— | 1600~1450 |

TABLE 1-3

X≡Y Stretching Vibration

| Molecular Species | Infrared Radiation Absorption Characteristic [cm$^{-1}$] |
|---|---|
| —C≡N | 2260~2240 |
| RC≡CH | 2140~2100 |
| RC≡CR' | 2660~2190 |

TABLE 1-4

X—H Deformation Vibration

| Molecular Species | Infrared Radiation Absorption Characteristic [cm$^{-1}$] |
|---|---|
| —C—H— | 1470~1140 |
| Ar—H | 900~690 |
| =C—H | 1000~670 |

Accordingly, when infrared radiation of a wavelength range corresponding to frequency components of the organic molecules are applied, that of the infrared radiation of the same frequencies as intrinsic frequencies of the species is resonance absorbed. Based on resonance absorption spectra, the molecules being monitored can be identified. Their amounts can be determined based on intensities of the resonance absorption spectra. The surface state monitoring method and apparatus using such principle is those according to the first embodiment.

On the contrary, when a contaminant to be detected is known, and an optical wavelength in which a resonance absorption spectrum of the contaminant is already known based on Fourier-transform spectroscopic data, infrared radiation of a resonance absorption wavelength range of the contaminant to be detected is incident on a substrate-to-be-monitored 12, whereby an amount of the contaminant can be determined. An amount of the contaminant can be determined also by selectively detecting infrared radiation of a specific wavelength range.

In thus using infrared radiation of a specific wavelength range, attenuation of infrared radiation due to resonance absorption occurring when the infrared radiation undergo multiple reflection in a substrate-to-be-monitored 12 is considered to be mainly due to contaminants to be detected. An intensity of infrared radiation transmitted by a substrate free from molecular contamination (reference intensity) is measured in advance, and a level difference between an intensity of infrared radiation transmitted by a substrate-to-be-monitored 12 (measured intensity) and the reference intensity is given, whereby a resonance absorption amount of the infrared radiation due to a contaminant to be detected, i.e., an amount of the contaminant can be determined.

Then, the control/analysis computer 60 compares a thus determined level difference with a reference level (judgement level) corresponding to a prescribed amount of molecular contamination, whereby it can be judged whether or not the substrate-to-be-monitored 12 is good. In this computation the difference level is converted into electric signals.

This detection system does not use Fourier-transform spectroscopy but, to attain the required object, simply compares a power level of output signals from the infrared radiation detector 50 without the necessity of using a Fourier-transform spectroscope, which is expensive.

As in the surface state monitoring method and apparatus according to the first embodiment, organic contamination and chemical contamination on a substrate-to-be-monitored 12 can be in-situ detected or monitored without subjecting the substrate-to-be-monitored 12 additionally to chemical etching, processing of the end surfaces, etc. and introducing infrared radiation into the substrate-to-be-monitored 12 through a prism disposed above the substrate-to-be-monitored 12.

Characteristic constituent members of the surface state monitoring apparatus according to the present embodiment will be detailed. The constituent members of the surface state monitoring apparatus according to the present embodiment other than those which will be described below are the same as those of the surface state monitoring apparatus according to the first embodiment. The surface state monitoring apparatus according to the present embodiment can be formed also by optionally combining the constituent members of a third to an eighth embodiments which will be described below.

(a) Infrared Radiation Source 20

An infrared radiation source 20 of the present embodiment is a light source 24 which selectively emits infrared radiation in a resonance absorption wavelength range (wavelength range corresponding to molecular frequency) of a contaminant to be detected.

A light source 24 having a wavelength corresponding to a molecular frequency of a specific substance may 1) select by an optical band pass-type filter a specific wavelength from a light source having a wide band width in the infrared region or the near infrared region; may 2) oscillate a specific wavelength by a multi-group-system semiconductor laser; may 3) mix two laser beams of different wavelengths with an optically nonlinear substance and select by an optical band pass-type filter a specific wavelength out of an added wavelength or a subtracted wavelength; may 4) oscillate a specific wavelength by optical parametric oscillation; and may 5) oscillate a specific wavelength by a variable tuning laser.

These light sources are applied to, e.g., the infrared radiation source 24 shown in FIG. 2 to constitute the infrared radiation source 20, whereby an infrared radiation source which emits infrared radiation or near-infrared radiation applicably to the surface state monitoring method and apparatus according to the present embodiment can be obtained.

In place of the light source 24 which selectively emits infrared radiation of a specific wavelength, the infrared radiation source 20 is arranged to emit light having a wide wavelength range extended from the near-infrared radiation to the infrared radiation, and light which has probed a substrate-to-be-monitored 12 is passed through an optical band-pass filter to select a specific wavelength, and the specific wavelength is detected by the infrared radiation detector 50.

(b) Infrared Radiation Detector 50

Infrared radiation which has exited a substrate-to-be-monitored 12 is led to the infrared radiation detector 50 through infrared radiation condensing means 40. The infrared radiation detector 50 is provided, for example, by an InSbAs-PIN photodiode, a Ge photodiode or others as the typical near-infrared radiation detector; an InAs or an InSb photovolatic element as the infrared radiation detector; or a detector, such as an MCT (MgCdTe) photo-conductive element, a pyroelectric element or others. These detectors convert near-infrared radiation and infrared radiation to electric signals.

In the surface state monitoring method and apparatus according to the present embodiment of the present invention, the infrared radiation detector 50 measures a power level of light which has been emitted and passed a substrate-to-be-monitored 12, and converts the power level to a quantity of electricity.

(c) Control/Analysis Computer 60 and Display Means 70

The control/analysis computer 60 receives an electric signal corresponding to a power level (measured intensity) of infrared radiation given by the infrared radiation detector 50 and compare the electric signal with a pre-measured reference intensity. Based on a difference between the reference intensity and the measured intensity, an amount of a contaminant present on a substrate-to-be-monitored 12 is identified.

A thus-given level difference is compared with a reference level corresponding to a set amount of molecular contamination, and judges whether or not the substrate-to-be-monitored 12 is good.

A thus-analyzed result can be displayed on the display means 70.

(2) Surface State Monitoring Method

The surface state monitoring method according to the present embodiment will be explained with reference to FIG. 16.

First, an infrared radiation source 20 which emits light of a wavelength corresponding to molecular frequency of a contaminant to be detected. In a case, for example that a contaminant to be detected is ethanol as in the monitoring example shown in FIG. 11, the infrared radiation source 24 is arranged to emit infrared radiation of a wave number range corresponding to 3650–3100 $cm^{-1}$ for, e.g., O—H stretching vibration.

Next, a reference sample with no contaminant staying on is placed on a substrate mount 10, and a reference monitored intensity is measured. The measured reference intensity is saved in the control/analysis computer 60. Optical alignment and fine adjustment for the measurement are the same as in the surface state monitoring method according to the first embodiment.

Next, a substrate-to-be-monitored 12 is placed on the substrate mount 10, and measurement is performed to give a monitored intensity. Optical alignment and fine adjustment for the measurement are the same as in the surface state monitoring method according to the first embodiment.

Next, a monitored intensity of infrared radiation thus measured is inputted to the control/analysis computer 60 and is compared with the pre-measured reference intensity. Based on a level difference between the reference intensity and the measured intensity, an amount of a contaminant is decided. When the level difference between the reference intensity and the measured intensity is above a preset level which is a standard for judging whether the substrate-to-be-monitored is good, the control/analysis computer 60 judges the substrate-to-be-monitored is defective.

In a case that the infrared radiation source 20 is arranged to emit a wide band of light, a reference intensity is measured in the same way as described above, and then infrared radiation emitted by the infrared radiation source 20 is incident on a substrate-to-be-monitored 12 under prescribed conditions to probe the substrate-to-be-monitored 12 for surface states and is passed through an optical band-pass type filter or others to select a specific wavelength. Infrared radiation of the specific wavelength is detected by the infrared radiation detector 50.

Then, a measured intensity of the infrared radiation thus measured is inputted to the control/analysis computer 60 to be compared with a pre-measured reference intensity. Based on a level difference between the reference intensity and the measured intensity, an amount of a contaminant is decided. When a level difference between the reference intensity and the measured intensity is above a prescribed level which is a standard for judging whether or not a substrate-to-bemonitored is good, the control/analysis computer 60 judges the substrate-to-be-monitored 12 is defective.

Thus, surface states of the substrate-to-be-monitored 12 are monitored, and it is judged whether the substrate-to-be-monitored is good.

As described above, according to the present embodiment, light of a wavelength range corresponding to a molecular vibration of a specific contaminant is used to monitor surface states, and an attenuation amount of a light intensity due to resonance absorption, an amount of the contaminant is determined. No expensive system, such as a Fourier-transform spectroscope, etc., is necessary, and it is judged at low costs whether or not a substrate is good.

In the above-described embodiment, light of a wavelength range corresponding to a molecular vibration of a contaminant is detected, but in a case that a plurality of contaminants must be measured, it is possible that light of respective wavelengths corresponding to specific frequencies of the respective contaminants is generated, and these waves are combined to be applied to. It is also possible that the infrared radiation source is provided by a variable tuning laser or others, and light of specific wavelengths corresponding to a plurality of molecular vibrations may be sequentially oscillated.

[A Third Embodiment]

The surface state monitoring method and apparatus according to a third embodiment of the present invention will be explained with reference to FIGS. 17 to 23. The same members of the present embodiment as those of the surface state monitoring method and apparatus according to the first or the second embodiment shown in FIGS. 1 to 16 are represented by the same reference numbers not to repeat or to simplify their explanation.

Figure 18:
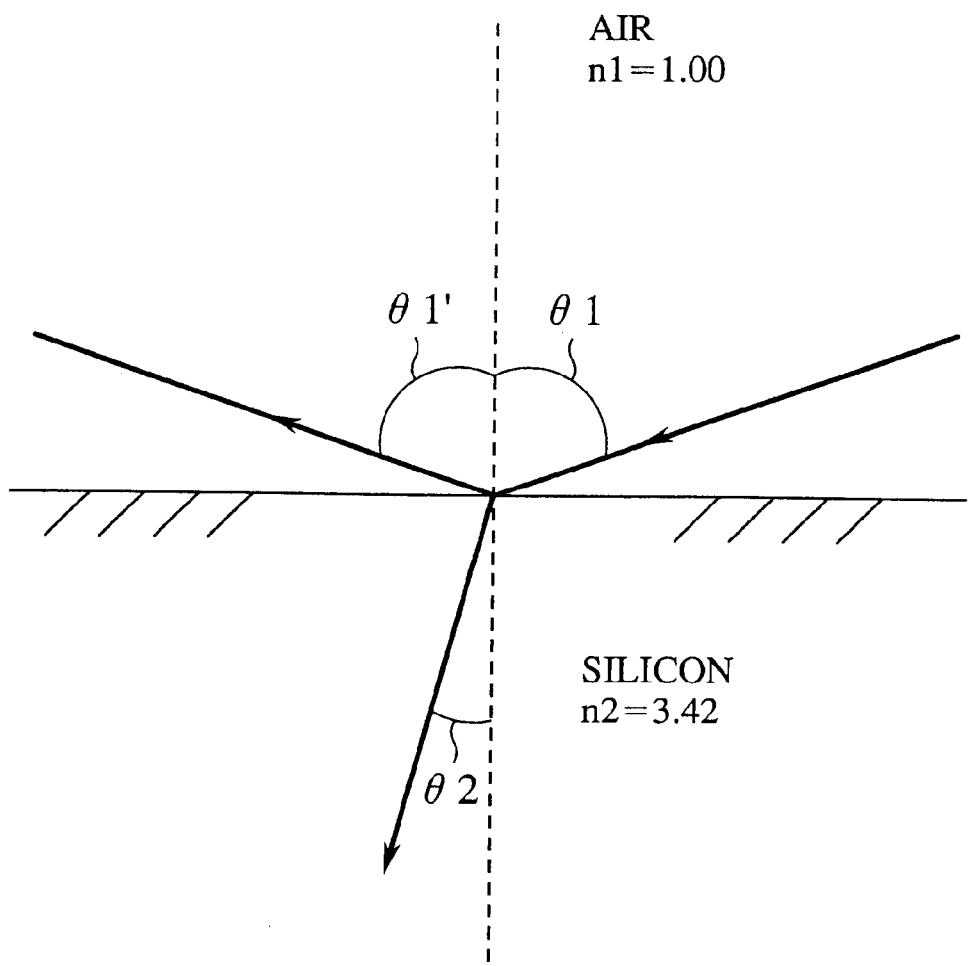
FIG. 18 is a schematic view of a state in which light enters a silicon from air.
Figure 19:
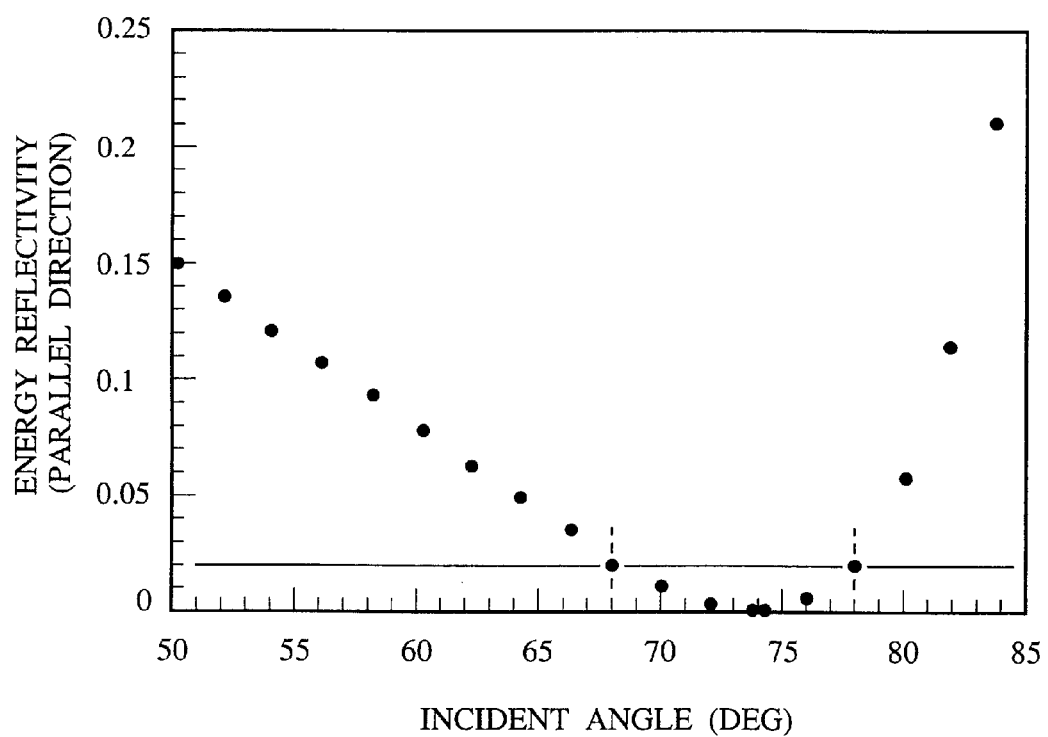
FIG. 19 is a characteristic view of relationships between incident angles and energy reflectivities.
Figure 21:
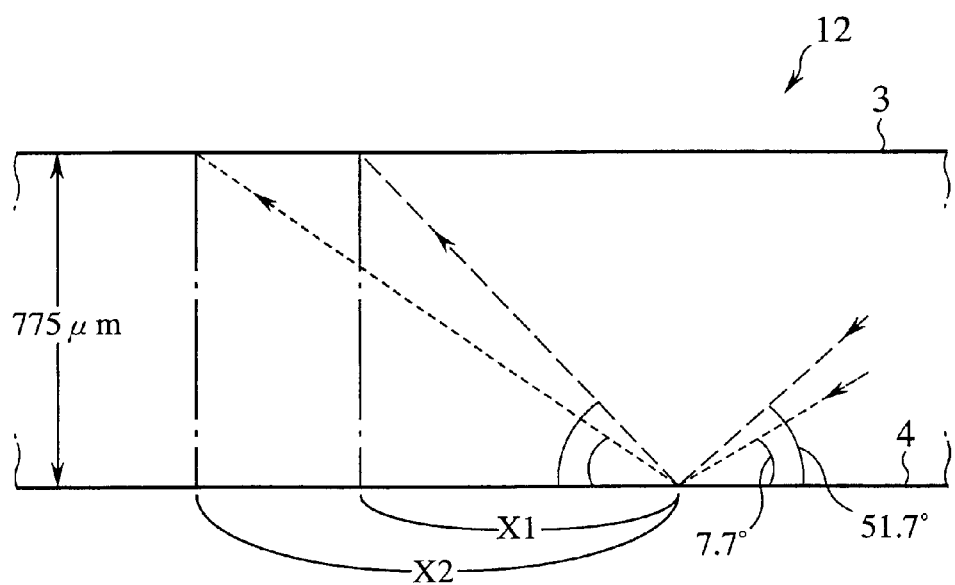
FIG. 21 is a schematic view of a state in which infrared radiation is reflected inside a silicon wafer.
Figure 22:
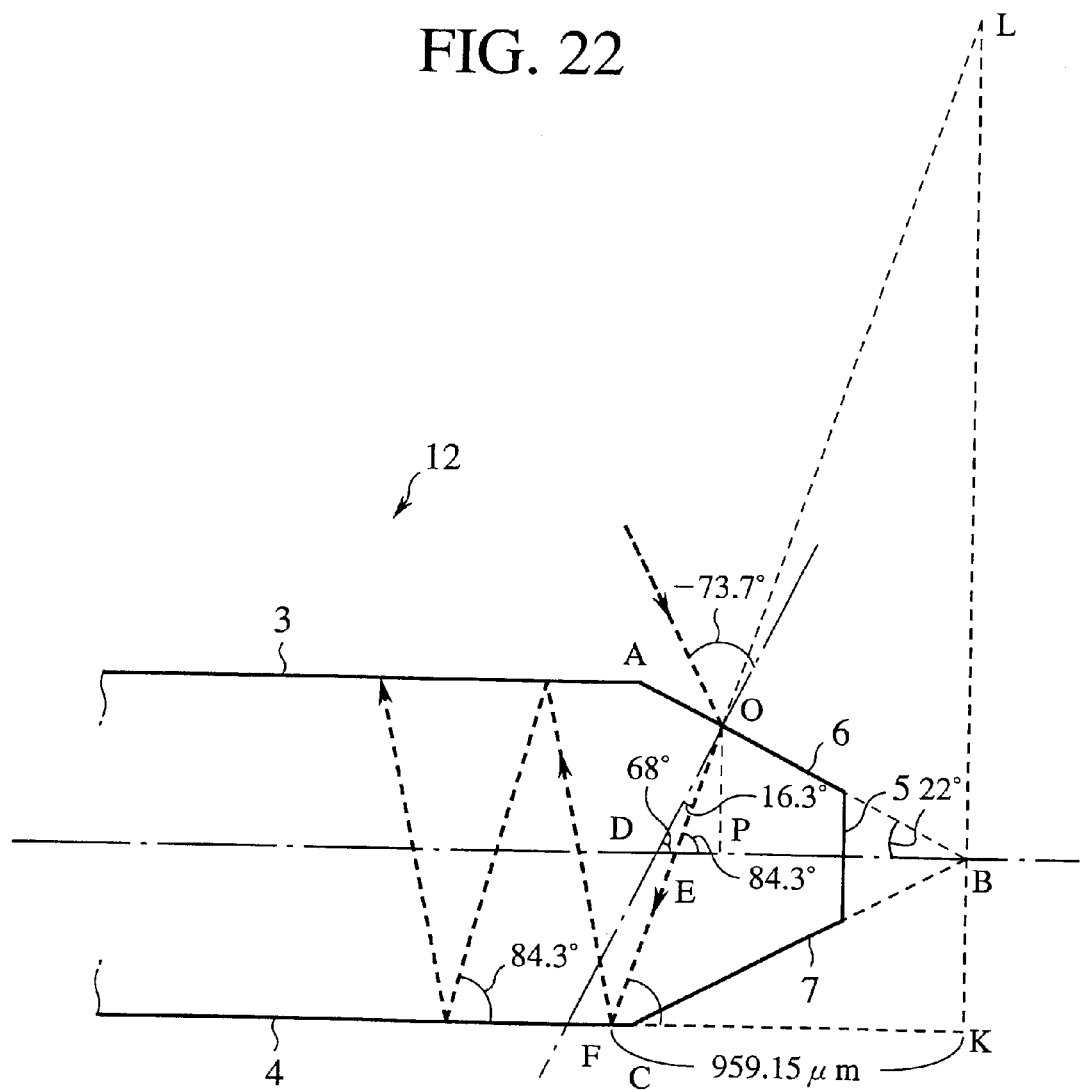
FIG. 22 is a schematic sectional view of a substrate-to-be-monitored, which shows relationships between the substrate-to-be-monitored and infrared radiation.
Figure 23:
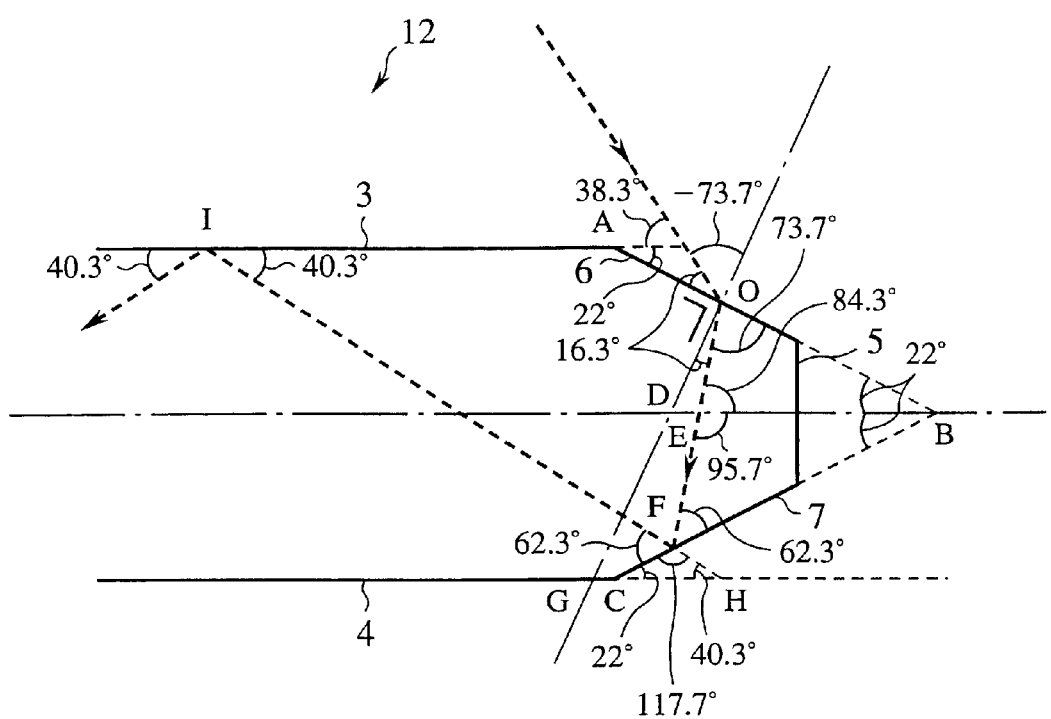
FIG. 23 is a schematic sectional view of a substrate-to-be-monitored, which shows a state in which an incident angle of infrared radiation is not proper.

FIGS. 17A and 17B are schematic sectional views showing relationships of the substrate-to-be-monitored with infrared radiation in the surface state monitoring method and apparatus according to the present embodiment. FIG. 18 is a schematic view of light incident on silicon from air. FIG. 19 is a characteristic view of relationships between incident angles of infrared radiation with energy reflectivities. FIGS. 20A and 20B are schematic sectional views showing a state in which an incident position of infrared radiation is not proper. FIG. 21 is a schematic view showing a state in which infrared radiation is reflected inside a wafer. FIG. 22 is a schematic sectional view of a substrate-to-be-monitored, which shows relationships between the substrate-to-be-monitored and infrared radiation. FIG. 23 is a schematic sectional view of a substrate-to-be-monitored in a case that an incident position of infrared radiation is not proper.

In the present embodiment, an arrangement of the infrared optical system of the surface state monitoring method and apparatus according to the first and the second embodiments will be explained here.

In order to monitor surface states of a substrate-to-be-monitored 12 with high sensitivity, it is necessary that infrared radiation is effectively introduced into the substrate-to-be-monitored and is caused to undergo internal multiple reflection. To this end, in the surface state monitoring method and apparatus according to the present embodiment, the infrared radiation incidence optical system is held at a suitable position and at a suitable angle by a support member (incident angle control system) so that infrared radiation is incident at a substantial Brewster angle on the declined part 14 of the substrate-to-be-monitored.

In more details, the infrared radiation incidence optical system, as shown in FIG. 17A, is held at an angle which permits an incident angle of infrared radiation to be about 73.7° with respect to an end surface 6 (the declined part 14) in plane which is vertical to the substrate surfaces 3, 4 of the substrate-to-be-monitored 12 and passes the center, and furthermore is held at a position, as shown in FIG. 17B, which permits the infrared radiation to be incident on a position O on the end surface 6 which is spaced by about 0–500.56 $\mu$m from the boundary A which is a boundary between the end surface 6 and the substrate surface 3 of the substrate-to-be-monitored 12.

This makes reflection loss of infrared radiation applied to the end surface 6 of the substrate-to-be-monitored 12 trivial, and the infrared radiation has high energy efficiency.

Infrared radiation incident on the upper end surface 6 of the substrate-to-be-monitored 12 and refracted is prevented from being directly incident on the lower end surface 7 (the declined part 14) from the inside, whereby the infrared radiation is reflected on a pair of the substrate surfaces 3, 4 at a number of positions inside the substrate-to-be-monitored 12, whereby presence/absence of organic contamination can be detected with good resolution.

A process for designing the infrared radiation optical system according to the present embodiment will be explained. In the present embodiment, a substrate-to-be-monitored 12 is provided by a 300 mm silicon wafer in accordance with SEMI standard specifications. As described above, the silicon wafer is formed in a disc having an about 77.5 $\mu$m-thick and an about 300 mm-diameter, and has the boundary between a pair of the substrate surfaces and the outer peripheral surface chamfered in a pair of end surfaces (the declined parts 14) which is declined by about 22° (see FIGS. 6 and 7). The infrared radiation optical system can be designed in the same process as will be described below for substrates chamfered in a pair of declined end surfaces other than 300 mm silicon wafers in accordance with SEMI standard specifications.

When light enters a region of a refractive index $n_2$ from a region of a refractive index $n_1$, as shown in FIG. 18, reflection on the boundary surface between the region takes place at an angle $\theta_1$ identical with an incident angle $\theta_1$, and refraction takes place at an angle $\theta_2$:

$$n_1 \sin \theta_1 = n_2 \sin \theta_2.$$

Here, when light is passed into silicon from air, the refractive index of air is $n_1=1.00$, and the refractive index of silicon is $n_2=3.42$. An incident angle $\theta_1$ which yields a minimum reflection loss (Brewster angle) satisfies $$\theta_1 + \theta_2 = \pi/2$$

$$\tan \theta_1 = n_2/n_1 = 3.42.$$

Based on the above conditions, an incident angle $\theta_1$ is given by:

$$\theta_1 = 73.7°,$$

and a refraction angle $\theta_2$ is given by:

$$\theta_2 = 16.3°.$$

In the surface state monitoring method according to the present embodiment, infrared radiation is incident on the end surface 6 of a substrate-to-be-monitored (silicon wafer) at a substantial Brewster angle given by the above computation, whereby higher energy efficiency is obtained at minimum reflection loss.

Here, when an amplitude reflectance of a component parallel with the end surface 6 on which infrared radiation is incident is represented by r(h), an amplitude reflectance r(h) is given by:

$$r(h)=\tan(\theta_1-\theta_2)/\tan(\theta_1+\theta_2),$$

and an energy reflectivity r(h) of the infrared radiation incident on the end surface 6 is given by:

$$r(h)=[r(h)]^2.$$

As shown in FIG. 19, the energy reflectivity r(h) is minimum when an incident angle $\theta_1$ is 73.7° which is a Brewster angle, and rises when the incident angle $\theta_1$ increases or decreases. A change ratio of the energy reflectivity r(h) on the side of increase of the incident angle $\theta_1$ is different from that on the side of decrease of the incident angle $\theta_1$. Then, in the present embodiment, on the assumption that an allowable range of the reflection loss is 2.0% (=0.02), an incident angle of infrared radiation on the end surface 6 of a substrate-to-be-monitored 12 is 68–78°.

However, even if an incident angle of infrared radiation is thus set, unless an incident position is proper, it often takes place as shown in FIG. 20A, infrared radiation incident on the end surface 6 is incident directly on the end surface 7 from the inside and reflected thereon. in this case, angles of the infrared radiation with respect to the substrate surfaces 3, 4 inside a substrate-to-be-monitored are shallow. The infrared radiation is reflected on the substrate surfaces 3, 4 less times, and the resolving power for the contamination detection is low.

As described above, for example, when infrared radiation is incident at 73.7° on the end surface 6 of a substrate-to-be-monitored 12 declined at 22° and is incident on the substrate surface 4 without being incident on the end surface 7 from the inside, a reflection angle of the infrared radiation inside the substrate-to-be-monitored 12 is 51.7°.

Here, when the substrate-to-be-monitored 12 has a 775 $\mu$m-thickness, as shown in FIG. 21 a distance $X_1$ over which the infrared radiation horizontally propagates for once reflection is given by:

$$X_1=775\times\tan(90-51.7)=612.06\ \mu m.$$

This means that the substrate surfaces 3, 4 are detected at every 1224 $\mu$m-distance. This is a sufficient resolving power for the detection of organic contamination.

However, when infrared radiation incident on the end surface 6 of the substrate-to-be-monitored 12 is incident directly on the end surface 7, as shown in FIG. 20B a reflection angle of the infrared radiation inside the substrate-to-be-monitored 12 is 7.7°. In this case, a distance $X_2$ over which the infrared radiation horizontally propagates for once reflection is given by:

$$X_2=775\times\tan(90-7.7)=5732.02\ \mu m.$$

The resolving power for the detection is lowered substantially to 1/10.

Then, in the surface state monitoring method according to the present embodiment, an incident angle and an incident position of infrared radiation are set with respect to a substrate-to-be-monitored 12, whereby as shown in FIG. 17B, infrared radiation incident on the end surface 6 of the substrate-to-be-monitored 12 is prohibited from directly being incident on the end surface 7 from the inside.

To this end, it is necessary that infrared radiation entering the substrate-to-be-monitored 12 at the position O on the upper end surface 6 of the substrate-to-be-monitored 12 is incident on a position on the substrate surface 4, which is on the left side, as viewed in the drawing, of the boundary C with respect to the lower end surface 7. Here, when a boundary B between the end surfaces 6, 7, a boundary C between the substrate surface 4 and the end surface 7, and a position K directly below the boundary B and horizontally leftward of the boundary C are assumed, the linear line BK is 387.5 $\mu$m which is a half a thickness of the substrate-to-be-monitored 12.

$$BK/CK=387.5/CK=\tan 22=0.404.$$

Therefore the linear line CK is 959.15 $\mu$m.

$$BK/BC=387.5/BC=\sin 22=0.3746.$$

Therefore, the liner line BC is 1034.44 $\mu$m, and the linear line AB symmetric with the linear line BC is 1034.44 $\mu$m. When an intersection between the extended linear line KB and the extended linear line OC is represented by L, L K/CK=tan 51.7=1.2662.

The linear line LK is 1214.48 $\mu$m, and the linear line LB is given by:

$$LK-BK=1214.28-387.5=826.78\ \mu m.$$

Here, when coordinates (x, y) of the position O on the end surface 6 on which infrared radiation is incident, with the boundary B between the end surfaces 6, 7 set as the origin, the position O is the intersection between the linear line AB and the linear line CL. The linear line AB is expressed by $$y=-(\tan 22)\times=-0.404\times,$$

and the linear line CL is expressed by $$y=+(\tan 51.7)\times+LB=1.2662\times+826.78.$$

When coordinates of the position O, which is the intersection between the linear line AB and the linear line CL, are computed by the above-described expressions, $$x=-495.02\ \mu m,$$

and $$y=199.99\ \mu m.$$

When an intersection P between a perpendicular passing the position O and a horizon passing the origin is assumed, the linear line PB is 495.02 $\mu$m.

$$PB/OB=\cos 22=0.92718.$$

Therefore $$OB=495.02/0.92718=533.9\ \mu m,$$

and $$AO=AB-OB=1034.46-533.9=500.56\ \mu m.$$

That is, in a case that a substrate-to-be-monitored 12 has an about 775 $\mu$m-thick and has a pair of end surfaces 6, 7 declined at about 22° with respect to a pair of substrate surfaces 3, 4, and infrared radiation is incident on the end surface 6 at a 73.7° incident angle which is a Brewster angle, the infrared radiation is incident on the position O which is spaced by 0–500.56 $\mu$m from the boundary A between the end surface 6 and the substrate surface 3, whereby the infrared radiation which has entered the substrate-to-be-monitored 12 at the end surface 6 is never incident directly on the end surface 7.

In the surface state monitoring method according to the present embodiment, an allowance range of the incident angle of infrared radiation on the end surface 6 is 68–78° as described above, and an allowable range of the incident position changes corresponding to an incident angle of infrared radiation as shown in Table 2.

TABLE 2

| Incident Angle | Angle of Substrate Flat surface to Ray | Allowable Range of Incidence Position |
|---|---|---|
| 68.0° (Min. Angle) | 46.0° | 0~580.63 μm |
| 73.3° (Brewster Angle) | 51.7° | 0~500.56 μm |
| 78.0° (Max. Angle) | 56.0° | 0~443.04 μm |

However, in accordance with the specifications of the 300 mm diameter silicon wafer which is discussed here, as shown in FIG. 17, the end surface 6 is formed in a chamfer formed on the boundary between the substrate surfaces 3, 4 and the outer peripheral surface 5, and a total horizontal length thereof is stipulated to be below 500 μm.

That is, in a case that the surface state monitoring method according to the present embodiment is applied to the silicon wafer having the above-described specifications, if infrared radiation is incident on the end surface 6 at the optimum angle, 73.7°, it is not necessary to consider an incident angle thereof. In order to maximize a detected area of the substrate surfaces 3, 4 of the silicon wafer, it is preferable to set an incident position of infrared radiation near the outer edge of the end surface 6.

In the present embodiment, infrared radiation is incident at the angle of +73.7° on the end surface 6 which is declined by 22° in plane which is perpendicular to the substrate surface 3 of a substrate-to-be-monitored 12 and passes the center, but it is possible that the incident angle is about −73.7°.

Also in the latter embodiment, the surface state monitoring apparatus has the same constituent members as the surface state monitoring apparatus according to the former embodiment and is different from the latter only in arrangement of the infrared radiation condensing means 30, 40. In the surface state monitoring method according to the latter embodiment, as shown in FIG. 22, infrared radiation is incident at the angle of −73.7° on the end surface 6 declined at 22° in plane which is perpendicular to the end surface 3 of a substrate-to-be-monitored 12 and passes the center and is incident on a position spaced by about 0–80.18 μm from the boundary between the end surface 6 and the substrate surface 3.

Also in the latter embodiment in which an incident angle of infrared radiation is −73.7°, an allowable range of the incident angle of infrared radiation can be set as in the former embodiment. As shown in Table 3 shown below, an allowable range of the incident position change corresponding to an incident angle of infrared radiation.

TABLE 3

| Incident Angle | Angle of Substrate Flat surface to Ray | Allowable Range of Incidence Position |
|---|---|---|
| −68° (Min. Angle) | 90° | None (0 μm) |
| −68.207° | 89.793° | 3 μm (about focus diameter of infrared radiation) |
| −73.3° (Brewster Angle) | 84.3° | 0~80.18 μm |
| −78° (Max. Angle) | 80° | 0~137.57 μm |

However, as shown in Table 3 shown above, in a case that a substrate-to-be-monitored 12 has a 775 μm-thick, and the end surface 6 is declined by 22°, a proper incident position is unavailable when an incident angle of infrared radiation is −68°. It is preferable that an incident angle of infrared radiation is above −68.207° irrespective of energy reflectivity.

Also in the present embodiment having an incident angle of infrared radiation of about −73.7°, the above-described incident angle and allowable range thereof are satisfied, whereby infrared radiation incident on the end surface 6 of a substrate-to-be-monitored 12 is prohibited from being reflected on the end surface 7, resultantly lowering resolving power for the detection, and presence of organic contamination on the substrate surfaces 3, 4 can be judged well.

As shown in FIG. 17, when an incident angle of infrared radiation incident on the end surface 6 of a substrate-to-be-monitored 12 is +73.7°, a reflection angle inside the substrate-to-be-monitored 12 is 51.7°, but as shown in FIG. 22, when an incident angle is −73.7°, a reflection angle inside the substrate-to-be-monitored is 84.3°. Thus, the embodiment using an incident angle of −73.7° has higher resolving power for the detection than the embodiment using an incident angle of +73.7°.

However, in a case that infrared radiation is caused to undergo multiple reflection inside a substrate-to-be-monitored 12, reflectivities also inside the substrate-to-be-monitored must be considered. That is, as shown in FIG. 5, a reflectivity depends on a reflection angle. When infrared radiation is reflected inside a substrate-to-be-monitored 12 placed in air, high energy reflectivity can be obtained when a residual ray exit angle which is a reflection angle inside the substrate-to-be-monitored is above 72°, and when a residual ray exit angle is 74–90°, the energy reflectivity lowers to below 0.3.

That is, when an incident angle is −73.7° as shown in FIG. 22, a residual ray exit angle is 84.3°, and the energy reflectivity lowers. Loss of infrared radiation due to transmission when the infrared radiation is caused to undergo internal multiple reflection on the substrate surfaces 3, 4 of the substrate-to-be-monitored 12 is large. Accordingly, in a case that energy efficiency for the detection is important, it is suitable that, as shown in FIG. 17, an incident angle of infrared radiation incident on the end surface 6 of the substrate-to-be-monitored 12 is +73.7°. In a case that resolving power for the detection is important it is suitable that, as shown in FIG. 22, an incident angle is −73.7°.

Even though an incident angle infrared radiation incident on the end surface 6 of a substrate-to-be-monitored 12 is −73.7°, a residual ray exit angle is 40.3° when the infrared radiation is reflected on the end surface 7. The resolving power will be in an allowable range for products, and in order to realize such surface state monitoring method infrared radiation having a −73.7° incident angle is incident on a position spaced by more than 80.18 μm from the boundary between the end surface 6 and the substrate surface 3.

As described above, according to the present embodiment, reflection loss at the time that infrared radiation enters a substrate-to-be-monitored can be trivial, whereby infrared radiation can be applied into the substrate-to-be-monitored through the end surface. As a result, presence/absence of defects on the surfaces of a substrate-to-be-monitored can be detected with good energy efficiency.

[A Fourth Embodiment]

The surface state monitoring method and apparatus according to a fourth embodiment of the present invention will be explained with reference to FIGS. 24 to 27. The same reference numbers of the present embodiment as those of the surface state monitoring method and apparatus according to the first or the second embodiment shown in FIGS. 1 to 16 are represented by the same reference numbers not to repeat or to simplify their explanation.

Figure 24:
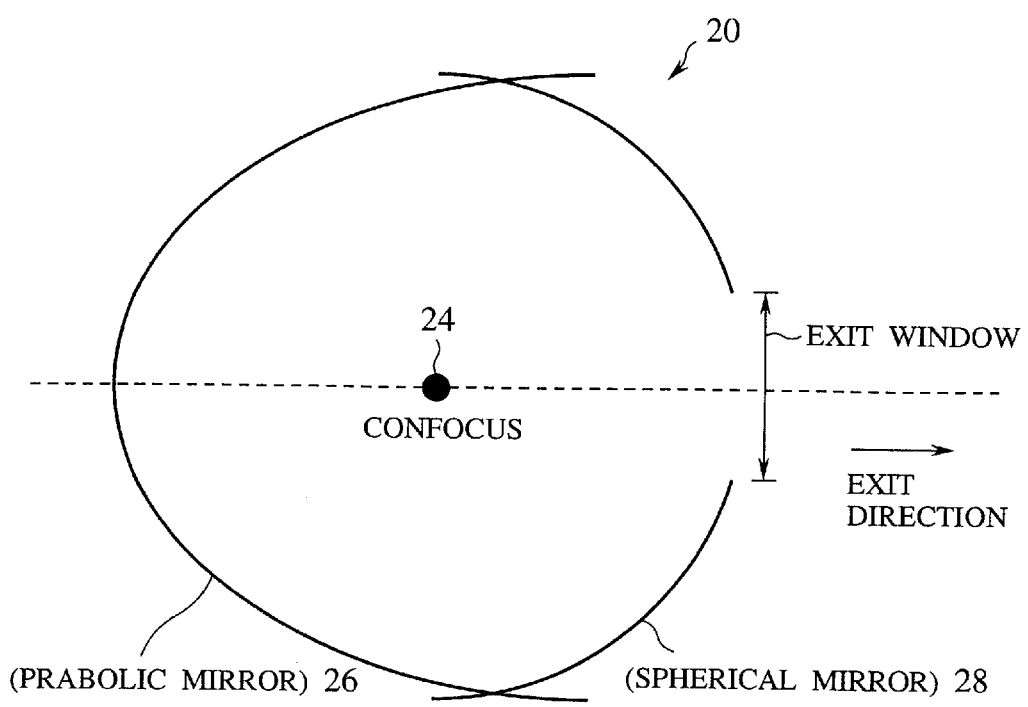
FIG. 24 is a diagrammatic view of a first infrared radiation source according to a fourth embodiment of the present invention, which shows a structure thereof.
Figure 25A:
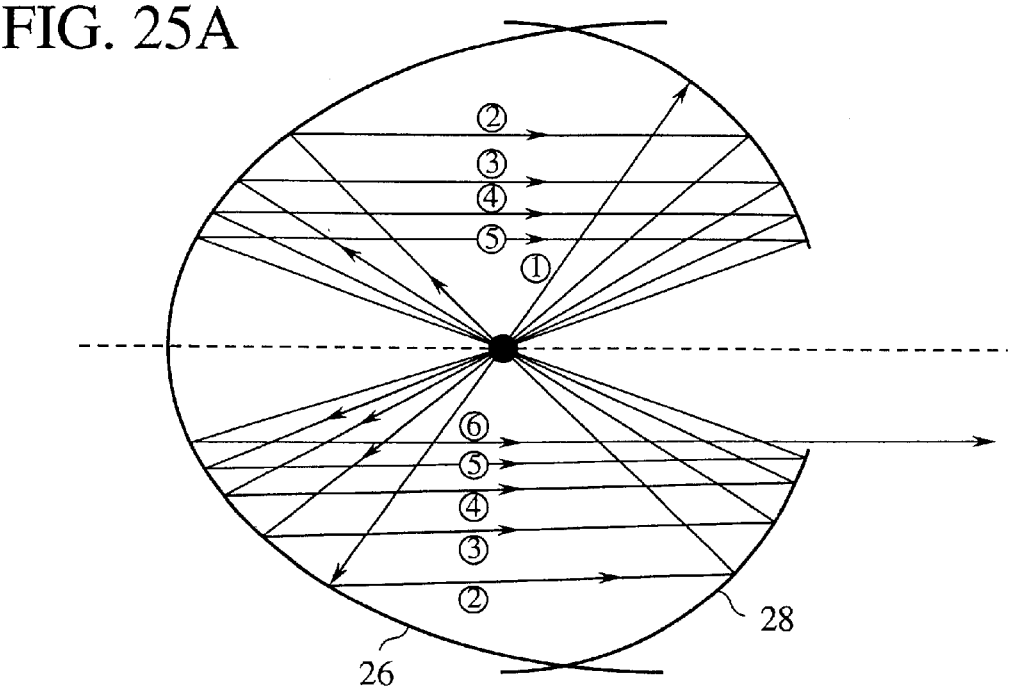
FIGS. 25A and 25B are views explaining an operation of the infrared radiation source shown in FIG. 24.
Figure 25B:
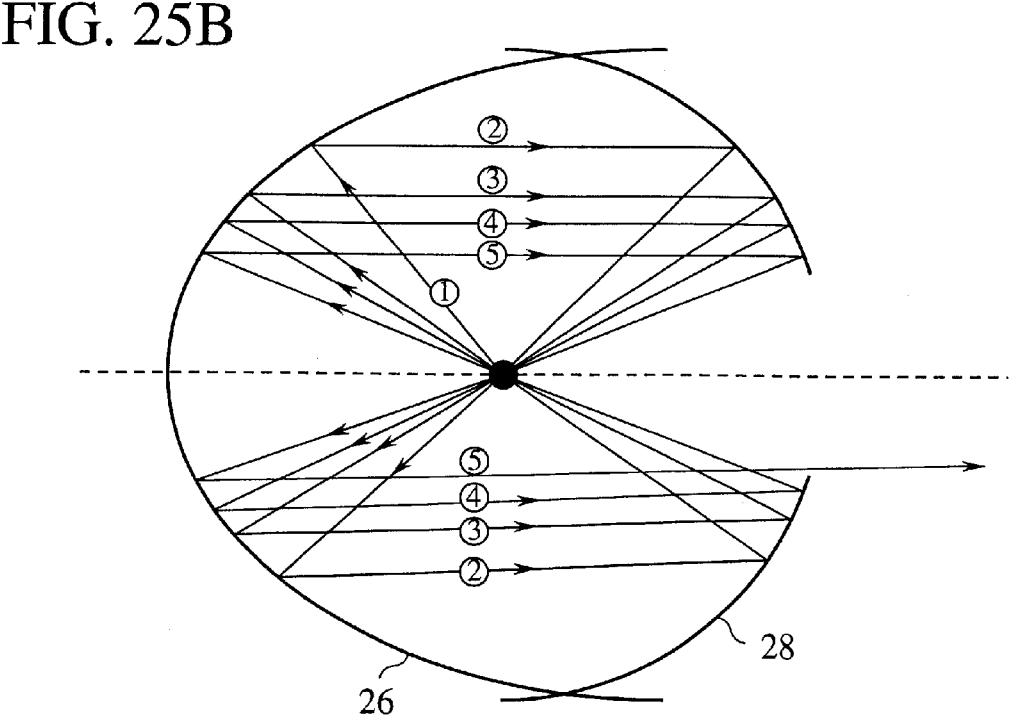
Figure 26:
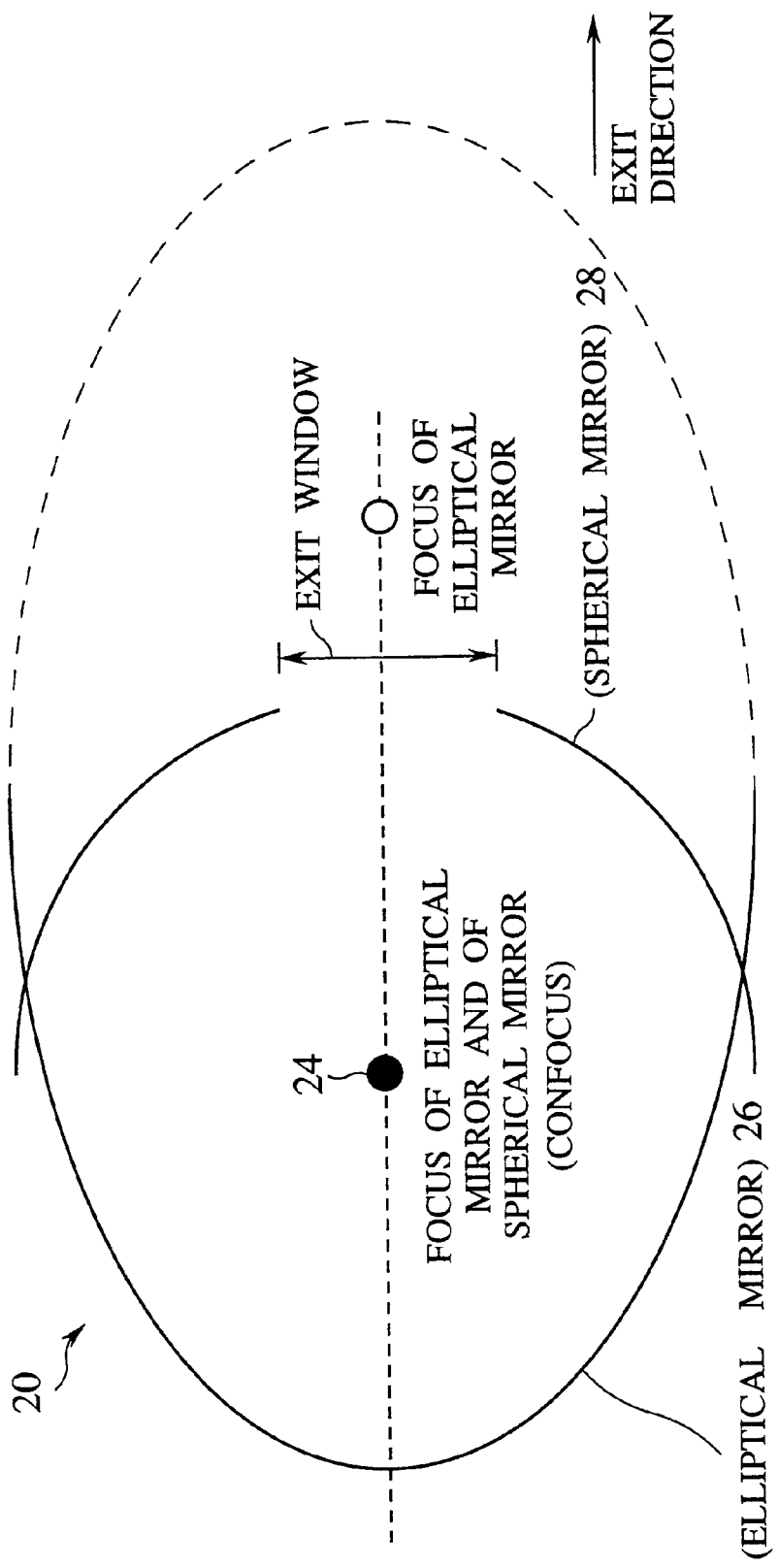
FIG. 26 is a diagrammatic view of a second infrared radiation source according to the fourth embodiment of the present invention, which shows a structure thereof.
Figure 27:
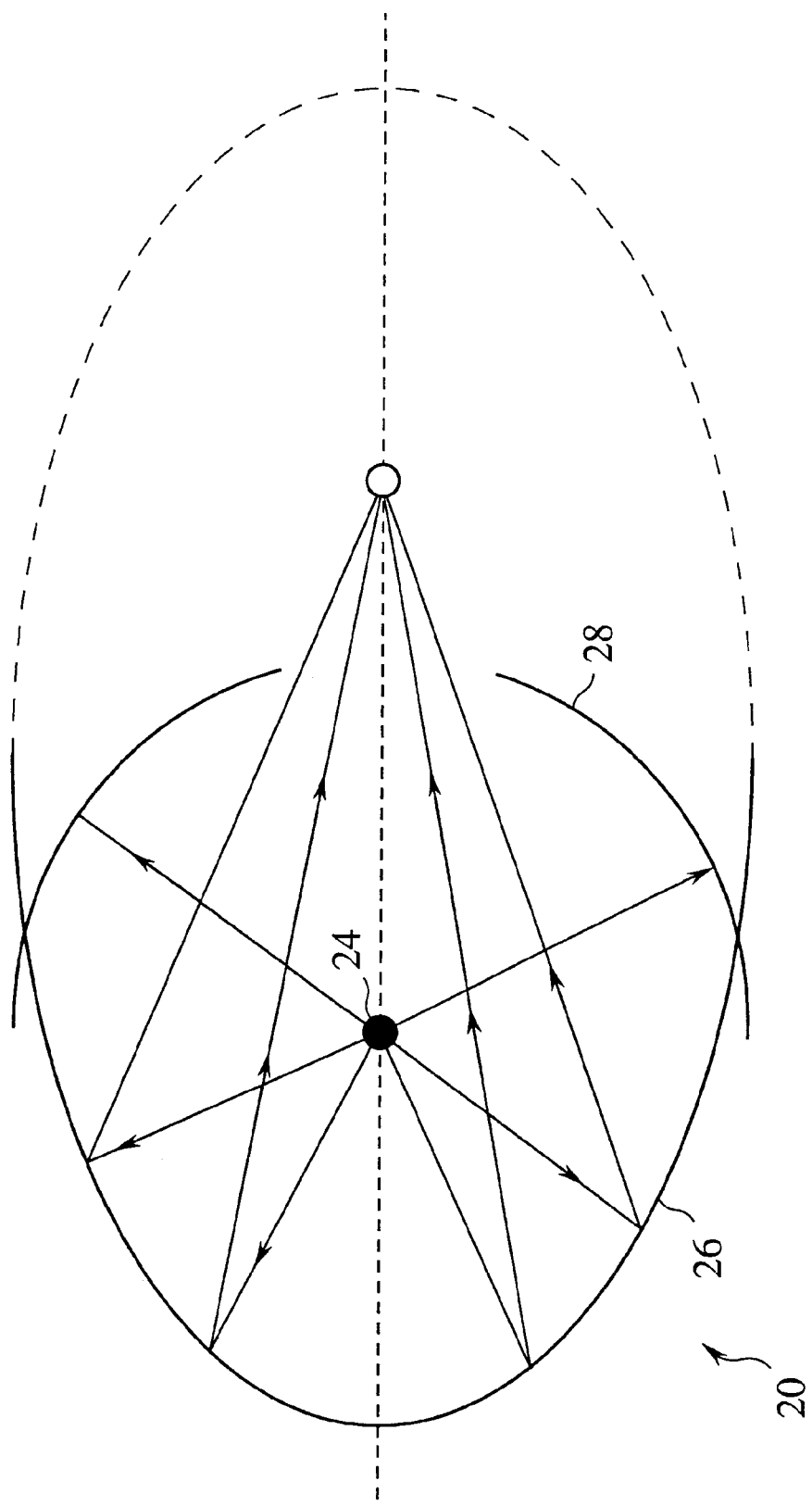
FIG. 27 is a view explaining an operation of the infrared radiation source shown in FIG. 26.

FIG. 24 is a diagrammatic view of a first infrared radiation source according to the present embodiment, which shows a structure thereof. FIGS. 25A and 25B are views explaining an operation of the infrared radiation source shown in FIG. 24. FIG. 26 is a diagrammatic view of a second infrared radiation source according to the present embodiment, which shows a structure thereof. FIG. 27 is a view explaining an operation of the infrared radiation source shown in FIG. 26.

In the present embodiment, infrared radiation sources other than the infrared radiation sources used in the surface state monitoring method and apparatus according to the first and the second embodiments, which are suitable for the surface state monitoring method and apparatus according to the first and the second embodiment will be explained.

In the surface state monitoring method and apparatus according to the first and the second embodiments the front reflecting plate 28 and the rear reflecting plate 26 can have various forms in accordance with characteristics required of the infrared radiation source 20.

As a first approach to a variation of the infrared radiation source 20, for higher freedom degree of design of the optical system of the spectroscope it is considered to increase light amount of parallel rays as the light source. Parallel rays as the light source is preferable because of high freedom degree of the following optical processing. One means for simply increasing a total radiation amount is charging much current to filaments, but has a disadvantage that the filaments do not last long although parallel rays are increased.

In the first infrared radiation source according to the present embodiment, as shown in FIG. 24, the rear reflecting plate 26 is formed of a parabolic mirror, and the front reflecting mirror is formed of a spherical mirror. Furthermore, the rear reflecting plate 26 and the front reflecting plate 28 are opposed to each other with a focus of the parabolic mirror aligned with that of the spherical mirror, and a light source 24 is positioned at the confocus.

In this arrangement of the rear reflecting mirror 26 and the front reflecting mirror 28, that of rays emitted forward by the light source 24 positioned at the confocus, which has high parallelism and is not blocked by the front reflecting plate 28 exits directly through an exit window. The rest of the rays reflected by the front reflecting plate 28 in the form of a spherical mirror repeats reflection on the front reflecting plate 28 and the rear reflecting plate 26 and transformed into parallel rays advancing forward, and exit as parallel rays through the exit window.

For example, as shown in FIG. 25A, light (1) emitted by the light source 24 positioned at the confocus toward above the front reflecting plate 28 is reflected on the front reflecting plate 28 and passes again the confocus to be reflected on the rear reflecting plate 26, and is transformed into parallel rays (2). The parallel rays (2) repeat reflection a plurality of times between the front and the rear reflecting plates 28, 26 (rays (3)–(5) in the drawing), then arrive at the exit window (rays (6) in the drawing), and exit through the exit window. Thus, the front reflecting plate 28 has the function of reflecting back to the rear reflecting plate 26 that of light emitted forward by the light source 24, which does not contribute to parallel rays, and transforming the same into parallel rays, and also the function admitting parallel rays alone to exit, which are necessary for the measurement, shutting off unnecessary light (stray light).

Light emitted rearward by the light source 24 positioned at the confocus is reflected by the rear reflecting plate 26. That of the reflected light which is not shut off by the front reflecting plate 28 exit through the exit window. That of the reflected light, which is reflected by the front reflecting plate 28 repeats reflection on the front and the rear reflecting plates 28, 26, then is transformed into parallel rays advancing forward and exits through the exit window as the parallel rays.

For example, as shown in FIG. 25B, rays (1) emitted toward above the rear reflecting plate 26 by the light source 24 positioned at the confocus are reflected by the rear reflecting plate 26 and transformed into parallel rays (2). The parallel rays (2) are reflected by the front reflecting plate 28, pass the confocus, and are again reflected by the rear reflecting plate 26 to be transformed into parallel rays (2). Then the parallel rays (2) repeat reflection a plurality of times between the front reflecting plate 28 and the rear reflecting plate 26 (rays (3)–(5) in the drawing) and arrive at the exit window, and exit through the exit window. Thus, the front reflecting plate 28 has the function of returning back to the rear reflecting plate 26 that of light emitted forward by the light source, which does not contribute to parallel rays to transform the same into parallel rays, and also the function of admitting parallel rays alone to exit, which are necessary for the measurement, shutting off unnecessary light (stray light).

The rear reflecting plate 26 and the front reflecting plate 28 are thus arranged, whereby light emitted by the filaments can be transformed into parallel rays, and generation of stray light can be prevented.

As a second approach, for higher detection sensitivity of the spectroscope, it is considered to efficiently condense light from the light source to one point so as to increase a light amount. It is also considered to charge much current to the filaments simply for an increased radiation amount, but with a disadvantage that the filaments do not last long.

Then, in the second infrared radiation source according to the present embodiment, as shown in FIG. 26 the rear reflecting plate 26 is provided by an elliptical mirror, and the front reflecting plate 28 is provided by a spherical mirror. The rear reflecting mirror 26 and the front reflecting mirror 28 are opposed to each other so that one focus of the elliptical mirror (left side in the drawing) and the focus of the spherical mirror agree with each other. The light source 24 is positioned at the confocus. The rear reflecting plate 26 and the front reflecting plate 28 are thus arranged so that light emitted by the light source 24 can be efficiently condensed at the other focus of the elliptical mirror constituting the rear reflecting mirror 26.

That is, the rear reflecting plate 26 and the front reflecting plate 28 are thus arranged, whereby as shown in FIG. 27, light emitted by the light source 24 positioned at the confocus to the rear reflecting plate 26 is reflected on the rear reflecting plate 26, exits through the exit window of the front reflecting plate 28 and is condensed to the other focus of the elliptical mirror. Light emitted by the light source 24 to the front reflecting plate 28 is reflected on the front reflecting plate 28, passes the confocus, is reflected on the rear reflecting plate 26, exit through the exit window of the front reflecting plate 28, and is condensed to the other focus of the elliptical mirror. Thus, the front reflecting mirror 28 has the function of reflecting that of the light emitted toward the front by the light source, which has not been condensed back to the rear reflecting plate 26 to condense the light to the other focus of the elliptical mirror, and also the function of admitting light alone necessary for the measurement to exit, shutting off stray light.

The rear reflecting plate 26 and the front reflecting plate 28 are thus arranged, whereby light emitted by the light source 24 in random direction can be efficiently condensed to the other focus of the elliptical mirror, and the generation of stray light can be suppressed.

As described above, according to the present embodiment, the rear reflecting plate 26 is provided by a parabolic mirror or an elliptical mirror, and the front reflecting mirror 28 is provided by a spherical mirror, whereby light emitted by the light source 24 can be efficiently transformed into parallel rays or can be condensed to one point. The radiation thus made available is suitable to be used in the surface state monitoring method and apparatus according to the first and the second embodiments.

In the present embodiment, light emitted by the light source 24 is transformed into parallel rays or is condensed to one point, but it is possible that emitting light is transformed into parallel rays by the infrared radiation source 20 shown in FIG. 24, and the parallel rays are condensed by a condenser lens or others to be used. It is also possible that emitted light is condensed by the infrared radiation source 20 shown in FIG. 26 and transformed into parallel rays by a condenser lens, or others.

As described in the first embodiment, the exit window of the front reflecting plate 28 may be covered with an infrared radiation transmitting material to make the infrared radiation source explosion-proofed.

[A Fifth Embodiment]

The surface state monitoring method and apparatus according to a fifth embodiment of the present invention will be explained with reference to FIGS. 28 to 30. The same members of the present embodiment as those of the surface state monitoring method and apparatus according to the first or the second embodiment are represented by the same reference numbers not to repeat or to simplify their explanation.

Figure 28:
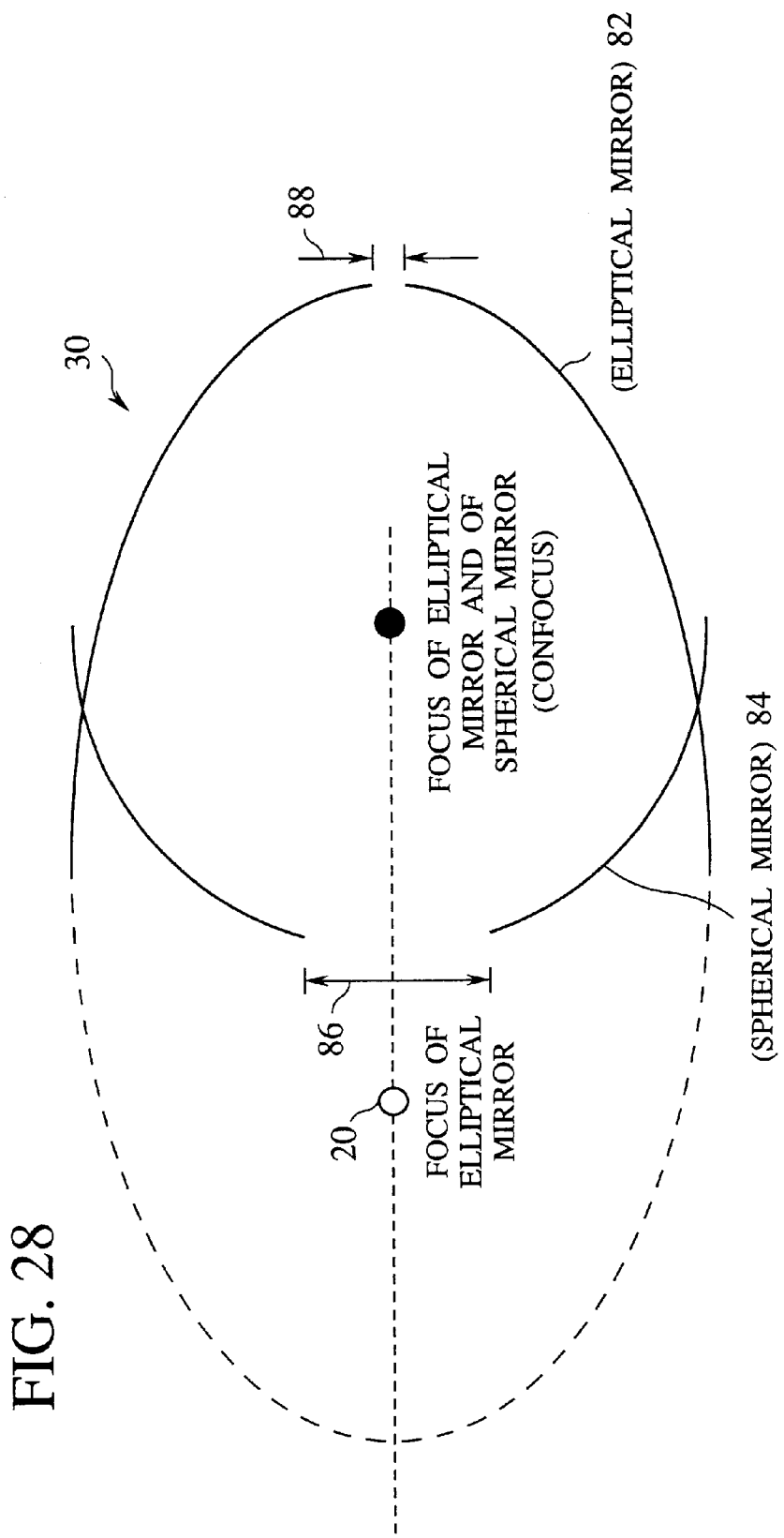
FIG. 28 is a diagrammatic view of infrared radiation condensing means according to a fifth embodiment of the present invention, which shows a structure thereof.

FIG. 28 is a diagrammatic view of infrared radiation condensing means according to the present embodiment, which show a structure thereof. FIG. 29 is a view explaining an operation of the infrared radiation condensing means shown in FIG. 28. FIGS. 30A and 30B are views explaining advantageous effects of the infrared radiation condensing means according to the present embodiment.

In the present embodiment, other infrared radiation condensing means which is suitable to be used in the surface state monitoring method and apparatus according to the first and the second embodiments will be explained.

As shown in FIG. 28, the infrared radiation condensing means 30 according to the present embodiment comprises an elliptical mirror 82 and a spherical mirror 84. The elliptical mirror 82 and the spherical mirror 84 are opposed to each other with one (right side in the drawing) of the focuses of the elliptical mirror 82 and the focus of the spherical mirror 84 aligned with each other. An entrance window 86 for infrared radiation to enter through is formed in the center of the spherical mirror 84. A slit 88 is formed in the center of the spherical mirror 84 for inserting an object-to-be-monitored.

Then, an operation of the infrared radiation condensing means shown in FIG. 28 will be explained with reference to FIG. 29.

Figure 29:
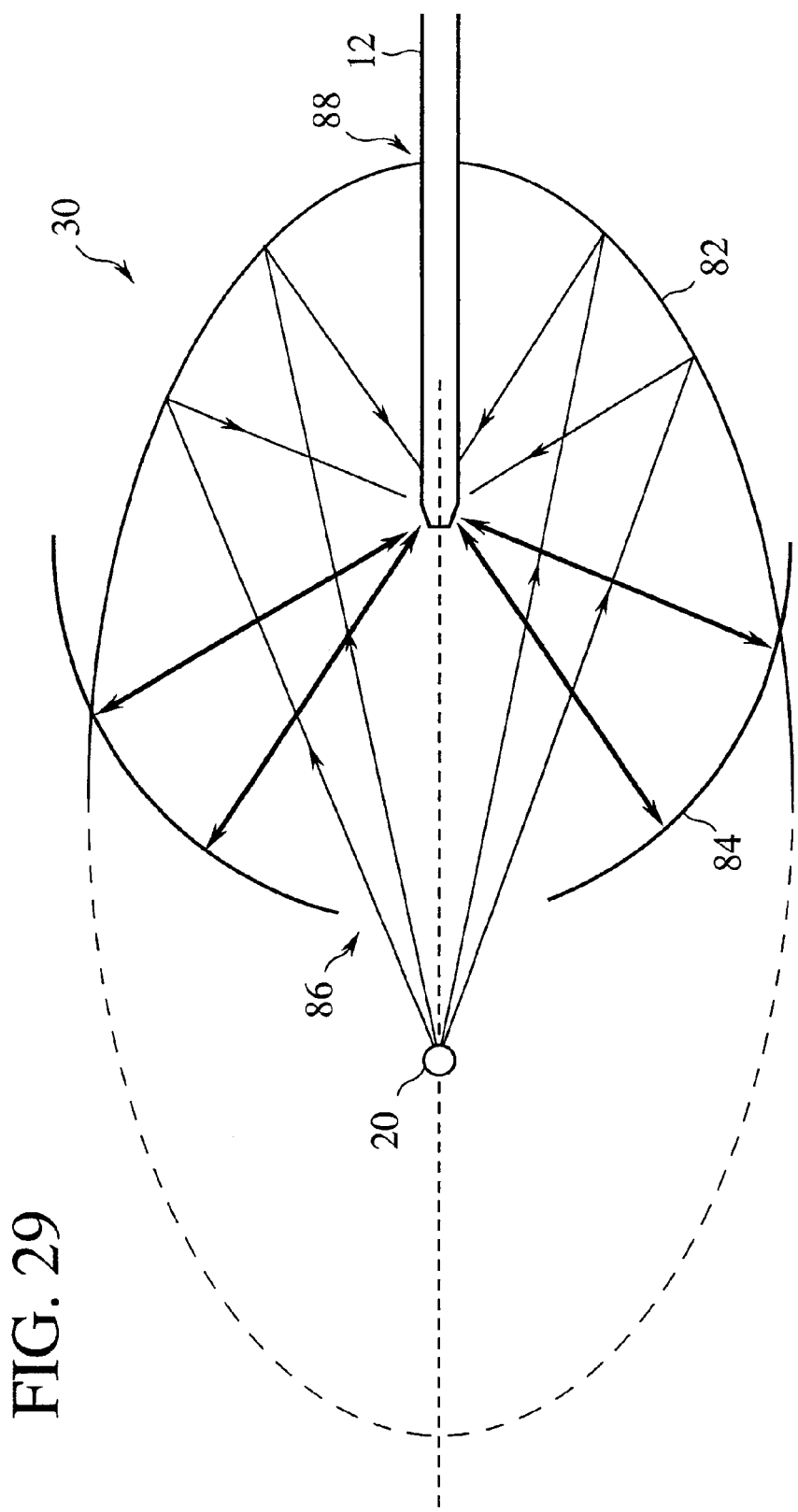
FIG. 29 is a view explaining an operation of the infrared radiation condensing means shown in FIG. 28.
Figure 30A:
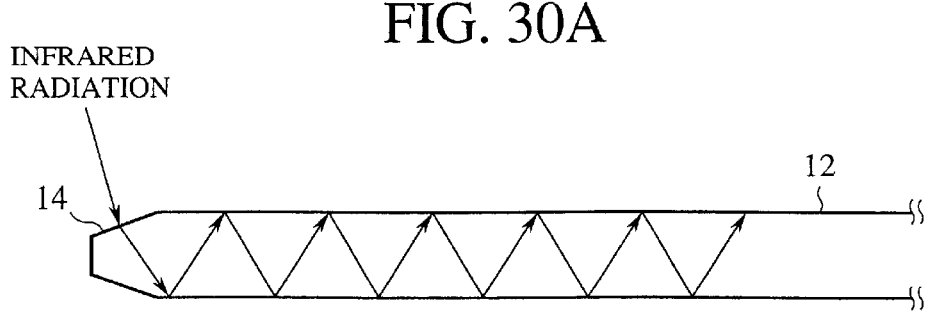
FIGS. 30A and 30B are views explaining effects of the infrared radiation condensing means according to the fifth embodiment of the present invention.
Figure 30B:
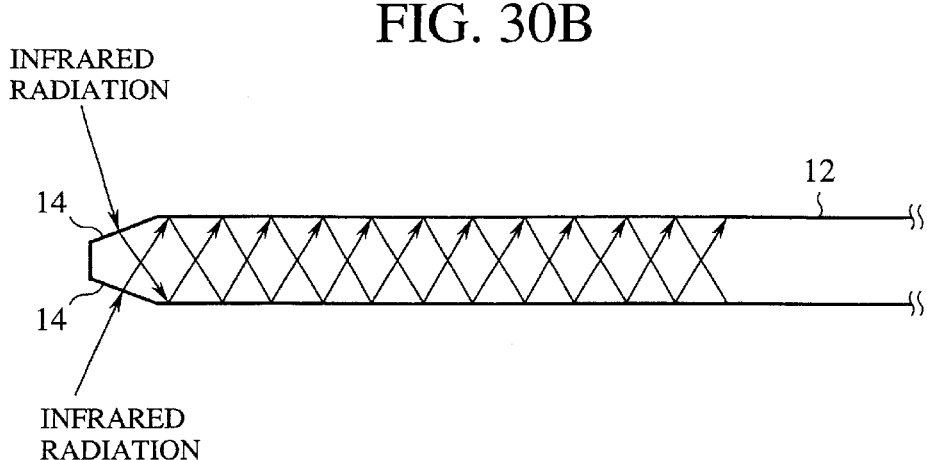

As shown in FIG. 29, a substrate-to-be-monitored 12 is inserted into the infrared radiation condensing means 30 with the end surface (the declined part 14) thereof for infrared radiation to be incident on position at a confocus with respect to the elliptical mirror 82 and the spherical mirror 84. Infrared radiation source 20 for applying infrared radiation to the infrared radiation condensing means 30 through the entrance window 86 of the spherical mirror 84 is disposed at the other focus (left side in the drawing) of the elliptical mirror 82.

The infrared radiation source 20 can apply to the infrared radiation condensing means 30 light which is equivalent to light applied by a spot light source positioned at the other focus of the elliptical mirror 82. This is achieved, e.g., by positioning a spot light source at the other focus of the elliptical mirror 82 or by positioning the infrared radiation source so that a focus of required light when the light is condensed is positioned the other focus of the elliptical mirror 82. The latter infrared radiation source can be provided by, e.g., the infrared radiation source according to the fourth embodiment shown in FIG. 26.

Such arrangement of the incidence optical system of infrared radiation enables infrared radiation emitted by the infrared radiation source 20 to enter the infrared radiation condensing means 30 through the entrance window 86 of the spherical mirror 84 and be condensed to the confocus by the elliptical mirror 82. Infrared radiation condensed at the confocus passes the confocus and reaches the spherical mirror 84, and the infrared radiation reflected by the spherical mirror 84 is incident on the end surface (declined surface 14) of a substrate-to-be-monitored 12.

Such arrangement of the incidence optical system of infrared radiation enables infrared radiation to be incident both on the declined part 14 of the front surface of the substrate-to-be-monitored and on the declined part 14 on the back side thereof. Accordingly, a total amount of infrared radiation introduced into the substrate-to-be-monitored can be increased, whereby information of molecular vibrations on a substrate-to-be-monitored 12 in a larger surface area can be obtained.

That is, in the surface state monitoring method and apparatus according to the first and the second embodiments, as shown in FIG. 30 only infrared radiation which has been incident on the declined part 14 on the surface of a substrate-to-be-monitored 12 undergoes multiple reflection in the substrate-to-be-monitored 12 and probes states of the surfaces of the substrate. By the use of the infrared radiation condensing means according to the present embodiment, as shown in FIG. 30B infrared radiation which has been incident on the declined part 14 of the back side of the substrate-to-be-monitored 12 also undergoes multiple reflection in the substrate-to-be-monitored 12 and proves states of the surfaces of the substrate. An effective area on the substrate-to-be-monitored, in which organic contaminants are detected can be larger, and higher detection sensitivity can be obtained.

As described above, the infrared radiation condensing means 30 according to the present embodiment can condense infrared radiation on the declined parts 14 of the front and the back sides of a substrate-to-be-monitored, whereby higher detection sensitivity for detecting contaminants on the surfaces of the substrate-to-be-monitored 12 can be obtained. Higher detection sensitivity for detecting contaminants can prevent, for example, dielectric breakdown and insulation deterioration of gate oxide films, and higher fabrication yields can be obtained.

In the present embodiment, the infrared radiation condensing means 30 is arranged to be able to condense infrared radiation on the declined parts 14 of the front and the back sides of a substrate-to-be-monitored 12, whereby the infrared radiation is incident on the declined parts 14 of the front and the back sides of the substrate-to-be-monitored 12. In the surface state monitoring method and apparatus according to the first embodiment, it is possible that the infrared radiation source and the infrared radiation condensing means are additionally provided for making infrared radiation incident on the declined part 14 of the back side of the substrate-to-be-monitored 12, so that infrared radiation is incident on the declined part 14 of the front and the back sides of the substrate-to-be-monitored 12.

[A Sixth Embodiment]

The surface state monitoring method and apparatus according to a sixth embodiment will be explained with reference to FIGS. 31 to 33. The same members of the present embodiment as those of the surface state monitoring method and apparatus according to the first or the second embodiment shown in FIGS. 1 to 16 are represented by the same reference numbers not to repeat or to simplify their explanation.

Figure 31:
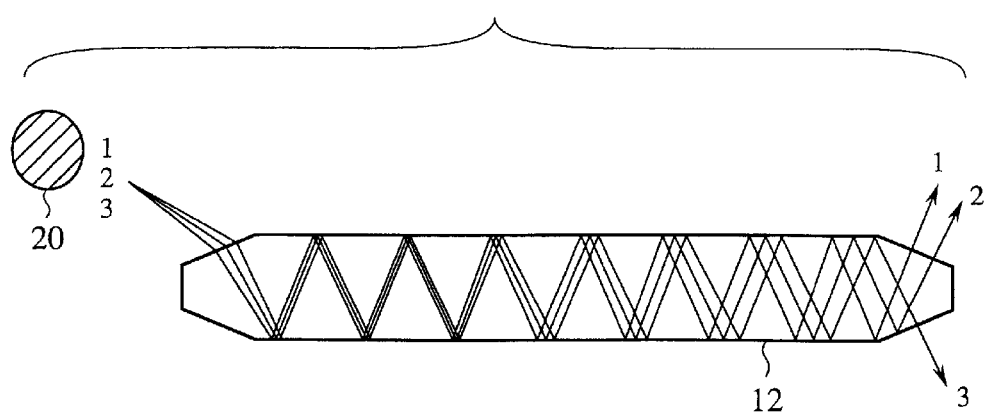
FIG. 31 is a view explaining an optical path of infrared radiation which are entered a substrate-to-be-monitored.

FIG. 31 is a view explaining an optical path of infrared radiation entering a substrate-to-be-monitored. FIG. 32 is a view showing relationships between positions of a substrate-to-be-monitored with respect to the infrared radiation condensing means, and infrared radiation paths. FIG. 33 is a diagrammatic view of the infrared radiation condensing means according to the present embodiment, which show a structure thereof. FIG. 34 is a view explaining an operation of the infrared radiation condensing means shown in FIG. 33.

As shown in FIG. 31, infrared radiation which has been condensed by the infrared radiation condensing means and incident on a substrate-to-be-monitored 12 has emission angles having a certain divergence. Accordingly, incident angles of infrared radiation incident on the end surface (the declined part 14) of the substrate-to-be-monitored 12 a little vary depending on positions of rays. In FIG. 31 rays are, e.g., three rays 1, 2, 3 which are incident on the substrate-to-be-monitored 12 at decreased incident angles in the numerical order.

The internal reflection of infrared radiation incident on a substrate-to-be-monitored 12 is determined by an incident angle of the infrared radiation on the end surface of the substrate-to-be-monitored 12. In the case of FIG. 31 the ray 3 has a largest internal reflection angle. A distance over which a ray travels by once internal reflection is longer as the reflection angle is larger. In comparison with the ray 1 with the ray 3, the ray 3 travels farther by the same number of internal reflection times than the ray 1.

Accordingly, in the case of FIG. 31, the ray 1 of infrared radiation arrives at the end surface of the upper side of the substrate-to-be-monitored 12. The ray 3 arrives at the end surface of the back side of the substrate-to-be-monitored 12, and that of the infrared radiation, which has been transmitted by the end surface of the back side is emitted below the substrate-to-be-monitored 12. That of the ray 3 passing through the end surface of the back side cannot be detected by the surface state monitoring apparatus shown in FIG. 1. In a case that the infrared radiation condensing means 30 according to the fifth embodiment is applied, even when incident infrared radiation has one and the same optical path, the infrared radiation exits through both end surfaces.

Figure 32:
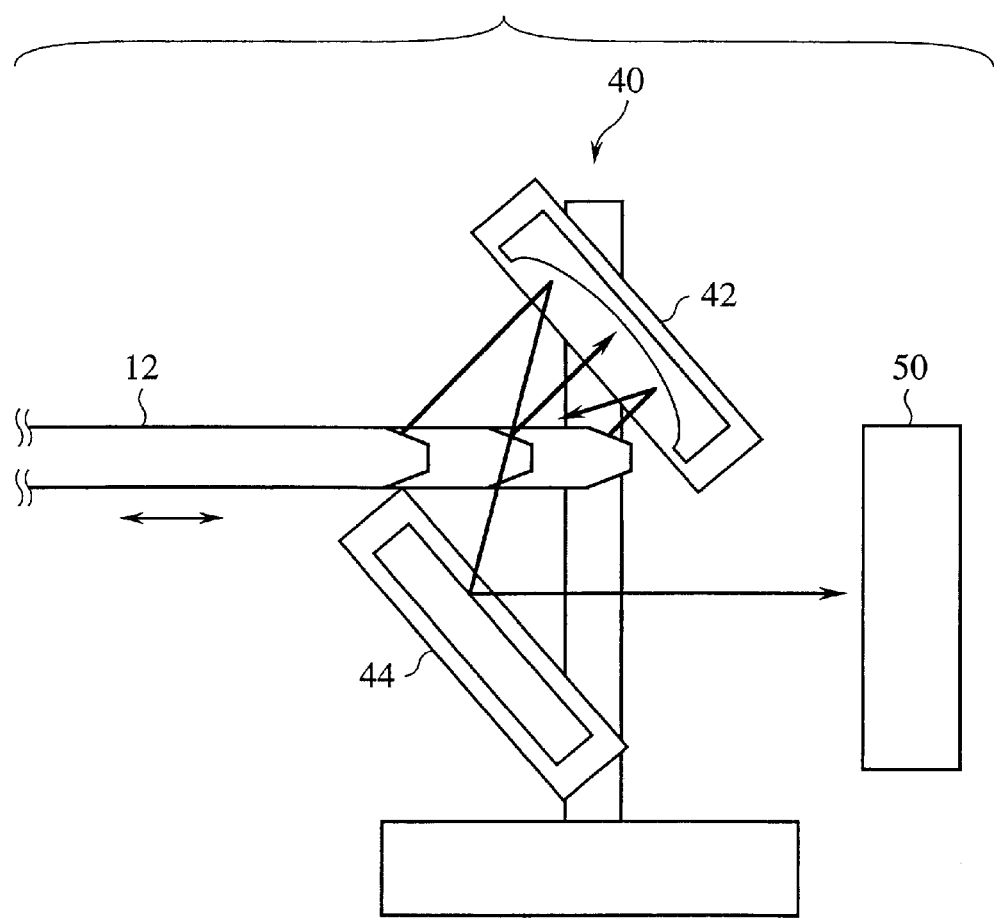
FIG. 32 is a view of relationships between positions of a substrate-to-be-monitored with respect to the infrared radiation condensing means, and an infrared radiation optical path in the surface state monitoring apparatus shown in FIG. 1.

In the surface state monitoring apparatus shown in FIG. 1, when a positional relationship between the infrared radiation condensing means 40 and a substrate-to-be-monitored 12 is changed as shown in FIG. 32, it is often a case that infrared radiation exiting the substrate-to-be-monitored 12 cannot be detected by the infrared radiation detector 50 as cannot be detected when the substrate-to-be-monitored 12 is at, e.g., either of the right two positions in FIG. 32. In order to make the exiting infrared radiation in this state, it is necessary to displace the position of the substrate-to-be-monitored 12 to a suitable position or adjust a position of the substrate-to-be-monitored with respect to positions of the concave mirror 42 and the reflecting mirror 44.

Under these circumstances infrared radiation condensing means which can introduce into the infrared radiation detector 50 infrared radiation exiting the end surfaces of the front and the back sides of the substrate-to-be-monitored 12 and is accordingly invulnerable to affection of a position of a substrate-to-be-monitored 12 with respect to the infrared radiation condensing means 40 is desired.

In the present embodiment infrared radiation condensing means which can condense infrared radiation exiting outside through both the declined part of the front and the declined part of the back side of a substrate-to-be-monitored 12 to introduce the infrared radiation into the infrared radiation detector will be explained.

In the fifth embodiment, the infrared radiation condensing means is constituted by the elliptical mirror 82 and the spherical mirror 84 as shown in FIG. 28 and is used as the infrared radiation condensing means 30 as the incidence optical system of the surface state monitoring method and apparatus according to the first and the second embodiments. The optical system shown in FIG. 28 can be used as the infrared radiation condensing means 40 as the exit optical system of the surface state monitoring method and apparatus according to the first or the second embodiment in the same way as in the fifth embodiment.

Figure 33:
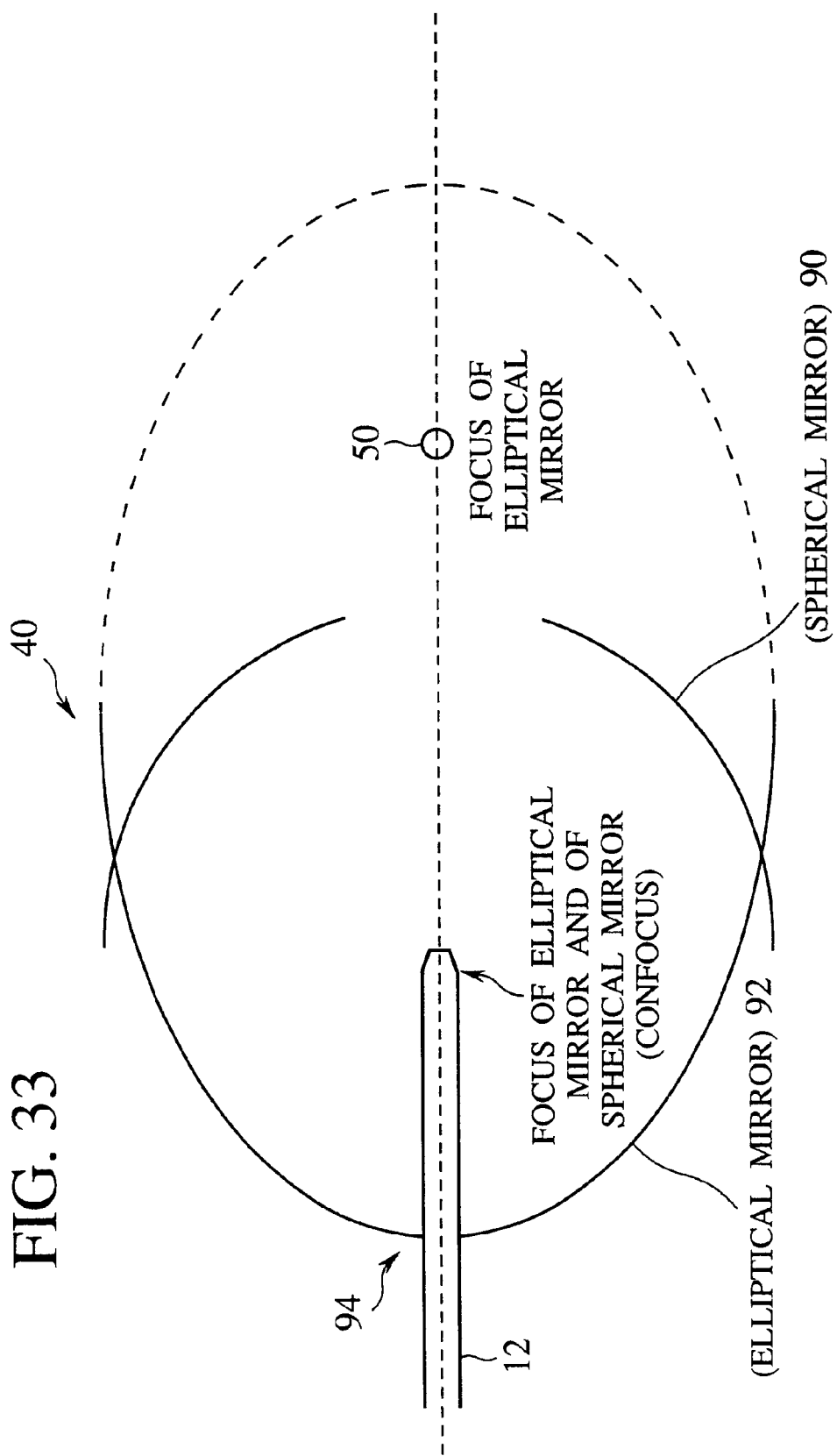
FIG. 33 is a diagrammatic view of infrared radiation condensing means according to a sixth embodiment of the present invention, which shows a structure thereof.
Figure 34:
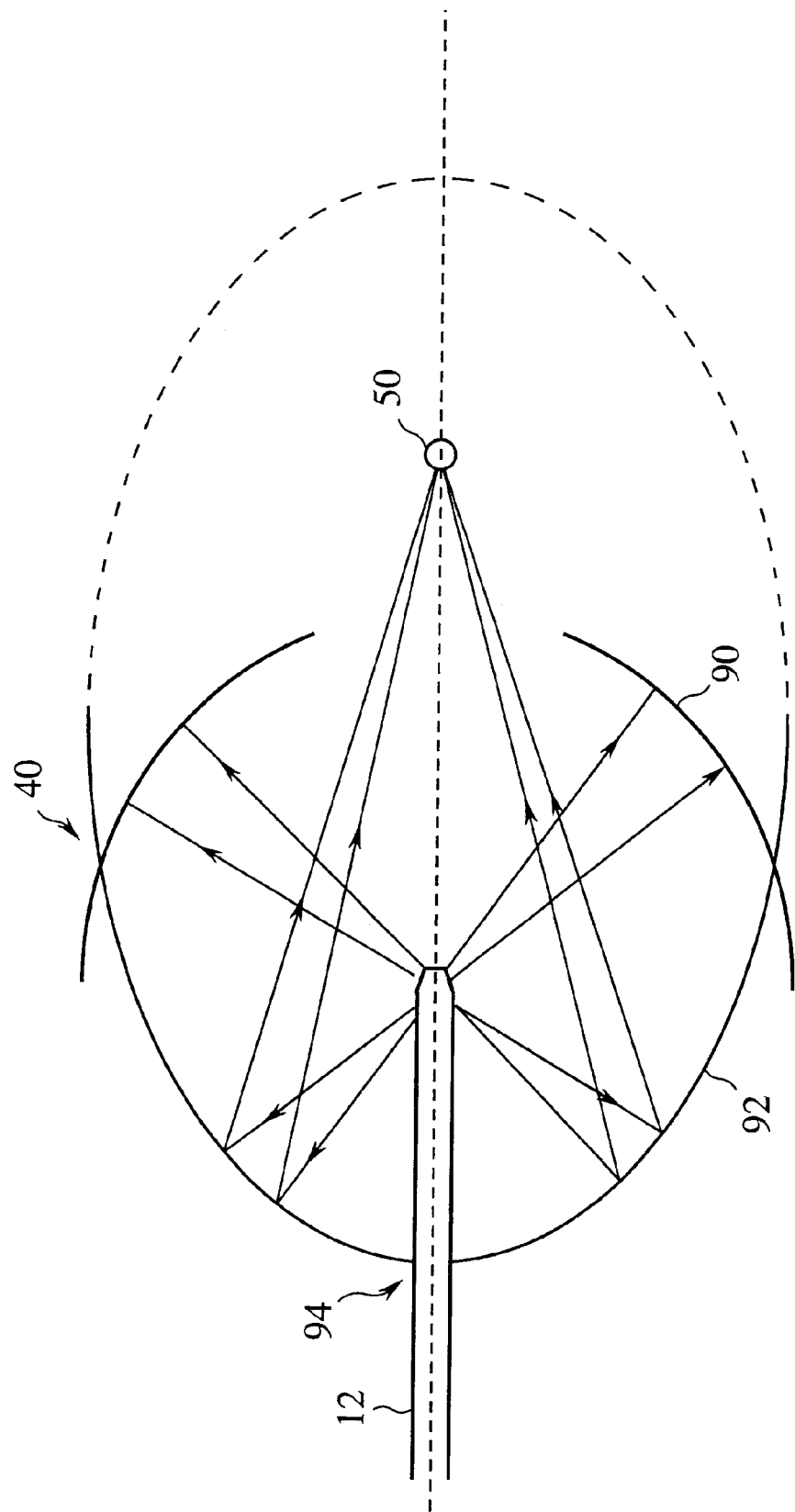
FIG. 34 is a view explaining an operation of an infrared radiation condensing means shown in FIG. 33.

In the surface state monitoring method and apparatus according to the present embodiment, the infrared radiation condensing means 40 of the surface state monitoring method and apparatus according to the first and the second embodiments is constituted by a spherical mirror 90 and an elliptical mirror 92 as shown in FIG. 33.

As shown in FIG. 33, a substrate-to-be-monitored 12 is inserted into the infrared radiation condensing means 40 through a slit 94 formed in the elliptical mirror 92 so that the end surface (a declined part 14) through which infrared radiation exits is positioned at confocus of the elliptical mirror 92 and the spherical mirror 90. An infrared radiation detector 50 for detecting infrared radiation condensed by infrared radiation condensing means 40 is positioned at the other focus (on the right side in the drawing) of the elliptical mirror 92.

In place of positioning the infrared radiation detector 50 at the other focus of the elliptical mirror 92, the infrared radiation condensing means 40 may be arranged to introduce infrared radiation to the infrared radiation detector 50 by another optical system by position a reflection mirror or an optical fiber at the other focus of the elliptical mirror 92.

By positioning the exit optical system of infrared radiation, as shown in FIG. 34 infrared radiation exiting through the exit end surface of a substrate-to-be-monitored 12 is reflected by the spherical mirror 90, passes the confocus and arrives at the elliptical mirror 92. The infrared radiation reflected by the elliptical mirror 92 is condensed to the other focus of the elliptical mirror 92. Thus, by positioning the infrared radiation detector 50 at the other focus of the elliptical mirror 92, infrared radiation exiting through the declined parts of the front and the back sides of the substrate-to-be-monitored 12 can be efficiently detected. Information molecular vibrations on a substrate-to-be-monitored 12 in a larger surface area can be obtained.

As described above, according to the present embodiment, the infrared radiation condensing means 40 is arranged to condense infrared radiation exiting through the declined parts of the front and the back sides of a substrate-to-be-monitored 12, whereby higher detection sensitivity of detecting contaminants on the surfaces of a substrate-to-be-monitored can be obtained. Higher detection sensitivity of detecting contaminants can prevent dielectric breakdown and insulation deterioration of, e.g., gate oxide films, and higher fabrication yields can be attained.

[A Seventh Embodiment]

The surface state monitoring method and apparatus according to a seventh embodiment of the present invention will be explained with reference to FIGS. 35 to 38. The same members of the present embodiment as those of the surface state monitoring method and apparatus according to the first or the second embodiment are represented by the same reference numbers not to repeat or to simplify their explanation.

Figure 35:
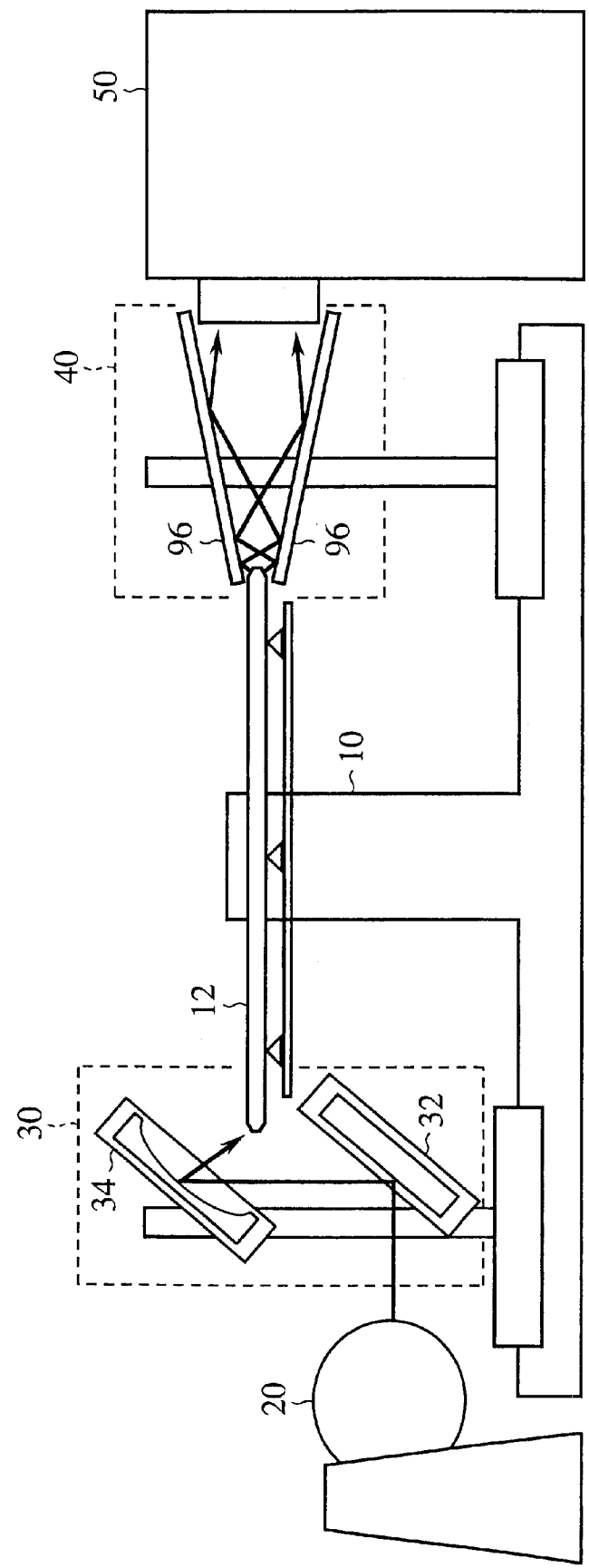
FIG. 35 is a diagrammatic view of infrared radiation condensing means according to a seventh embodiment of the present invention, which shows a structure thereof.
Figure 36:
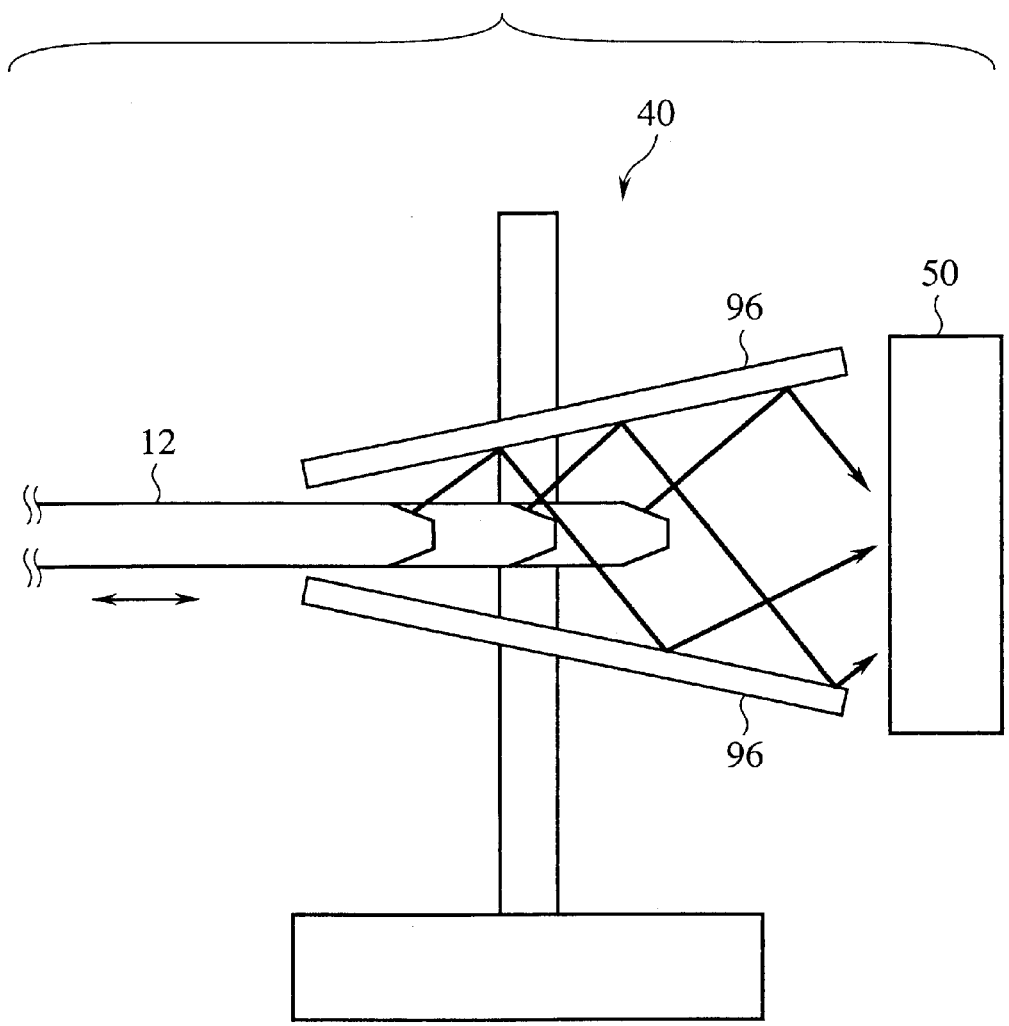
FIG. 36 is a view showing relationships between positions of a substrate-to-be-monitored with respect to the infrared radiation condensing means, and the infrared radiation optical path in the surface state monitoring apparatus shown in FIG. 35.
Figure 37A:
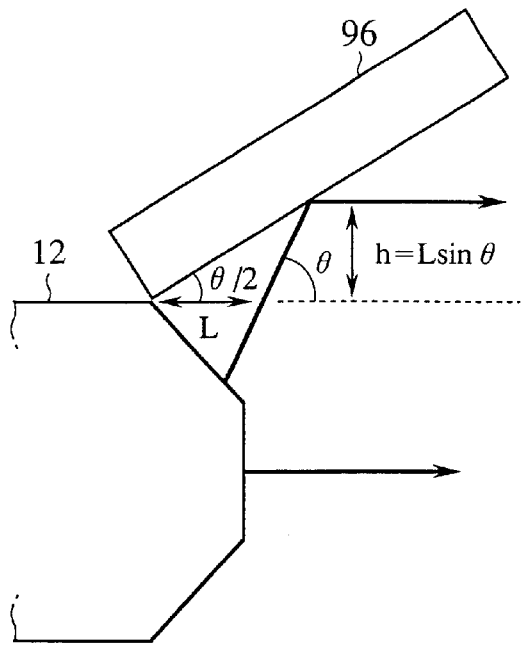
FIGS. 37A–37C are views showing relationships between arrangements of detection reflecting mirrors and incident angles of infrared radiation which enters an infrared radiation detector.
Figure 38:
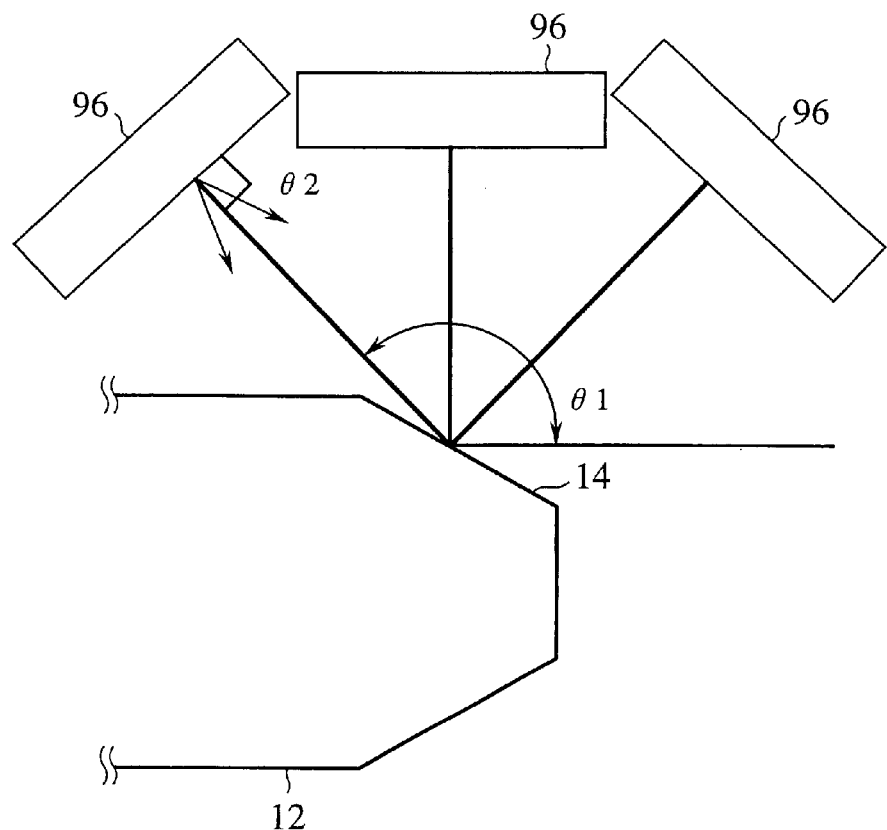
FIG. 38 is a view of relationships between arrangements of the detection reflecting mirrors and propagating directions of infrared radiation.

FIG. 35 is a diagrammatic view of infrared radiation condensing means according to the present embodiment, which shows a structure thereof. FIG. 36 is a view showing relationships between positions of a substrate-to-be-monitored with respect to the infrared radiation condensing means, and infrared radiation optical paths. FIGS. 37A–3C are views showing relationships between arrangements of a detection reflection mirror and incident angles of infrared radiation on an infrared radiation detector. FIG. 38 is a view showing relationships between arrangements of the detection reflecting mirror and propagating directions of infrared radiation.

In the present embodiment another infrared radiation condensing means for condensing infrared radiation exiting through both declined parts of the front and the back surfaces of a substrate-to-be-monitored and introducing the condensed infrared radiation into an infrared radiation detector will be explained.

As shown in FIG. 35, the infrared radiation condensing means 40 according to the present embodiment is characterized by being disposed near the infrared radiation exit ends of a substrate-to-be-monitored 12, and being constituted by a pair of detection reflecting mirrors 96 having a smaller gap on the side of the infrared radiation detector 50 than a gap on the side of the substrate-to-be-monitored 12.

This constitution of the surface state monitoring apparatus allows infrared radiation exiting through the end surface of the front surface of a substrate-to-be-monitored 12 and infrared radiation exiting through the end surface of the back surface of the substrate-to-be-monitored 12 to propagate toward the infrared radiation detector 50, repeating reflection between the detection reflecting mirrors 96 of the pair. Thus, infrared radiation exiting through the end surface of the back surface of a substrate-to-be-monitored 12 in addition to that exiting through the end surface of the front surface of the substrate-to-be-monitored 12 can be condensed, so that efficiency of condensing the transmitted infrared radiation can be higher in comparison with that of the surface state monitoring apparatus according to the first and the second embodiments.

As shown in FIG. 36, the surface state monitoring apparatus shown in FIG. 35 according to the present embodiment allows infrared radiation exiting through the end surfaces of a substrate-to-be-monitored 12 to be reflected on the detection reflecting mirrors 96 as long as the end surfaces of the substrate-to-be-monitored 12 are positioned between the detection reflecting mirrors 96 of the pair even when a position of the end surfaces of the substrate-to-be-monitored 12 is changed. The detection reflecting mirrors 96, which covers the infrared radiation detector 50 up to a position of the entrance window thereof, permits the transmitted infrared radiation to reach, without failure, an incident position of the infrared radiation detector 50, repeating reflection between the upper and the lower detection reflecting mirrors 96. Accordingly position adjustment of a substrate-to-be-monitored 12 and position adjustment of the detection reflecting mirror 96 are unnecessary, which can drastically simplify operation of the optical axis adjustment.

Figure 37B:
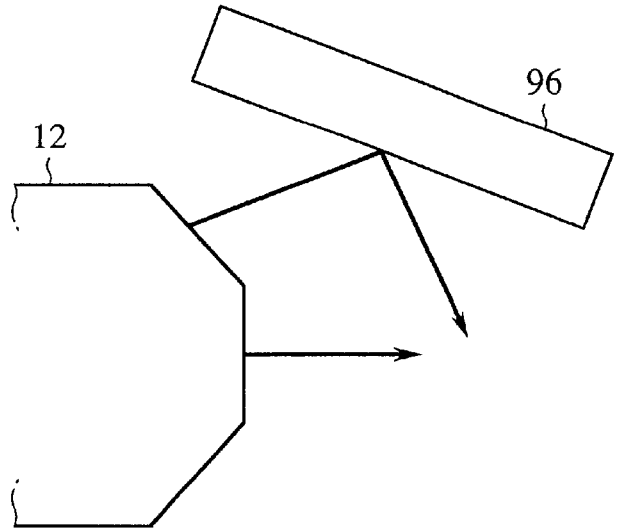
Figure 37C:
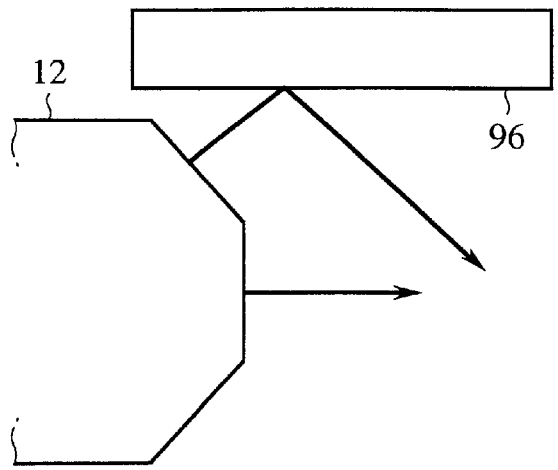

Three arrangements of a pair of the reflecting mirrors constituting the detection reflecting mirrors 96 are considered: a smaller gap on the side of a substrate-to-be-monitored and a wider gap on the side of the infrared radiation detector (see FIG. 37A); a wider gap on the side of a substrate-to-be-monitored 12 and a smaller gap on the side of the infrared radiation detector (see FIG. 37B); and two substantially parallel reflecting mirrors (see FIG. 37C). However, it is preferable that a pair of reflecting mirrors constituting the detection reflecting mirrors are arranged, as shown in FIG. 35, with a smaller gap on the side of a substrate-to-be-monitored and a larger gap on the side of the infrared radiation detector 50.

A first reason for this preferable arrangement is that infrared radiation exiting through the end surfaces of a substrate-to-be-monitored 12 can be incident on the infrared radiation detector 50 in substantially parallel rays by only this arrangement.

Condensing mirrors of infrared radiation detectors and spectroscopes are designed on condition that substantially parallel rays are incident. Accordingly, in order to prevent decrease of aberration and efficiency of condensing mirrors due to angular displacement of rays for efficient incidence of infrared radiation, it is necessary to transform infrared radiation exiting through the end surfaces of a substrate-to-be-monitored 12 into substantially parallel rays.

In the arrangement of the detection reflecting mirrors 96 according to the present embodiment shown in FIG. 37A, the reflecting mirrors 96 are tilted by θ/2 with respect to an arbitrary exit angle θ which is smaller than a right angle, whereby substantially parallel rays can be obtained by once reflection. A position of the substantially parallel rays is determined by a distance over which the end surfaces of a substrate-to-be-monitored are inserted into the detection reflecting mirrors and is given by:

$$h = L \times \sin\theta$$

wherein an inserted distance is represented by L, and a position of a height of the infrared radiation source is represented by h. An inserted distance of the end surfaces of a substrate-to-be-monitored 12 is adjusted, whereby substantially parallel rays which do not exceed a size of the entrance windows of detectors and spectroscopes can be obtained.

On the other hand, it is apparent that in the arrangements shown in FIGS. 37B and 37C conditions for transforming the reflected light into substantially parallel rays are absent. No substantially parallel rays can be obtained unless substantially parallel rays exit through the outer peripheral surface of a substrate-to-be-monitored 12.

A second reason for the preferable arrangement is that depending on relationships between angles of incident light and positions of the reflecting mirrors, there are angles at which light exiting a substrate-to-be-monitored 12 is reflected not to the side of the infrared radiation detector 50 but to the side of the substrate-to-be-monitored 12, but the preferable one of the three arrangements, which is used in the present embodiment, makes small a range in which the exiting light is reflected to the side of a substrate-to-be-monitored 12.

As shown in FIG. 38, an angle at which a ray connecting the detection reflecting mirrors 96 and a substrate-to-be-monitored 12 forms a horizon is represented by $\theta_1$, and an angle formed by the ray with respect to the detection reflecting mirrors is $\theta_2$. Depending on relationships between angles of light exiting through the end surface of a substrate-to-be-monitored 12 and angles of the detection reflecting mirrors 96, there are conditions under which light which has exited the end surfaces of a substrate-to-be-monitored 12 is not incident on the side of the infrared radiation detector 50 but is reflected again to the side of the substrate-to-be-monitored 12. That is, light is reflected on the detection reflecting mirrors 96 always at the same reflection angle as an incident angle thereof. When an angle $\theta_2$ is larger than 90°, light exiting the end surfaces of a substrate-to-be-monitored is reflected to the side of the infrared radiation detector 50 and is reflected to the side of the substrate-to-be-monitored when an angle $\theta_2$ is smaller than 90°. Accordingly, to prohibit the light from reflecting to the side of the substrate-to-be-monitored 12 it is necessary that $\theta_2$ is larger than 90°. A range of angles satisfying this condition is $2\theta_1$. A largest range of an angle $\theta_1$ satisfying $\theta_2>90°$ is given by the arrangement of the reflecting mirrors according to the present embodiment. The arrangement of the reflecting mirrors according to the present embodiment can accommodate exiting light having a wider range of angles than the other arrangements of the reflecting mirrors.

As described above, according to the present embodiment, the infrared radiation condensing means 40 for condensing infrared radiation exiting a substrate-to-be-monitored 12 is constituted by a pair of detection reflecting mirrors 96 having a smaller gap on the side of the substrate-to-be-monitored 12 than that on the side of the infrared radiation detector 50, so that infrared radiation exiting both the declined surfaces 14 of the front side and the back side of the substrate-to-be-monitored 12 can be detected. Thus, higher detection sensitivity of detecting contaminants on the surfaces of a substrate-to-be-monitored can be obtained. Because of higher detection sensitivity of detecting contaminants, dielectric breakdown and insulation deterioration of, e.g., gate oxide films can be prevented, and as a result, higher fabrication yields can be obtained.

In the present embodiment, the infrared radiation condensing means 40 is constituted by a pair of detection reflecting mirrors 96 positioned above and below a substrate-to-be-monitored 12, but a pair of reflecting mirrors may be further disposed on the sides of the reflecting mirrors 96 of the pair. Much higher detection sensitivity of detecting infrared radiation can be obtained. A pair of reflecting mirrors thus disposed may be plane mirrors or curved reflecting mirrors having a suitable curvature.

The infrared radiation condensing means may be constituted by a pair of detection reflecting mirrors 96 having one or both of the mirrors made movable to thereby optionally change an angle of the reflected light.

[An Eighth Embodiment]

The surface state monitoring method and apparatus according to an eighth embodiment of the present invention will be explained with reference to FIGS. 39 and 40. The same members of the present embodiment as those of the surface state monitoring method and apparatus according to the first or the second embodiment shown in FIGS. 1 to 16 are represented by the same reference numbers not to repeat or to simplify their explanation.

Figure 39:
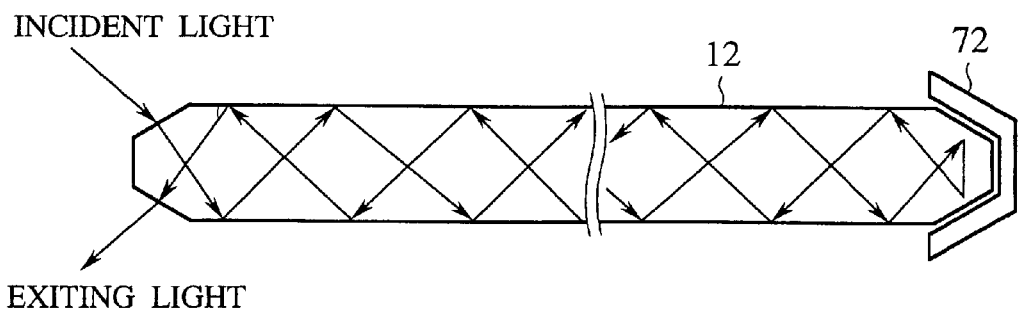
FIG. 39 is a diagrammatic view explaining the surface state monitoring method and apparatus according to an eighth embodiment of the present invention.
Figure 40A:
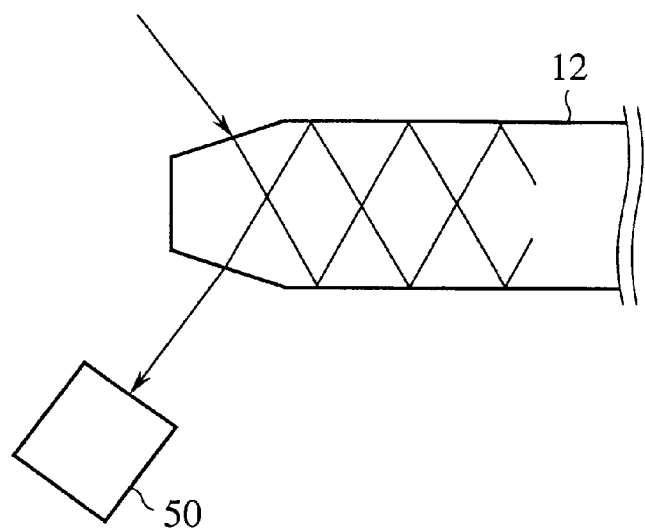
FIGS. 40A and 40B are diagrammatic views explaining another surface state monitoring method and apparatus according to an eighth embodiment of the present invention.
Figure 40B:
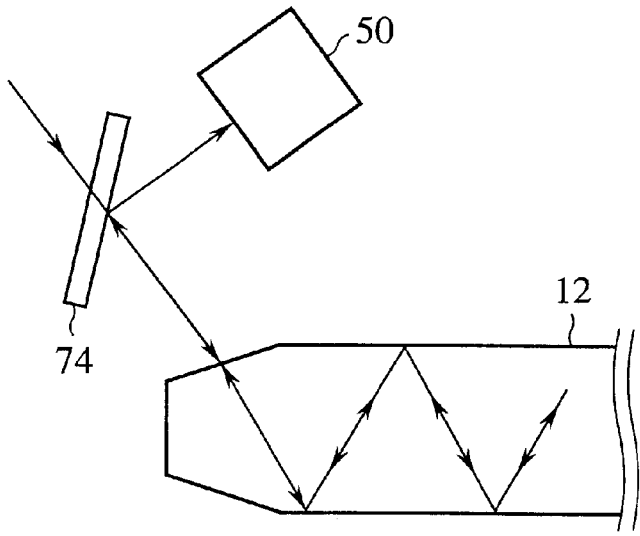

FIG. 39 is a diagrammatic view explaining the surface state monitoring method and apparatus according to the present embodiment. FIGS. 40A and 40B are views explaining another surface state monitoring method and apparatus according to the present embodiment.

As shown in FIG. 39, the surface state monitoring method and apparatus according to the present embodiment is characterized in that a reflecting mirror 72 is disposed on the side of one end surfaces of a substrate-to-be-monitored 12, and infrared radiation enters and exits through the other end surfaces of the substrate-to-be-monitored 12.

In the surface state monitoring apparatus having such constitution, infrared radiation incident on one end surfaces of a substrate-to-be-monitored 12 arrives at the other end surfaces opposed to one end surfaces, repeating internal multiple reflection, then is reflected by the reflecting mirror 72 on one end surfaces, reaches the other end surfaces, again repeating internal multiple reflection and exits the substrate-to-be-monitored 12 through the other end surfaces, and is detected by an infrared radiation detector 50. Infrared radiation can travel along a long optical path in a substrate-to-be-monitored 12 and can undergo the multiple reflection by a large number of times. Accordingly, more surface states can be probed. Higher sensitivity of detecting surfaces states of a substrate-to-be-monitored 12 can be obtained.

To constitute a propagation optical system for such propagation of infrared radiation, various arrangements of the infrared radiation incidence optical system and exit optical system can be considered.

As exemplified in FIG. 40A, an infrared radiation source 20, infrared radiation condensing means 30, 40 and an infrared radiation detector 50 are arranged so that infrared radiation is incident on the declined part 14 of the front surface of a substrate-to-be-monitored 12, and infrared radiation exiting through the declined part 14 of the back surface is detected.

As shown in FIG. 40B, it is possible that a half mirror 74 is inserted in the incidence optical path of infrared radiation, and the infrared radiation source 20, the infrared radiation condensing means 30, 40 and the infrared radiation detector 50 are arranged so that applied infrared radiation passes the half mirror 74 to be incident on a substrate-to-be-monitored 12, and the infrared radiation exiting is reflected by the half mirror 74 to be led to the infrared radiation detector 50.

As described above, according to the present embodiment, infrared radiation incident on an end surface of a substrate-to-be-monitored 12 reciprocates, repeating reflections inside the substrate-to-be-monitored 12, and the infrared radiation exiting through the incident end surface is detected to monitor surface states of the substrate-to-be-monitored. Higher detection sensitivity of detecting surface states of a substrate-to-be-monitored 12 can be obtained.

What is claimed is:

1. A surface state monitoring apparatus comprising:
    a first infrared radiation condensing means for condensing infrared radiation emitted by an infrared radiation source on an outer peripheral part of a substrate-to-be-monitored and introducing the infrared radiation into the substrate-to-be-monitored;
    an incident angle control means for controlling an incident angle of the infrared radiation condensed by the first infrared radiation condensing means, which enters the substrate-to-be-monitored to be fixed to a prescribed value or to be variable;

a second infrared radiation condensing means for condensing the infrared radiation which has undergone multiple reflection in the substrate-to-be-monitored and exits the substrate-to-be-monitored;

an infrared radiation detecting means for detecting the infrared radiation condensed by the second infrared radiation condensing means; and an infrared radiation analyzing means for analyzing the infrared radiation detected by the infrared radiation detecting means to measure contaminants staying on the surfaces of the substrate-to-be-monitored.

2. A surface state monitoring apparatus according to claim 1, wherein the incident angle control means controls an incident angle of the infrared radiation entering the substrate-to-be-monitored so that a reflection angle of the infrared radiation inside the substrate-to-be-monitored is below a total reflection critical angle.

3. A surface state monitoring apparatus according to claim 1, wherein the incident angle control means controls an incident angle of the infrared radiation entering the substrate-to-be-monitored so that an energy reflectivity of the infrared radiation at the time of entering the substrate-to-be-monitored is below a prescribed value.

4. A surface state monitoring apparatus according to claim 1, wherein the infrared radiation analyzing means identifies the contaminants, based on a spectroscopic result given by Fourier transform spectroscopy.

5. A surface state monitoring apparatus according to claim 1, wherein the infrared radiation analyzing means identifies the contaminants, based on a spectroscopic result given by infrared spectroscopy using a diffraction grating.

6. A surface state monitoring apparatus according to claim 1, wherein the substrate-to-be-monitored has a pair of declined parts on outer peripheral parts, which are formed by chamfering the edges defined by a pair of surfaces of the substrate-to-be-monitored and the outer peripheral surface thereof, and the first infrared radiation condensing means condenses the infrared radiation on one or both of the pair of the declined parts of the substrate-to-be-monitored.

7. A surface state monitoring apparatus according to claim 1, further comprising:

a substrate mount including a position control mechanism for supporting the substrate-to-be-monitored and adjusting a position of the infrared radiation incident on the substrate-to-be-monitored, and a rotation mechanism for rotating the substrate-to-be-monitored.

8. A surface state monitoring apparatus according to claim 1, wherein the first infrared radiation condensing means condenses the infrared radiation emitted by the infrared radiation source to an elliptical focus or a circular focus along an outer periphery of the substrate-to-be-monitored.

9. A surface state monitoring apparatus according to claim 1, wherein the first infrared condensing means includes a spherical mirror, and an elliptical mirror positioned so as to position one focus of the elliptical mirror at a focus of the spherical mirror;

the infrared radiation source is positioned at said one focus of the elliptical mirror; and the first infrared radiation condensing means condenses the infrared radiation emitted by the infrared radiation source to the other focus of the elliptical mirror.

10. A surface state monitoring apparatus according to claim 1, wherein the second infrared radiation condensing means includes a spherical mirror, and an elliptical mirror positioned so as to position one focus of the elliptical mirror at a focus of the spherical mirror;

the substrate-to-be-monitored is positioned so that an exit end surface of the substrate-to-be-monitored through which the infrared radiation exits is positioned at said one focus of the elliptical mirror; and the second infrared radiation condensing means condenses the infrared radiation exiting the substrate-to-be-monitored to the other focus of the elliptical mirror.

11. A surface state monitoring apparatus according to claim 1, wherein the second infrared radiation condensing means includes a pair of reflecting mirrors which are opposed to each other with a gap therebetween on a side of the substrate-to-be-monitored being smaller than a gap therebetween on a side of the infrared radiation detecting means.

12. A surface state monitoring apparatus according to claim 1, comprising:

a reflecting mirror disposed on an end surface of the substrate-to-be-monitored opposed to the end surface thereof on which the infrared radiation is incident, the reflecting mirror reflecting the infrared radiation exiting the substrate-to-be-monitored and introducing the infrared radiation again into the substrate-to-be-monitored.

13. A surface state monitoring apparatus according to claim 1, wherein the substrate-to-be-monitored is a substrate having a pair of substantially parallel surfaces polished.

14. A surface state monitoring apparatus according to claim 1, wherein the infrared radiation source includes a light source for emitting infrared radiation or near-infrared radiation, and an optical system for transforming light emitted by the light source into substantially parallel rays.

15. A surface state monitoring apparatus according to claim 1, wherein the substrate-to-be-monitored is a substrate which allows the infrared radiation to reflect more than 300 times in the substrate-to-be-monitored.

16. A surface state monitoring apparatus according to claim 1, wherein the substrate-to-be-monitored is monitored before being subjected to certain processing, after being subjected to certain processing or in certain processing.

17. A surface state monitoring apparatus comprising:

a first infrared radiation condenser for condensing infrared radiation emitted by an infrared radiation source on an outer peripheral part of a substrate-to-be-monitored and introducing the infrared radiation into the substrate-to-be-monitored;

an incident angle controller for controlling an incident angle of the infrared radiation condensed by the first infrared radiation condenser, which enters the substrate-to-be-monitored to be fixed to a prescribed value or to be variable;

a second infrared radiation condenser for condensing the infrared radiation which has undergone multiple reflection in the substrate-to-be-monitored and exits the substrate-to-be-monitored;

an infrared radiation detector for detecting the infrared radiation condensed by the second infrared radiation condenser; and an infrared radiation analyzer for analyzing the infrared radiation detected by the infrared radiation detector to measure contaminants staying on the surfaces of the substrate-to-be-monitored.

18. A surface state monitoring method comprising:

condensing infrared radiation to an outer peripheral part of the substrate-to-be-monitored with an incident angle of the infrared radiation fixed to a required value or changed to introduce the infrared radiation into the substrate-to-be-monitored through the outer peripheral part;

detecting the infrared radiation which has undergone internal multiple reflection in the substrate-to-be-monitored and exited the substrate-to-be-monitored; and analyzing the detected infrared radiation to measure contaminants staying on the surfaces of the substrate-to-be-monitored.

19. A surface state monitoring method according to claim 18, wherein the infrared radiation which has exited the substrate-to-be-monitored is subjected to Fourier transform spectroscopy, and the contaminants are identified based on a result of the spectroscopy.

20. A surface state monitoring method according to claim 18, wherein the infrared radiation which has exited the substrate-to-be-monitored is subjected to the spectroscopy by using a diffraction grating, and the contaminants are identified based on a result of the spectroscopy.

21. A surface state monitoring method according to claim 18, wherein the incident angle of the infrared radiation incident on the substrate-to-be-monitored is controlled in a range in which a reflecting angle of the infrared radiation in the substrate-to-be-monitored is larger than 0° and not more than a total reflection critical angle.

22. A surface state monitoring method according to claim 18, wherein an incident angle of the infrared radiation incident on the substrate-to-be-monitored is controlled in a range in which an energy reflectivity of the infrared radiation at the time of the infrared radiation entering the substrate-to-be-monitored is below a prescribed value.

23. A surface state monitoring method according to claim 18, wherein the infrared radiation is caused to enter the substrate-to-be-monitored through one or both of a pair of declined parts on the outer peripheral part, which are formed by chamfering the edges defined by a pair of surfaces of the substrate-to-be-monitored and the outer peripheral surface thereof.

24. A surface state monitoring method according to claim 18, wherein the infrared radiation which has entered the substrate-to-be-monitored is reciprocated in the substrate-to-be-monitored, exits the substrate-to-be-monitored through an end surface through which the infrared radiation has entered, and is detected.

25. A surface state monitoring method according to claim 18, wherein the substrate-to-be-monitored is a substrate having a pair of substantially parallel polished surfaces.

26. A surface state monitoring method according to claim 18, wherein a position of a substrate mount for supporting the substrate-to-be-monitored is controlled so that an amount of the infrared radiation which is detected after the infrared radiation has undergone internal multiple reflection in the substrate-to-be-monitored is maximum.

27. A surface state monitoring method according to claim 18, wherein the substrate-to-be-monitored is monitored several times, being rotated to monitor the surfaces of the substrate-to-be-monitored substantially all over the surfaces of the substrate-to-be-monitored.

28. A surface state monitoring method according to claim 18, wherein the infrared radiation is condensed to an elliptical focus or a circular focus to be incident on the substrate-to-be-monitored.

29. A surface state monitoring method comprising:

condensing infrared radiation to an outer peripheral part of a substrate-to-be-monitored, scanning incident angles in a prescribed range to introduce the infrared radiation into the substrate-to-be-monitored through the outer peripheral part;

detecting the infrared radiation which has undergone internal multiple reflection in the substrate-to-be-monitored and exited the substrate-to-be-monitored; and analyzing the detected infrared radiation to measure contaminants staying on the surfaces of the substrate-to-be-monitored.

30. A surface state monitoring method according to claim 29, wherein the infrared radiation which has exited the substrate-to-be-monitored is subjected to Fourier transform spectroscopy, and the contaminants are identified based on a result of the spectroscopy.

31. A surface state monitoring method according to claim 29, wherein the infrared radiation which has exited the substrate-to-be-monitored is subjected to the spectroscopy by using a diffraction grating, and the contaminants are identified based on a result of the spectroscopy.

32. A surface state monitoring method according to claim 29, wherein the incident angle of the infrared radiation incident on the substrate-to-be-monitored is controlled in a range in which a reflecting angle of the infrared radiation in the substrate-to-be-monitored is larger than 0° and not more than a total reflection critical angle.

33. A surface state monitoring method according to claim 29, wherein an incident angle of the infrared radiation incident on the substrate-to-be-monitored is controlled in a range in which an energy reflectivity of the infrared radiation at the time of the infrared radiation entering the substrate-to-be-monitored is below a prescribed value.

34. A surface state monitoring method according to claim 29, wherein the infrared radiation is caused to enter the substrate-to-be-monitored through one or both of a pair of declined parts on the outer peripheral part, which are formed by chamfering the edges defined by a pair of surfaces of the substrate-to-be-monitored and the outer peripheral surface thereof.

35. A surface state monitoring method according to claim 29, wherein
the infrared radiation which has entered the substrate-to-be-monitored is reciprocated in the substrate-to-be-monitored, exits the substrate-to-be-monitored through an end surface through which the infrared radiation has entered, and is detected.

36. A surface state monitoring method according to claim 29, wherein
the substrate-to-be-monitored is a substrate having a pair of substantially parallel polished surfaces.

37. A surface state monitoring method according to claim 29, wherein
a position of a substrate mount for supporting the substrate-to-be-monitored is controlled so that an amount of the infrared radiation which is detected after the infrared radiation has undergone internal multiple reflection in the substrate-to-be-monitored is maximum.

38. A surface state monitoring method according to claim 29, wherein
the substrate-to-be-monitored is monitored several times, being rotated to monitor the surfaces of the substrate-to-be-monitored substantially all over the surfaces of the substrate-to-be-monitored.

39. A surface state monitoring method according to claim 29, wherein
the infrared radiation is condensed to an elliptical focus or a circular focus to be incident on the substrate-to-be-monitored.

40. A surface state monitoring method comprising:
condensing infrared radiation to an outer peripheral part of a substrate-to-be-monitored with an incident angle fixed to a prescribed value or changed to introduce the infrared radiation into the substrate-to-be-monitored through the outer peripheral part;
detecting the infrared radiation which has undergone internal multiple reflection in the substrate-to-be-monitored and exited the substrate-to-be-monitored; and
comparing an intensity of the detected infrared radiation with a reference intensity, and it is judged whether the substrate-to-be-monitored is good or not, based on a result of the comparison.

41. A surface state monitoring method according to claim 40, wherein
the incident angle of the infrared radiation incident on the substrate-to-be-monitored is controlled in a range in which a reflecting angle of the infrared radiation in the substrate-to-be-monitored is larger than 0° and not more than a total reflection critical angle.

42. A surface state monitoring method according to claim 40, wherein
an incident angle of the infrared radiation incident on the substrate-to-be-monitored is controlled in a range in which an energy reflectivity of the infrared radiation at the time of the infrared radiation entering the substrate-to-be-monitored is below a prescribed value.

43. A surface state monitoring method according to claim 40, wherein
the infrared radiation is caused to enter the substrate-to-be-monitored through one or both of a pair of declined parts on the outer peripheral part, which are formed by chamfering the edges defined by a pair of surfaces of the substrate-to-be-monitored and the outer peripheral surface thereof.

44. A surface state monitoring method according to claim 40, wherein
the infrared radiation which has entered the substrate-to-be-monitored is reciprocated in the substrate-to-be-monitored, exits the substrate-to-be-monitored through an end surface through which the infrared radiation has entered, and is detected.

45. A surface state monitoring method according to claim 40, wherein
the substrate-to-be-monitored is a substrate having a pair of substantially parallel polished surfaces.

46. A surface state monitoring method according to claim 40, wherein
a position of a substrate mount for supporting the substrate-to-be-monitored is controlled so that an amount of the infrared radiation which is detected after the infrared radiation has undergone internal multiple reflection in the substrate-to-be-monitored is maximum.

47. A surface state monitoring method according to claim 40, wherein
the substrate-to-be-monitored is monitored several times, being rotated to monitor the surfaces of the substrate-to-be-monitored substantially all over the surfaces of the substrate-to-be-monitored.

48. A surface state monitoring method according to claim 40, wherein
the infrared radiation is condensed to an elliptical focus or a circular focus to be incident on the substrate-to-be-monitored.

49. A surface state monitoring method comprising:
condensing infrared radiation to an outer peripheral part of a substrate-to-be-monitored with an incident angle fixed to a prescribed value or changed to introduce the infrared radiation into the substrate-to-be-monitored through the outer peripheral part;
detecting selectively that of the infrared radiation having undergone internal multiple reflection in the substrate-to-be-monitored and exited the substrate-to-be-monitored, which is in a wavelength range corresponding to a molecular vibration of a specific contaminant; and
computing an amount of the specific contaminant staying on the surfaces of the substrate-to-be-monitored, based on an intensity of the detected infrared radiation.

50. A surface state monitoring method according to claim 49, wherein
the incident angle of the infrared radiation incident on the substrate-to-be-monitored is controlled in a range in which a reflecting angle of the infrared radiation in the substrate-to-be-monitored is larger than 0° and not more than a total reflection critical angle.

51. A surface state monitoring method according to claim 49, wherein
an incident angle of the infrared radiation incident on the substrate-to-be-monitored is controlled in a range in which an energy reflectivity of the infrared radiation at the time of the infrared radiation entering the substrate-to-be-monitored is below a prescribed value.

52. A surface state monitoring method according to claim 49, wherein the infrared radiation is caused to enter the substrate-to-be-monitored through one or both of a pair of declined parts on the outer peripheral part, which are formed by chamfering the edges defined by a pair of surfaces of the substrate-to-be-monitored and the outer peripheral surface thereof.

53. A surface state monitoring method according to claim 49, wherein the infrared radiation which has entered the substrate-to-be-monitored is reciprocated in the substrate-to-be-monitored, exits the substrate-to-be-monitored through an end surface through which the infrared radiation has entered, and is detected.

54. A surface state monitoring method according to claim 49, wherein the substrate-to-be-monitored is a substrate having a pair of substantially parallel polished surfaces.

55. A surface state monitoring method according to claim 49, wherein a position of a substrate mount for supporting the substrate-to-be-monitored is controlled so that an amount of the infrared radiation which is detected after the infrared radiation has undergone internal multiple reflection in the substrate-to-be-monitored is maximum.

56. A surface state monitoring method according to claim 49, wherein the substrate-to-be-monitored is monitored several times, being rotated to monitor the surfaces of the substrate-to-be-monitored substantially all over the surfaces of the substrate-to-be-monitored.

57. A surface state monitoring method according to claim 49, wherein the infrared radiation is condensed to an elliptical focus or a circular focus to be incident on the substrate-to-be-monitored.

* * * * *